United States Patent
Cook et al.

(10) Patent No.: US 11,780,898 B2
(45) Date of Patent: Oct. 10, 2023

(54) TREATMENT OF SMC MEDIATED DISEASE

(71) Applicants: Singapore Health Services PTE LTD, Singapore (SG); National University of Singapore, Singapore (SG)

(72) Inventors: Stuart Alexander Cook, Singapore (SG); Sebastian Schaefer, Singapore (SG); Wei Wen Lim, Singapore (SG); Benjamin Wei Ming Ng, Singapore (SG)

(73) Assignees: Singapore Health Services PTE LTD., Singapore (SG); National University of Singapore, Singapore (SG)

( * ) Notice: Subject to any disclaimer, the term of this patent is extended or adjusted under 35 U.S.C. 154(b) by 0 days.

(21) Appl. No.: 16/158,528

(22) Filed: Oct. 12, 2018

(65) Prior Publication Data

US 2019/0241637 A1  Aug. 8, 2019

(30) Foreign Application Priority Data

Oct. 12, 2017 (GB) .................................. 1716733

(51) Int. Cl.

| | |
|---|---|
| A61K 38/20 | (2006.01) |
| C07K 14/54 | (2006.01) |
| C07K 16/28 | (2006.01) |
| C07K 16/24 | (2006.01) |
| A61K 39/00 | (2006.01) |
| A61P 9/10 | (2006.01) |
| A61P 35/00 | (2006.01) |
| A61K 31/7088 | (2006.01) |
| A61K 38/00 | (2006.01) |

(52) U.S. Cl.
CPC ...... *C07K 14/5431* (2013.01); *A61K 31/7088* (2013.01); *A61K 39/00* (2013.01); *A61P 9/10* (2018.01); *A61P 35/00* (2018.01); *C07K 16/24* (2013.01); *C07K 16/244* (2013.01); *C07K 16/28* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,518,888 B2 * | 8/2013 | Jenkins ............... | C07K 16/2866 514/19.3 |
| 2009/0202533 A1 * | 8/2009 | Baca ..................... | A61K 38/02 424/133.1 |
| 2010/0144646 A1 | 6/2010 | Paterson | |
| 2014/0219919 A1 | 8/2014 | Edwards et al. | |
| 2017/0174759 A1 * | 6/2017 | Cook ................. | C12N 15/1136 |
| 2020/0031920 A1 * | 1/2020 | Zhu ..................... | C07K 16/2866 |
| 2020/0113921 A1 * | 4/2020 | Petkov ................... | A61P 27/14 |

FOREIGN PATENT DOCUMENTS

| | | |
|---|---|---|
| KR | 20110047179 A | 5/2011 |
| WO | WO 2005/070446 A1 | 8/2005 |
| WO | WO 2017/049349 A1 | 3/2017 |

OTHER PUBLICATIONS

Ha et al.,( J Transl Med (2016) 14:39 pp. 1-14). (Year: 2016).*
Kobayashi et al. Blood (1993) vol. 81, No. 4, pp. 889-893. (Year: 1993).*
Schmidt et al., (J. Allergy Clin. Immunol.(2000) 105, pp. 673-682). (Year: 2000).*
Monroy et al., (Front Biosci (Landmark Ed). ; 20: 784-795 (Year: 2016).*
Steinhoff et al., (J. Allergy Clin Immunol., vol. 118, pp. 190-197). (Year: 2006).*
Ancey et al., A fusion protein of the gp130 and interleukin-6Ralpha ligand-binding domains acts as a potent interleukin-6 inhibitor. J Biol Chem. May 9, 2003;278(19):16968-72. Epub Mar. 19, 2003.
Lee et al., Cysteinyl leukotriene upregulates IL-11 expression in allergic airway disease of mice. J Allergy Clin Immunol. Jan. 2007;119(1):141-9. Epub Oct. 27, 2006.
Metz et al., Characterization of the Interleukin (IL)-6 Inhibitor IL-6-RFP: fused receptor domains act as high affinity cytokine-binding proteins. J Biol Chem. Jan. 12, 2007;282(2):1238-48. Epub Nov. 3, 2006.
Rainger et al., Cellular pathology of atherosclerosis: smooth muscle cells prime cocultured endothelial cells for enhanced leukocyte adhesion. Circ Res. Mar. 30, 2001;88(6):615-22.
Shea-Donohue et al., Mechanisms of smooth muscle responses to inflammation. Neurogastroenterol Motil. Sep. 2012;24(9):802-11. doi:10.1111/j.1365-2982.2012.01986.x.
*U.S. Appl. No. 16/055,245, filed Aug. 6, 2018, Cook et al.
*U.S. Appl. No. 16/055,251, filed Aug. 6, 2018, Cook et al.
*U.S. Appl. No. 16/055,261, filed Aug. 6, 2018, Cook et al.
*U.S. Appl. No. 16/055,270, filed Aug. 6, 2018, Cook et al.
*U.S. Appl. No. 16/055,283, filed Aug. 6, 2018, Cook et al.
*U.S. Appl. No. 16/055,295, filed Aug. 6, 2018, Cook et al.
*U.S. Appl. No. 16/055,304, filed Aug. 6, 2018, Cook et al.
*U.S. Appl. No. 16/055,319, filed Aug. 6, 2018, Cook et al.
*U.S. Appl. No. 16/106,041, filed Aug. 21, 2018, Cook et al.
*U.S. Appl. No. 16/106,044, filed Aug. 21, 2018, Cook et al.
*U.S. Appl. No. 16/106,047, filed Aug. 21, 2018, Cook et al.
*U.S. Appl. No. 16/106,050, filed Aug. 21, 2018, Cook et al.
*U.S. Appl. No. 16/726,173, filed Dec. 23, 2019, Cook et al.
*U.S. Appl. No. 16/726,190, filed Dec. 23, 2019, Cook et al.
*U.S. Appl. No. 16/440,840, filed Jun. 13, 2019, Cook et al.
*U.S. Appl. No. 16/440,876, filed Jun. 13, 2019, Cook et al.
*U.S. Appl. No. 16/748,698, filed Jan. 21, 2020, Cook et al.
*U.S. Appl. No. 16/798,101, filed Feb. 21, 2020, Cook et al.
*U.S. Appl. No. 16/865,259, filed May 1, 2020, Cook et al.
Lim et al., Transgenic interleukin 11 expression causes cross-tissue fibro-inflammation and an inflammatory bowel phenotype in mice. PLoS One. Jan. 9, 2020;15(1):e0227505. doi: 10.1371/journal.pone. 0227505.

(Continued)

*Primary Examiner* — Michael D Pak
(74) *Attorney, Agent, or Firm* — Wolf, Greenfield & Sacks, P.C.

(57) ABSTRACT

Diagnosis, treatment and prophylaxis of diseases and conditions associated with smooth muscle cell (SMC) dysfunction are provided through the inhibition of IL-11-mediated signalling.

8 Claims, 47 Drawing Sheets

Specification includes a Sequence Listing.

(56) References Cited

OTHER PUBLICATIONS

Milara et al., IL-11 system participates in pulmonary artery remodeling and hypertension in pulmonary fibrosis. Respir Res. Nov. 15, 2022;23(1):313. doi: 10.1186/s12931-022-02241-0.

Greenwood-Van Meerveld et al., Recombinant human interleukin-11 restores smooth muscle function in the jejunum and colon of human leukocyte antigen-B27 rats with intestinal inflammation. J Pharmacol Exp Ther. Oct. 2001; 299(1):58-66.

Lebastchi et al., Activation of human vascular cells decreases their expression of transforming growth factor-beta. Atherosclerosis. Dec. 2011;219(2):417-24. doi: 10.1016/j.atherosclerosis.2011.07.121. Epub Aug. 5, 2011.

Rzucidlo et al., Regulation of vascular smooth muscle cell differentiation. J Vasc Surg. Jun. 2007;45 Suppl A:A25-32. doi: 10.1016/j.jvs.2007.03.001.

Wang et al., Origin and differentiation of vascular smooth muscle cells. J Physiol. Jul. 15, 2015;593(14):3013-30. doi: 10.1113/JP270033. Epub Jun. 9, 2015.

\* cited by examiner

Fig. 35A

SEQUENCE LISTING

```
<160> NUMBER OF SEQ ID NOS: 47

<210> SEQ ID NO 1
<211> LENGTH: 199
<212> TYPE: PRT
<213> ORGANISM: Homo sapiens

<400> SEQUENCE: 1

Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140
```

-continued

```
Ser Arg Leu Ala Leu Pro Gln Pro Pro Asp Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
            195

<210> SEQ ID NO 2
<211> LENGTH: 918
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320
```

-continued

```
Thr Tyr Glu Asp Arg Pro Ser Lys Ala Pro Ser Phe Trp Tyr Lys Ile
            325                 330                 335

Asp Pro Ser His Thr Gln Gly Tyr Arg Thr Val Gln Leu Val Trp Lys
        340                 345                 350

Thr Leu Pro Pro Phe Glu Ala Asn Gly Lys Ile Leu Asp Tyr Glu Val
    355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
            405                 410                 415

Pro Ala Cys Asp Phe Gln Ala Thr His Pro Val Met Asp Leu Lys Ala
        420                 425                 430

Phe Pro Lys Asp Asn Met Leu Trp Val Glu Trp Thr Thr Pro Arg Glu
    435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
        500                 505                 510

Tyr Leu Lys Gln Ala Pro Pro Ser Lys Gly Pro Thr Val Arg Thr Lys
    515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
            565                 570                 575

Tyr Thr Leu Ser Ser Leu Thr Ser Asp Thr Leu Tyr Met Val Arg Met
        580                 585                 590

Ala Ala Tyr Thr Asp Glu Gly Gly Lys Asp Gly Pro Glu Phe Thr Phe
    595                 600                 605

Thr Thr Pro Lys Phe Ala Gln Gly Glu Ile Glu Ala Ile Val Val Pro
610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
            645                 650                 655

Asp Pro Ser Lys Ser His Ile Ala Gln Trp Ser Pro His Thr Pro Pro
        660                 665                 670

Arg His Asn Phe Asn Ser Lys Asp Gln Met Tyr Ser Asp Gly Asn Phe
    675                 680                 685

Thr Asp Val Ser Val Val Glu Ile Glu Ala Asn Asp Lys Lys Pro Phe
690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
            725                 730                 735
```

```
Ser Arg Pro Ser Ile Ser Ser Asp Glu Asn Glu Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 3
<211> LENGTH: 422
<212> TYPE: PRT
<213> ORGANISM: Homo sapiens

<400> SEQUENCE: 3

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190
```

```
Ile Asn Val Thr Glu Val Asn Pro Leu Gly Ala Ser Thr Arg Leu Leu
            195                 200                 205

Asp Val Ser Leu Gln Ser Ile Leu Arg Pro Asp Pro Gln Gly Leu
210                 215                 220

Arg Val Glu Ser Val Pro Gly Tyr Pro Arg Leu Arg Ala Ser Trp
225                 230                 235                 240

Thr Tyr Pro Ala Ser Pro Cys Gln Pro His Phe Leu Leu Lys Phe
                245                 250                 255

Arg Leu Gln Tyr Arg Pro Ala Gln His Pro Ala Trp Ser Thr Val Glu
                260                 265                 270

Pro Ala Gly Leu Glu Glu Val Ile Thr Asp Ala Val Ala Gly Leu Pro
                275                 280                 285

His Ala Val Arg Val Ser Ala Arg Asp Phe Leu Asp Ala Gly Thr Trp
290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
                340                 345                 350

His Pro Arg Leu Leu Asp His Arg Asp Ser Val Glu Gln Val Ala Val
                355                 360                 365

Leu Ala Ser Leu Gly Ile Leu Ser Phe Leu Gly Leu Val Ala Gly Ala
                370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
                420

<210> SEQ ID NO 4
<211> LENGTH: 516
<212> TYPE: PRT
<213> ORGANISM: Artificial Sequence
<220> FEATURE:
<223> OTHER INFORMATION: Hyper IL-11 (IL-11RA: IL-11 fusion)

<400> SEQUENCE: 4

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
                20                  25                  30

Pro Gly Val Gln Tyr Gly Gln Pro Gly Arg Ser Val Lys Leu Cys Cys
                35                  40                  45

Pro Gly Val Thr Ala Gly Asp Pro Val Ser Trp Phe Arg Asp Gly Glu
            50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
                100                 105                 110

Pro Ala Arg Pro Val Val Ser Cys Gln Ala Ala Asp Tyr Glu Asn Phe
                115                 120                 125
```

```
Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Pro Ala
305                 310                 315                 320

Gly Gln Ser Gly Gly Gly Gly Ser Gly Gly Ser Gly Gly Gly
                325                 330                 335

Ser Val Pro Gly Pro Pro Gly Pro Pro Arg Val Ser Pro Asp Pro
                340                 345                 350

Arg Ala Glu Leu Asp Ser Thr Val Leu Leu Thr Arg Ser Leu Leu Ala
                355                 360                 365

Asp Thr Arg Gln Leu Ala Ala Gln Leu Arg Asp Lys Phe Pro Ala Asp
    370                 375                 380

Gly Asp His Asn Leu Asp Ser Leu Pro Thr Leu Ala Met Ser Ala Gly
385                 390                 395                 400

Ala Leu Gly Ala Leu Gln Leu Pro Gly Val Leu Thr Arg Leu Arg Ala
                405                 410                 415

Asp Leu Leu Ser Tyr Leu Arg His Val Gln Trp Leu Arg Arg Ala Gly
            420                 425                 430

Gly Ser Ser Leu Lys Thr Leu Glu Pro Glu Leu Gly Thr Leu Gln Ala
            435                 440                 445

Arg Leu Asp Arg Leu Leu Arg Arg Leu Gln Leu Leu Met Ser Arg Leu
    450                 455                 460

Ala Leu Pro Gln Pro Pro Pro Asp Pro Pro Ala Pro Pro Leu Ala Pro
465                 470                 475                 480

Pro Ser Ser Ala Trp Gly Gly Ile Arg Ala Ala His Ala Ile Leu Gly
                485                 490                 495

Gly Leu His Leu Thr Leu Asp Trp Ala Val Arg Gly Leu Leu Leu Leu
            500                 505                 510

Lys Thr Arg Leu
        515
```

```
<210> SEQ ID NO 5
<211> LENGTH: 21
<212> TYPE: PRT
<213> ORGANISM: Artificial Sequence
<220> FEATURE:
<223> OTHER INFORMATION: 20 amino acid linker

<400> SEQUENCE: 5

Gly Pro Ala Gly Gln Ser Gly Gly Gly Gly Ser Gly Gly Gly Ser
1               5                   10                  15

Gly Gly Gly Ser Val
            20

<210> SEQ ID NO 6
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 6
ccttccaaag ccagatctt                                                19

<210> SEQ ID NO 7
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 7
gcctgggcag gaacatata                                                19

<210> SEQ ID NO 8
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 8
cctgggcagg aacatatat                                                19

<210> SEQ ID NO 9
<211> LENGTH: 19
<212> TYPE: DNA
<213> ORGANISM: Artificial Sequence
<220> FEATURE:
<223> OTHER INFORMATION: siRNA target IL-11

<400> SEQUENCE: 9
ggttcattat ggctgtgtt                                                19

<210> SEQ ID NO 10
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 10
ggaccatacc aaaggagat                                                19
```

-continued

```
<210> SEQ ID NO 11
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 11
gcgtctttgg gaatccttt                                                  19

<210> SEQ ID NO 12
<211> LENGTH: 18
<212> TYPE: DNA
<213> ORGANISM: Artificial Sequence
<220> FEATURE:
<223> OTHER INFORMATION: siRNA target IL-11Ralpha

<400> SEQUENCE: 12
gcaggacagt agatccct                                                   18

<210> SEQ ID NO 13
<211> LENGTH: 19
<212> TYPE: DNA
<213> ORGANISM: Artificial Sequence
<220> FEATURE:
<223> OTHER INFORMATION: siRNA target IL-11Ralpha

<400> SEQUENCE: 13
gctcaaggaa cgtgtgtaa                                                  19

<210> SEQ ID NO 14
<211> LENGTH: 54
<212> TYPE: DNA
<213> ORGANISM: Artificial Sequence
<220> FEATURE:
<223> OTHER INFORMATION: siRNA to IL-11
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine

<400> SEQUENCE: 14
ccuuccaaag ccagaucuun nnnnnnnnnn nnnaagaucu ggcuuuggaa ggnn          54

<210> SEQ ID NO 15
<211> LENGTH: 54
<212> TYPE: DNA
<213> ORGANISM: Artificial Sequence
<220> FEATURE:
<223> OTHER INFORMATION: siRNA to IL-11
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
```

```
<220> FEATURE:
<221> NAME/KEY: misc_feature
<222> LOCATION: (53)..(54)
<223> OTHER INFORMATION: N = deoxythymidine

<400> SEQUENCE: 15
gccugggcag gaacauauan nnnnnnnnnn nnnuauaugu uccugcccag gcnn      54

<210> SEQ ID NO 16
<211> LENGTH: 54
<212> TYPE: DNA
<213> ORGANISM: Artificial Sequence
<220> FEATURE:
<223> OTHER INFORMATION: siRNA to IL-11
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine

<400> SEQUENCE: 16
ccugggcagg aacauauaun nnnnnnnnnn nnnauauaug uuccugccca ggnn      54

<210> SEQ ID NO 17
<211> LENGTH: 54
<212> TYPE: DNA
<213> ORGANISM: Artificial Sequence
<220> FEATURE:
<223> OTHER INFORMATION: siRNA to IL-11
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine

<400> SEQUENCE: 17
gguucauuau ggcuguguun nnnnnnnnnn nnnaacacag ccauaaugaa ccnn      54

<210> SEQ ID NO 18
<211> LENGTH: 54
<212> TYPE: DNA
<213> ORGANISM: Artificial Sequence
<220> FEATURE:
<223> OTHER INFORMATION: siRNA to IL-11Ralpha
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine
```

```
<400> SEQUENCE: 18
ggaccauacc aaaggagaun nnnnnnnnnn nnnaucuccu uugguauggu ccnn          54

<210> SEQ ID NO 19
<211> LENGTH: 54
<212> TYPE: DNA
<213> ORGANISM: Artificial Sequence
<220> FEATURE:
<223> OTHER INFORMATION: siRNA to IL-11Ralpha
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine

<400> SEQUENCE: 19
gcgucuuugg gaauccuuun nnnnnnnnnn nnnaaaggau ucccaaagac gcnn          54

<210> SEQ ID NO 20
<211> LENGTH: 54
<212> TYPE: DNA
<213> ORGANISM: Artificial Sequence
<220> FEATURE:
<223> OTHER INFORMATION: siRNA to IL-11Ralpha
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine

<400> SEQUENCE: 20
gcaggacagu agaucccuan nnnnnnnnnn nnnuagggau cuacuguccu gcnn          54

<210> SEQ ID NO 21
<211> LENGTH: 54
<212> TYPE: DNA
<213> ORGANISM: Artificial Sequence
<220> FEATURE:
<223> OTHER INFORMATION: siRNA to IL-11Ralpha
<220> FEATURE:
<221> NAME/KEY: misc_feature
<222> LOCATION: (20)..(21)
<223> OTHER INFORMATION: N = deoxythymidine
<220> FEATURE:
<221> NAME/KEY: misc_feature
<222> LOCATION: (22)..(33)
<223> OTHER INFORMATION: n is a, c, g, t or u; up to 8 nucleotides may
      be absent
<220> FEATURE:
<221> NAME/KEY: misc_feature
<222> LOCATION: (53)..(54)
<223> OTHER INFORMATION: N = deoxythymidine

<400> SEQUENCE: 21
gcucaaggaa cguguguaan nnnnnnnnnn nnnuuacaca cguuccuuga gcnn          54
```

```
<210> SEQ ID NO 22
<211> LENGTH: 24
<212> TYPE: DNA
<213> ORGANISM: Artificial Sequence
<220> FEATURE:
<223> OTHER INFORMATION: IL-11 forward primer

<400> SEQUENCE: 22
aattcccagc tgacggagat caca                                              24

<210> SEQ ID NO 23
<211> LENGTH: 24
<212> TYPE: DNA
<213> ORGANISM: Artificial Sequence
<220> FEATURE:
<223> OTHER INFORMATION: IL-11 reverse primer

<400> SEQUENCE: 23
tctactcgaa gccttgtcag caca                                              24

<210> SEQ ID NO 24
<211> LENGTH: 20
<212> TYPE: DNA
<213> ORGANISM: Artificial Sequence
<220> FEATURE:
<223> OTHER INFORMATION: IL-11ra forward primer

<400> SEQUENCE: 24
cagcacgtcc tgaagtctcc                                                   20

<210> SEQ ID NO 25
<211> LENGTH: 20
<212> TYPE: DNA
<213> ORGANISM: Artificial Sequence
<220> FEATURE:
<223> OTHER INFORMATION: IL-11ra reverse primer

<400> SEQUENCE: 25
ggaagtaagg tagcgggtgg                                                   20

<210> SEQ ID NO 26
<211> LENGTH: 20
<212> TYPE: DNA
<213> ORGANISM: Artificial Sequence
<220> FEATURE:
<223> OTHER INFORMATION: TGFbeta1 forward primer

<400> SEQUENCE: 26
ccctatattt ggagcctgga                                                   20

<210> SEQ ID NO 27
<211> LENGTH: 20
<212> TYPE: DNA
<213> ORGANISM: Artificial Sequence
<220> FEATURE:
<223> OTHER INFORMATION: TGFbeta1 reverse primer

<400> SEQUENCE: 27
cttgcgaccc acgtagtaga                                                   20

<210> SEQ ID NO 28
<211> LENGTH: 20
<212> TYPE: DNA
<213> ORGANISM: Artificial Sequence
<220> FEATURE:
<223> OTHER INFORMATION: Col1a1 forward primer
```

<400> SEQUENCE: 28
ggggcaagac agtcatcgaa                                                  20

<210> SEQ ID NO 29
<211> LENGTH: 20
<212> TYPE: DNA
<213> ORGANISM: Artificial Sequence
<220> FEATURE:
<223> OTHER INFORMATION: Col1a1 reverse primer

<400> SEQUENCE: 29
gtccgaattc ctggtctggg                                                  20

<210> SEQ ID NO 30
<211> LENGTH: 20
<212> TYPE: DNA
<213> ORGANISM: Artificial Sequence
<220> FEATURE:
<223> OTHER INFORMATION: Col1a2 forward primer

<400> SEQUENCE: 30
cccagagtgg aacagcgatt                                                  20

<210> SEQ ID NO 31
<211> LENGTH: 20
<212> TYPE: DNA
<213> ORGANISM: Artificial Sequence
<220> FEATURE:
<223> OTHER INFORMATION: col1a2 reverse primer

<400> SEQUENCE: 31
atgagttctt cgctggggtg                                                  20

<210> SEQ ID NO 32
<211> LENGTH: 20
<212> TYPE: DNA
<213> ORGANISM: Artificial Sequence
<220> FEATURE:
<223> OTHER INFORMATION: Col3a1 forward primer

<400> SEQUENCE: 32
atgcccacag ccttctacac                                                  20

<210> SEQ ID NO 33
<211> LENGTH: 22
<212> TYPE: DNA
<213> ORGANISM: Artificial Sequence
<220> FEATURE:
<223> OTHER INFORMATION: Col3a1 reverse primer

<400> SEQUENCE: 33
accagttgga catgattcac ag                                               22

<210> SEQ ID NO 34
<211> LENGTH: 19
<212> TYPE: DNA
<213> ORGANISM: Artificial Sequence
<220> FEATURE:
<223> OTHER INFORMATION: FN1 forward primer

<400> SEQUENCE: 34
cacccgtgaa gaatgaaga                                                   19

```
<210> SEQ ID NO 35
<211> LENGTH: 19
<212> TYPE: DNA
<213> ORGANISM: Artificial Sequence
<220> FEATURE:
<223> OTHER INFORMATION: FN1 reverse primer

<400> SEQUENCE: 35
ggcaggagat tgttagga                                              19

<210> SEQ ID NO 36
<211> LENGTH: 20
<212> TYPE: DNA
<213> ORGANISM: Artificial Sequence
<220> FEATURE:
<223> OTHER INFORMATION: MMP2 forward primer

<400> SEQUENCE: 36
acaagtggtc cgcgtaaagt                                            20

<210> SEQ ID NO 37
<211> LENGTH: 20
<212> TYPE: DNA
<213> ORGANISM: Artificial Sequence
<220> FEATURE:
<223> OTHER INFORMATION: MMP2 reverse primer

<400> SEQUENCE: 37
aaacaaggct tcatgggggc                                            20

<210> SEQ ID NO 38
<211> LENGTH: 20
<212> TYPE: DNA
<213> ORGANISM: Artificial Sequence
<220> FEATURE:
<223> OTHER INFORMATION: TIMP-1 forward primer

<400> SEQUENCE: 38
gggctaaatt catgggttcc                                            20

<210> SEQ ID NO 39
<211> LENGTH: 20
<212> TYPE: DNA
<213> ORGANISM: Artificial Sequence
<220> FEATURE:
<223> OTHER INFORMATION: TIMP-1 reverse primer

<400> SEQUENCE: 39
ctgggacttg tgggcatatc                                            20

<210> SEQ ID NO 40
<211> LENGTH: 22
<212> TYPE: DNA
<213> ORGANISM: Artificial Sequence
<220> FEATURE:
<223> OTHER INFORMATION: IL6 forward primer

<400> SEQUENCE: 40
aggataccac tcccaacaga cc                                         22

<210> SEQ ID NO 41
<211> LENGTH: 23
<212> TYPE: DNA
<213> ORGANISM: Artificial Sequence
<220> FEATURE:
<223> OTHER INFORMATION: IL6 reverse primer
```

<400> SEQUENCE: 41
agtgcatcat cgttgttcat aca                                    23

<210> SEQ ID NO 42
<211> LENGTH: 24
<212> TYPE: DNA
<213> ORGANISM: Artificial Sequence
<220> FEATURE:
<223> OTHER INFORMATION: TNFalpha forward primer

<400> SEQUENCE: 42
ctcttctcaa aattcgagtg acaa                                   24

<210> SEQ ID NO 43
<211> LENGTH: 23
<212> TYPE: DNA
<213> ORGANISM: Artificial Sequence
<220> FEATURE:
<223> OTHER INFORMATION: TNFalpha reverse primer

<400> SEQUENCE: 43
tgggagtaga caaggtacaa ccc                                    23

<210> SEQ ID NO 44
<211> LENGTH: 20
<212> TYPE: DNA
<213> ORGANISM: Artificial Sequence
<220> FEATURE:
<223> OTHER INFORMATION: CCL2 forward primer

<400> SEQUENCE: 44
gaaggaatgg gtccagacat                                        20

<210> SEQ ID NO 45
<211> LENGTH: 20
<212> TYPE: DNA
<213> ORGANISM: Artificial Sequence
<220> FEATURE:
<223> OTHER INFORMATION: CCL2 reverse primer

<400> SEQUENCE: 45
acgggtcaac ttcacattca                                        20

<210> SEQ ID NO 46
<211> LENGTH: 20
<212> TYPE: DNA
<213> ORGANISM: Artificial Sequence
<220> FEATURE:
<223> OTHER INFORMATION: CCL5 forward primer

<400> SEQUENCE: 46
gctgctttgc ctacctctcc                                        20

<210> SEQ ID NO 47
<211> LENGTH: 21
<212> TYPE: DNA
<213> ORGANISM: Artificial Sequence
<220> FEATURE:
<223> OTHER INFORMATION: CCL5 reverse primer

<400> SEQUENCE: 47
tcgagtgaca aacacgactg c                                      21

TREATMENT OF SMC MEDIATED DISEASE

RELATED APPLICATIONS

The present application claims priority under 35 USC § 119(a)-(d) to United Kingdom Application No. 1716733.9, filed Oct. 12, 2017. The entire contents of the aforementioned application are hereby incorporated by reference herein.

FIELD OF THE INVENTION

The present invention relates to the diagnosis, treatment and prophylaxis of diseases and conditions associated with smooth muscle cell (SMC) dysfunction.

BACKGROUND TO THE INVENTION

Smooth muscle cell (SMC) dysfunction is observed in many diseases and conditions, in which a variety of upstream disease factors stimulate normal SMCs to aberrantly proliferate, become hypertrophic, migrate, de-differentiate and produce extracellular matrix.

SMCs having this disease-associated phenotype are referred to in the art variously as 'secretory SMCs' (see e.g. Rainger and Nash Circ Res 88 (6), 615-622 (2001)), 'synthetic SMCs' (see e.g. Beamish et al., Tissue Eng Part B Rev. (2010) 16(5): 467-491) and 'migratory SMCs' (see e.g. Sandison et al., J Physiol. (2016); 594(21):6189-6209). Herein, we refer to SMCs of this phenotype as 'secretory SMCs'.

Whilst diverse upstream factors result in SMC dysfunction, there are some common downstream factors that maintain the adverse, disease-associated, secretory SMC phenotype.

Diseases characterised by Vascular SMC (VSMC) dysfunction include atherosclerosis, hypertension, vascular aneurysms, vascular stenosis and restenosis, atherosclerosis, supravalvular stenosis, pulmonary artery hypertension, plexiform lesions, fibromuscular dysplasia, telangiectasia, among others. SMCs are components of many visceral organs and form the contractile apparatus of the esophagus, stomach, small bowel, large bowel, rectum, ureters and bladder. Abnormal function of SMCs in visceral organs can lead to achalasia, dysphagia, strictures of the bowel, pyloric stenosis, diarrhoea, constipation, diverticular disease, renal and bladder disease. SMCs also play an important role in lung function, and bronchial airway SMC mass and contractility are pathologically implicated in asthma, cystic fibrosis, COPD, ARDS and other respiratory conditions. SMC dysfunction in asthma is caused by changes in SMC phenotype and behavior in response to environmental and chemical cues such as chemokines, interleukins and other cytokines.

SUMMARY OF THE INVENTION

The present invention relates to the treatment of pathology associated with smooth muscle cell (SMC) activity (e.g. secretory SMC activity) through inhibition of IL-11-mediated signalling.

In one aspect, the present invention provides an agent capable of inhibiting interleukin 11 (IL-11)-mediated signalling for use in a method of treating or preventing a disease in which smooth muscle cells (SMCs) are pathologically implicated.

In another aspect, the present invention provides the use of an agent capable of inhibiting interleukin 11 (IL-11)-mediated signalling for use in the manufacture of a medicament for use in a method of treating or preventing a disease in which smooth muscle cells (SMCs) are pathologically implicated.

In another aspect, the present invention a method of treating or preventing a disease in which smooth muscle cells (SMCs) are pathologically implicated, the method comprising administering to a subject in need of treatment a therapeutically effective amount of an agent capable of inhibiting interleukin 11 (IL-11)-mediated signalling.

In accordance with various aspects of the present invention, in some embodiments the SMCs are secretory SMCs. Accordingly, in some embodiments the disease in which SMCs are pathologically implicated is a disease in which secretory SMCs are pathologically implicated. In accordance with various aspects of the present invention, the SMCs and/or secretory SMCs are vascular SMCs (VSMCs). Accordingly, in some embodiments the disease in which SMCs or secretory SMCs are pathologically implicated is a disease in which vascular SMCs (VSMCs) are pathologically implicated.

In accordance with various aspects of the present invention, in some embodiments the agent is an agent capable of binding to IL-11 or a receptor for IL-11. In some embodiments the agent is selected from the group consisting of: an antibody or an antigen-binding fragment thereof, a polypeptide, a peptide, an oligonucleotide, an aptamer or a small molecule. In some embodiments the agent is an antibody or antigen-binding fragment thereof. In some embodiments the agent is a decoy IL-11 receptor. In some embodiments the agent is capable of reducing the expression of IL-11 or a receptor for IL-11. In some embodiments the agent is an oligonucleotide or a small molecule.

In accordance with various aspects of the present invention, in some embodiments the disease is a disease of the cardiovascular system, the digestive system, the excretory system, the respiratory system, the renal system or the reproductive system. In some embodiments the disease in which SMCs are pathologically implicated is selected from the group consisting of: atherosclerosis, hypertension, vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, atherosclerosis, fibromuscular dysplasia (FMD), supravalvular stenosis, renal artery stenosis, pulmonary artery hypertension (PAH), plexiform lesions, fibromuscular dysplasia, telangiectasia, achalasia, dysphagia, diarrhoea, constipation, inflammatory bowel disease (IBD), coeliac disease, irritable bowel syndrome, Crohn's disease, ulcerative colitis, bowel stricture, diverticulosis, renal disease, focal and segmental glomerulosclerosis (FSGS), IgA nephropathy, crescentic glomerulonephritis, lupus nephritis, diabetic nephropathy (DN), bladder disease, lung disease, asthma, cystic fibrosis, chronic obstructive pulmonary disease (COPD), acute respiratory distress syndrome (ARDS), systemic sclerosis, Hutchinson-Gilford Progeria Syndrome (HGPS), leiomyoma, leiomyosarcoma and Hermansky-Pudlak Syndrome (HPS).

In accordance with various aspects of the present invention, in some embodiments the method of treating or preventing comprises administering the agent to a subject in which expression of IL-11 or a receptor for IL-11 is upregulated. In some embodiments the method of treating or preventing comprises administering the agent to a subject in expression of IL-11 or a receptor for IL-11 has been determined to be upregulated. In some embodiments the method of treating or preventing comprises determining whether expression of IL-11 or a receptor for IL-11 is upregulated in the subject and administering the agent to a subject in which expression of IL-11 or a receptor for IL-11 is upregulated.

In another aspect the present invention provides the use of an agent capable of inhibiting interleukin 11 (IL-11)-mediated signalling to inhibit smooth muscle cell (SMC) activity.

In another aspect the present invention provides a method for inhibiting the activity of smooth muscle cells (SMCs), the method comprising contacting SMCs with an agent capable of inhibiting interleukin 11 (IL-11)-mediated signalling.

In another aspect the present invention provides a method for inhibiting the activity of smooth muscle cells (SMCs) in a subject, the method comprising administering an agent capable of inhibiting interleukin 11 (IL-11)-mediated signalling to the subject.

In another aspect the present invention provides a method of determining the suitability of a subject for the treatment or prevention of a disease in which smooth muscle cells (SMCs) are pathologically implicated with an agent capable of inhibiting the action of Interleukin 11 (IL-11), the method comprising determining, optionally in vitro, whether IL-11 or an Interleukin 11 receptor (IL-11R) expression is upregulated in the subject.

In another aspect the present invention provides a method of selecting a subject for the treatment or prevention of a disease in which smooth muscle cells (SMCs) are pathologically implicated with an agent capable of inhibiting interleukin 11 (IL-11)-mediated signalling, the method comprising determining, optionally in vitro, whether expression of IL-11 or a receptor for IL-11 is upregulated in the subject.

In another aspect the present invention provides a method of diagnosing a disease in which smooth muscle cells (SMCs) are pathologically implicated or a risk of developing a disease in which smooth muscle cells (SMCs) are pathologically implicated in a subject, the method comprising determining, optionally in vitro, the upregulation of the expression of interleukin 11 (IL-11) or a receptor for IL-11 in a sample obtained from the subject. In some embodiments the method is a method of confirming a diagnosis of a disease in which SMCs are pathologically implicated in a subject suspected of having a disease in which SMCs are pathologically implicated. In some embodiments the method further comprises selecting the subject for treatment with an agent capable of inhibiting IL-11-mediated signalling.

In another aspect the present invention provides a method of providing a prognosis for a subject having, or suspected of having a disease in which smooth muscle cells (SMCs) are pathologically implicated, the method comprising determining, optionally in vitro, whether expression of interleukin 11 (IL-11) or a receptor for IL-11 is upregulated in a sample obtained from the subject and, based on the determination, providing a prognosis for treatment of the subject with an agent capable of inhibiting IL-11-mediated signalling. In some embodiments the method further comprises selecting a subject determined to have upregulated expression of expression of IL-11 or a receptor for IL-11 for treatment with an agent capable of inhibiting IL-11-mediated signalling.

In another aspect the present invention provides a method of diagnosing a disease in which smooth muscle cells (SMCs) are pathologically implicated or a risk of developing a disease in which smooth muscle cells (SMCs) are pathologically implicated in a subject, the method comprising determining, optionally in vitro, one or more genetic factors in the subject that are predictive of upregulation of expression of IL-11 or a receptor for IL-11, or of upregulation of IL-11 mediated signalling. In some embodiments the method is a method of confirming a diagnosis of a disease in which smooth muscle cells (SMCs) are pathologically implicated in a subject suspected of having a disease in which smooth muscle cells (SMCs) are pathologically implicated. In some embodiments the method further comprises selecting the subject for treatment with an agent capable of inhibiting IL-11-mediated signalling.

In another aspect the present invention provides a method of providing a prognosis for a subject having, or suspected of having, a disease in which smooth muscle cells (SMCs) are pathologically implicated, the method comprising determining, optionally in vitro, one or more genetic factors in the subject that are predictive of upregulation of expression of IL-11 or a receptor for IL-11, or of upregulation of IL-11 mediated signalling.

DESCRIPTION

Interleukin 11 and Receptors for IL-11

Interleukin 11 (IL-11), also known as adipogenesis inhibitory factor, is a pleiotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

Interleukin 11 (IL-11) is expressed in a variety of mesenchymal cell types[1]. IL-11 genomic sequences have been mapped onto chromosome 19 and the centromeric region of chromosome 7[1], and is transcribed with a canonical signal peptide that ensures efficient secretion from cells. The activator protein complex of IL-11, cJun/AP-1, located within its promoter sequence is critical for basal transcriptional regulation of IL-11[1]. The immature form of human IL-11 is a 199 amino acid polypeptide whereas the mature form of IL-11 encodes a protein of 178 amino acid residues (Garbers and Scheller., Biol. Chem. 2013; 394(9):1145-1161). The human IL-11 amino acid sequence is available under UniProt accession no. P20809 (P20809.1 GI:124294: SEQ ID NO:1). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. In preferred embodiments the species is human (*Homo sapiens*). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids IL-11 signals through a homodimer of the ubiquitously expressed glycoprotein 130 (gp130: also known as glycoprotein 130, IL-6ST, IL-6-beta or CD130). Gp130 is a transmembrane protein that forms one subunit of the type I cytokine receptor with the IL-6 receptor family. Specificity is gained through an individual IL-11 α-receptor (IL-11Rα), which does not directly participate in signal transduction, although the initial cytokine binding event to the α-receptor leads to the final complex formation with gp130.

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available under UniProt accession no. P40189-1 (SEQ ID NO:2).

Human IL-11Rα is a 422 amino acid polypeptide (UniProt 014626; SEQ ID NO:3) and shares ~85% nucleotide and amino acid sequence identity with the murine IL-11Rα (Du and Williams., Blood Vol, 89, No, 11, Jun. 1, 1997). Two isoforms of IL-11 Rα have been reported, which differ in the cytoplasmic domain (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

The receptor binding sites on murine IL-11 have been mapped and three sites—sites I, II and III-identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In this specification a receptor for IL-11 refers to a polypeptide or polypeptide complex capable of binding IL-11. In some embodiments an IL-11 receptor is capable of binding IL-11 and inducing signal transduction in cells expressing the receptor.

An IL-11 receptor may be from any species and includes isoforms, fragments, variants or homologues of an IL-11 receptor from any species. In preferred embodiments the species is human (Homo sapiens).

In some embodiments the IL-11 receptor may be IL-11Rα. In some embodiments a receptor for IL-11 may be a polypeptide complex comprising IL-11Rα. In some embodiments the IL-11 receptor may be a polypeptide complex comprising IL-11Rα and gp130. In some embodiments the IL-11 receptor may be gp130 or a complex comprising gp130 to which IL-11 binds.

Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

IL-11 Signalling

IL-11 binds to IL-11Rα with low affinity (Kd~10 nmol/L), and interaction between these binding partners alone is insufficient to transduce a biological signal. The generation of a high affinity receptor (Kd~400 to 800 pmol/L) capable of signal transduction requires co-expression of the IL-11 Rα and gp130 (Curtis et al (Blood 1997 Dec. 1; 90 (11): 4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and downstream signalling, predominantly through the mitogen-activated protein kinase (MAPK)-cascade and the Janus kinase/signal transducer and activator of transcription (Jak/STAT) pathway (Garbers and Scheller, supra).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11R) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R. Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be important for disease pathogenesis, yet it's role in human disease has not yet been studied.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα, termed "IL-11 cis signalling".

IL-11-mediated signalling has been shown to stimulate hematopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells[1].

The physiological role of Interleukin 11 (IL-11) remains unclear. IL-11 has been most strongly linked with activation of haematopoetic cells and with platelet production, but has also been suggested to be found to be pro-inflammatory as well as anti-inflammatory, pro-angiogenic and important for neoplasia. It is known that TGFβ1 or tissue injury can induce IL-11 expression (Zhu, M. et al. PLOS ONE 10, (2015); Yashiro, R. et al. J. Clin. Periodontol. 33, 165-71 (2006); Obana, M. et al. Circulation 121, 684-91 (2010); Tang, W et al. J. Biol. Chem. 273, 5506-13 (1998)).

IL-11 is an important post-transcriptional modulator of TGFβ-mediated signalling. TGFβ1 has been shown to stimulate the AP-1 promoter region of IL-11, and TGFβ-induced secretion of IL-11 has been shown to induce activation of ERK p42/44 and p38 MAP kinases in intestinal myofibroblasts (Bamba et al. Am J Physiol Gastrointest Liver Physiol. (2003) 285(3):G529-38). MAP kinase inhibitors are able to significantly reduce TGFβ-induced IL-11 secretion, and p38 MAP kinase-mediated stabilization of mRNA has been shown to be critical for TGFβ-induced secretion of IL-11.

As used herein, "IL-11 signalling" and "IL-11-mediated signalling" refers to signalling mediated by binding of IL-11, or a fragment thereof having the function of the mature IL-11 molecule, to a receptor for IL-11.

Smooth Muscle Cells (SMCs)

Smooth muscle cells (SMCs) are a type of mesenchymal cell found in many organs of the body. In the vascular system, vascular smooth muscle cells (VSMCs) form the medial layer of all large arteries and arterioles and are essential for maintaining vascular tone and blood pressure. SMCs are also found in many visceral organs, and form the contractile apparatus of the esophagus, stomach, small bowel, large bowel, rectum, ureters and bladder. SMCs are also found in airways of the respiratory system (e.g. of the lung).

In embodiments in accordance with the various aspects of the present invention, a smooth muscle cell (SMC) may be a vascular SMC (VSMC), an intestinal SMC (iSMC), an airway SMC (ASMC), an SMC from a blood vessel, artery, ateriole, a visceral organ, an organ of the digestive system, an organ of the urinary system, the esophagus, the stomach, the small intestine, the large intestine, the rectum, the ureter, the bladder, the kidney (e.g. a mesangial cell), an organ of the respiratory system, an airway, the trachea, lung, bronchi or bronchioles.

In embodiments in accordance with the various aspects of the present invention, a smooth muscle cell (SMC) may be a vascular SMC (VSMC), an intestinal SMC (iSMC), an SMC from a blood vessel, artery, ateriole, a visceral organ, an organ of the digestive system, an organ of the urinary system, the esophagus, the stomach, the small intestine, the large intestine, the rectum, the ureter, the bladder, the kidney (e.g. a mesangial cell). In embodiments the SMC is not an airway SMC (ASMC), or an SMC from an organ of the respiratory system, an airway, the trachea, lung, bronchi or bronchioles. In embodiments the SMC is not a vascular SMC (VSMC). In embodiments the SMC is not an intestinal SMC (iSMC). In embodiments the SMC is not one or more of the following: an SMC from a blood vessel, artery, ateriole, a visceral organ, an organ of the digestive system, an organ of the urinary system, the esophagus, the stomach, the small intestine, the large intestine, the rectum, the ureter, the bladder, the kidney (e.g. a mesangial cell).

Under normal physiological conditions SMCs have a contractile phenotype characterised e.g. by an elongate, spindle-shaped morphology in culture, and a low proliferative rate (Beamish et al., Tissue Eng Part B Rev (2010) 16(5):467-491; Rzucidlo (2009) Vascular 17(Suppl 1):S15-S20). The contractile phenotype may be further characterised by expression of e.g. myocardin, myosin 11, smoothelin, smooth muscle myosin heavy chain (SMMHC), alpha-smooth muscle actin (αSMA), SM22α, h1-calponin, h-caldesmon, α1β1, α7β1 integrins and/or the dystrophin-glycoprotein complex (DGPC) (Owens et al., Physiol Rev (2004) 84(3):767-801, Xie et al., Arteriosclerosis, Thrombosis, and Vascular Biology (2011) 31:1485-1494; Beamish et al., Tissue Eng Part B Rev (2010) 16(5):467-491; Rzucidlo (2009) Vascular 17(Suppl 1):S15-S20). Specific cellular markers characterize the contractile VSMC phenotype. αSMA and SM22α are early markers of developing SMCs while calponin, caldesmon, and SMMHC are late markers[3].

In response to certain genetic, mechanical, endocrine, inflammatory, lipid and neuro-humoral stimuli, contractile SMCs can be induced to undergo a phenotypic change to a 'secretory' phenotype (sometimes referred to as a 'synthetic' or 'migratory' phenotype) characterised by increased proliferative rate and migratory capacity, and expression and/or secretion of pro-inflammatory factors and extracellular matrix components (e.g. collagen 1).

Secretory SMCs display reduced expression of SMC-related genes for contractile proteins (e.g. myocardin, SM22α, SMMHC), and increased expression of osteopontin, l-caldesmon, nonmuscle myosin heavy chain B (NM-B MHC), vimentin, tropomyosin 4, and cellular-retinal binding-protein-1 (CRBP-1). Secretory SMCs have a decreased number of actin filaments, an increased number of secretory vesicles, increased cell size, "hill-and-valley" morphology in culture and increased expression of α4β1 integrin.

An SMC having a secretory phenotype (i.e. a secretory SMC) as referred to herein may be characterised by one or more of the following characteristics: expression of one or more proinflammatory factors; expression and/or secretion of one or more extracellular matrix components (e.g. collagen I); expression and/or secretion of IL-11; expression of one or more of osteopontin, l-caldesmon, nonmuscle myosin heavy chain B (NM-B MHC), vimentin, tropomyosin 4, and cellular-retinal binding-protein-1 (CRBP-1); secretory vesicles; "hill-and-valley" morphology in vitro culture; expression of α4β1 integrin. In some embodiments, a secretory SMC may be characterised by one or more of the following characteristics defined by reference to a comparable SMC of a non-secretory phenotype (e.g. a contractile SMC): increased rate of proliferation; increased rate of migration; increased expression of one or more proinflammatory factors; increased expression and/or secretion of one or more extracellular matrix components (e.g. collagen 1); increased expression and/or secretion of IL-11; increased expression of one or more of osteopontin, I-caldesmon, nonmuscle myosin heavy chain B (NM-B MHC), vimentin, tropomyosin 4, and cellular-retinal binding-protein-1 (CRBP-1); increased number of secretory vesicles; decreased number of actin filaments; increased expression of α4β1 integrin; reduced expression of one or more contractile proteins (e.g. myocardin, SM22α, SMMHC).

An SMC having a contractile phenotype (i.e. a contractile SMC) as referred to herein may be characterised by one or more of the following characteristics: expression of one or more of myocardin, myosin 11, smoothelin, smooth muscle myosin heavy chain (SMMHC), alpha-smooth muscle actin (αSMA), SM22α, h1-calponin, h-caldesmon, α1β1 integrin, α7β1 integrin and the dystrophin-glycoprotein complex (DGPC); actin filaments; and elongate, spindle-shaped morphology in in vitro culture. In some embodiments, a contractile SMC may be characterised by one or more of the following characteristics defined by reference to a comparable SMC of a non-contractile phenotype (e.g. a secretory SMC): decreased rate of proliferation; decreased rate of migration; decreased expression of one or more proinflammatory factors; decreased expression and/or secretion of one or more extracellular matrix components (e.g. collagen I); decreased expression and/or secretion of IL-11; decreased expression of one or more of osteopontin, 1-caldesmon, nonmuscle myosin heavy chain B (NM-B MHC), vimentin, tropomyosin 4, and cellular-retinal binding-protein-1 (CRBP-1); decreased number of secretory vesicles; increased number of actin filaments; decreased expression of α4β1 integrin; and increased expression of one or more of myocardin, myosin 11, smoothelin, SMMHC, αSMA, SM22α, h1-calponin, h-caldesmon, α1β1 integrin, α7β1 integrin or the dystrophin-glycoprotein complex (DGPC).

In some embodiments, a secretory SMC may have one or more of: decreased expression of SM22α as compared to a comparable SMC of a non-secretory phenotype (e.g. a contractile SMC), decreased expression of myocardin as compared to a comparable SMC of a non-secretory phenotype (e.g. a contractile SMC), increased expression and/or secretion of collagen as compared to a comparable SMC of a non-secretory phenotype (e.g. a contractile SMC) or increased expression and/or secretion of IL-11 as compared to a comparable SMC of a non-secretory phenotype (e.g. a contractile SMC). In some embodiments, a secretory SMC may display one or more of increased proliferation as compared to a comparable SMC of a non-secretory phenotype (e.g. a contractile SMC), increased migration, or increased invasion as compared to a comparable SMC of a non-secretory phenotype (e.g. a contractile SMC).

As used herein, a 'comparable SMC' may e.g. be derived from the same organ or tissue as the SMC with which the comparison is to be made.

As used herein, 'expression' may be gene expression or protein expression. Gene expression can be determined e.g. by detection of mRNA encoding the marker, for example by quantitative real-time PCR (qRT-PCR), or by reporter-based methods. Protein expression can be determined e.g. by detection of the protein, for example by antibody-based methods which are well known to the skilled person, such as western blot, immunohistochemistry, immunocytochemistry, flow cytometry, and ELISA. Protein expression can be determined by reporter-based methods, e.g. assays for a function of the protein.

Cell proliferation can be determined by analysing cell division over a period of time. Cell division can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

Cell migration can be analysed, for example, by in vitro analysis of wound closure in a scratch assay, e.g. as described in Example 9 and in Liang et al., Nat Protoc. (2007) 2(2):329-33, which is hereby incorporated by reference in its entirety. Cell migration can be analysed using Boyden chamber assays as described in Example 9 and in Chen, Methods Mol Biol. (2005) 294:15-22 which is hereby incorporated by reference in its entirety.

Aspects of the present invention involve inhibition of secretory SMC activity. That is, aspects of the present invention involve inhibiting (i.e. reducing the level of) a functional property of secretory SMCs.

In some embodiments the secretory SMC activity may be one or more of: proliferation, migration, invasion, expression and/or secretion of one or more extracellular matrix components (e.g. collagen I), expression and/or secretion of one or more matrix modifying enzymes (e.g. TIMP1), expression and/or secretion of one or more proinflammatory cytokines (e.g. TNFα), expression and/or secretion of IL-11 and expression of one or more proinflammatory factors.

Inhibition of secretory SMC activity may be achieved e.g. by inhibiting one or more activities of a secretory SMC, or by reducing the number of SMCs.

Inhibition of secretory SMC activity may be performed in vitro or in vivo. In some embodiments inhibition of one or more activities of a secretory SMC in a tissue, organ or subject. In some embodiments reduction of the number of secretory SMCs may be in a tissue, organ or subject.

TGFβ and IL-11 Signalling in SMCs

The role of TGFβ-mediated signalling in SMC phenotype switching is unclear. The role of IL-11-mediated signalling in SMC phenotype switching is not known.

In some experimental models TGFβ has been shown to promote a VSMC contractile phenotype and inhibit VSMC migration and proliferation[4], but in other studies, TGFβ has been shown to be crucial for SMC migration[5]. Specific perturbation of TGFβ signalling in genetic causes of vascular aneurysms of the ascending thoracic aorta are documented and well described in the literature (e.g. Loeys-Dietz syndrome (LDS) due to mutations in TGFBR1, TGFBR2, SMAD3, and TGFB2). In LDS and Marfan syndrome there is evidence of loss-of-function in the upstream TGFβ pathway, but paradoxical activation of downstream effectors.

Taki et al. Atherosclerosis (1999) 144(2):375-80 studied the role of IL-11 signalling in VSMCs. They found that TGFβ, IL-1A and TNFα stimulated IL-11 gene expression and protein production in VSMCs, which the authors proposed to have anti-atherosclerotic effects[5,6]. In another study, VSMCs cultured from healthy human aortas stimulated with bFGF, showed that IL-11 caused a concentration-dependent decrease in bFGF-induced VSMC proliferation. Attenuation of two NF-κB-dependent cytokines, IL-8 and IL-6, was attributed to IL-11 induced suppression of NF-κB in this mode[7].

In the experimental examples of the present disclosure the inventors identify TGFβ mediated signalling and IL-11-mediated signalling as being able to promote the switching of smooth muscle cells from the contractile phenotype to the secretory phenotype. IL-11-mediated signalling is shown to be a key downstream effector of TGFβ mediated signalling, and specific inhibition of IL-11-mediated signalling is shown to abrogate the effects of TGFβ.

Agents Capable of Inhibiting the Action of IL-11

Aspects of the present invention involve inhibition of IL-11-mediated signalling.

Herein, 'inhibition' refers to a reduction, decrease or lessening relative to a control condition. For example, inhibition of the action of IL-11 by an agent capable of inhibiting IL-11-mediated signalling refers to a reduction, decrease or lessening of the extent/degree of IL-11-mediated signalling in the absence of the agent, and/or in the presence of an appropriate control agent.

Inhibition may herein also be referred to as neutralisation or antagonism. That is, an agent capable of inhibiting IL-11-mediated signalling (e.g. interaction, signalling or other activity mediated by IL-11 or an IL-11-containing complex) may be said to be a 'neutralising' or 'antagonist' agent with respect to the relevant function or process. For example, an agent which is capable of inhibiting IL-11-mediated signalling may be referred to as an agent which is capable of neutralising IL-11-mediated signalling, or may be referred to as an antagonist of IL-11-mediated signalling.

The IL-11 signalling pathway offers multiple routes for inhibition of IL-11 signalling. An agent capable of inhibiting IL-11-mediated signalling may do so e.g. through inhibiting the action of one or more factors involved in, or necessary for, signalling through a receptor for IL-11.

For example, inhibition of IL-11 signalling may be achieved by disrupting interaction between IL-11 (or an IL-11 containing complex, e.g. a complex of IL-11 and IL-11Rα) and a receptor for IL-11 (e.g. IL-11Rα, a receptor complex comprising IL-11 Rα, gp130 or a receptor complex comprising IL-11Rα and gp130). In some embodiments, inhibition of IL-11-mediated signalling is achieved by inhibiting the gene or protein expression of one or more of e.g. IL-11, IL-11 Rα and gp130.

In embodiments, inhibition of IL-11-mediated signalling is achieved by disrupting IL-11-mediated cis signalling but not disrupting IL-11-mediated trans signalling, e.g. inhibition of IL-11-mediated signalling is achieved by inhibiting gp130-mediated cis complexes involving membrane bound IL-11 Rα. In embodiments, inhibition of IL-11-mediated signalling is achieved by disrupting IL-11-mediated trans signalling but not disrupting IL-11-mediated cis signalling, i.e. inhibition of IL-11-mediated signalling is achieved by inhibiting gp130-mediated trans signalling complexes such as IL-11 bound to soluble IL-11Rα or IL-6 bound to soluble IL-6R. In embodiments, inhibition of IL-11-mediated signalling is achieved by disrupting IL-11-mediated cis signalling and IL-11-mediated trans signalling. Any agent as described herein may be used to inhibit IL-11-mediated cis and/or trans signalling.

In other examples, inhibition of IL-11 signalling may be achieved by disrupting signalling pathways downstream of IL-11/IL-11Rα/gp130.

In some embodiments, the methods of the present invention employ agents capable of inhibiting JAK/STAT signalling. In some embodiments, agents capable of inhibiting JAK/STAT signalling are capable of inhibiting the action of JAK1, JAK2, JAK3, TYK2, STAT1, STAT2, STAT3, STAT4, STAT5A, STAT5B and/or STAT6. For example, agents may be capable of inhibiting activation of JAK/STAT proteins, inhibiting interaction of JAK or STAT proteins with cell surface receptors e.g. IL-11Rα or gp130, inhibiting phosphorylation of JAK proteins, inhibiting interaction between JAK and STAT proteins, inhibiting phosphorylation of STAT proteins, inhibiting dimerization of STAT proteins, inhibiting translocation of STAT proteins to the cell nucleus, inhibiting binding of STAT proteins to DNA, and/or promoting degradation of JAK and/or STAT proteins. In some embodiments, a JAK/STAT inhibitor is selected from Ruxolitinib (Jakafi/Jakavi; Incyte), Tofacitinib (Xeljanz/Jakvinus; NIH/Pfizer), Oclacitinib (Apoquel), Baricitinib (Olumiant: Incyte/Eli Lilly), Filgotinib (G-146034/GLPG-0634; Galapagos NV), Gandotinib (LY-2784544; Eli Lilly), Lestaurtinib (CEP-701; Teva), Momelotinib (GS-0387/CYT-387: Gilead Sciences), Pacritinib (SB1518; CTI), PF-04965842 (Pfizer), Upadacitinib (ABT-494; AbbVie), Peficitinib (ASP015K/JNJ-54781532; Astellas), Fedratinib (SAR302503; Celgene), Cucurbitacin I (JSI-124) and CHZ868.

In some embodiments, the methods of the present invention employ agents capable of inhibiting MAPK/ERK signalling. In some embodiments, agents capable of inhibiting MAPK/ERK signalling are capable of inhibiting the action of GRB2, inhibiting the action of RAF kinase, inhibiting the action of MEK proteins, inhibiting the activation of MAP3K/MAP2K/MAPK and/or Myc, and/or inhibiting the phosphorylation of STAT proteins. In some embodiments, agents capable of inhibiting ERK signalling are capable of inhibiting ERK p42/44. In some embodiments, an ERK inhibitor is selected from SCH772984, SCi, VX-11e and DEL-22379. In embodiments, an ERK inhibitor is selected from Sorafenib (Nexavar; Bayer/Onyx), SB590885, PLX4720, XL281, RAF265 (Novartis), Encorafenib (LGX818/Braftovi; Array BioPharma), Dabrafenib (Tafinlar: GSK), Vemuralenib (Zelboraf; Roche), Cobimetinib (Cotellic; Roche), CI-1040, PD0325901, Binimetinib (MEK162/MEKTOVI; Array BioPharma), Selumetinib (AZD6244; Array/AstraZeneca) and Trametinib (GSK1120212/Mekinist; Novartis).

Binding Agents

In some embodiments, agents capable of inhibiting IL-11-mediated signalling may bind to IL-11. In some embodiments, agents capable of inhibiting IL-11-mediated signalling may bind to a receptor for IL-11 (e.g. IL-11Rα, gp130, or a complex containing IL-11Rα and/or gp130). Binding of such agents may inhibit IL-11-mediated signalling by reducing/preventing the ability of IL-11 to bind to receptors for IL-11, thereby inhibiting downstream signalling. Binding of such agents may inhibit IL-11 mediated cis and/or trans-signalling by reducing/preventing the ability of IL-11 to bind to receptors for IL-11 e.g. IL-11 Rα and/or gp130, thereby inhibiting downstream signalling. Agents may bind to trans-signalling complexes such as IL-11 and soluble IL-11Rα and inhibit gp130-mediated signalling.

Agents capable of binding to IL-11/an IL-11 containing complex or a receptor for IL-11 may be of any kind, but in some embodiments the agent may be an antibody, an antigen-binding fragment thereof, a polypeptide, a peptide, a nucleic acid, an oligonucleotide, an aptamer or a small molecule. The agents may be provided in isolated or purified form, or may be formulated as a pharmaceutical composition or medicament.

Antibodies and Antigen-Binding Fragments

In some embodiments, an agent capable of binding to IL-11/an IL-11 containing complex or a receptor for IL-11 is an antibody, or an antigen-binding fragment thereof. In some embodiments, an agent capable of binding to IL-11/an IL-11 containing complex or a receptor for IL-11 is a polypeptide, e.g. a decoy receptor molecule. In some embodiments, an agent capable of binding to IL-11/an IL-11 containing complex or a receptor for IL-11 may be an aptamer.

In some embodiments, an agent capable of binding to IL-11/an IL-11 containing complex or a receptor for IL-11 is an antibody, or an antigen-binding fragment thereof. An "antibody" is used herein in the broadest sense, and encompasses monoclonal antibodies, polyclonal antibodies, monospecific and multispecific antibodies (e.g., bispecific antibodies), and antibody fragments, as long as they display binding to the relevant target molecule.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799). Monoclonal antibodies (mAbs) are particularly useful in the methods of the invention, and are a homogenous population of antibodies specifically targeting a single epitope on an antigen.

Polyclonal antibodies are also useful in the methods of the invention. Monospecific polyclonal antibodies are preferred. Suitable polyclonal antibodies can be prepared using methods well known in the art.

Antigen-binding fragments of antibodies, such as Fab and $Fab_2$ fragments may also be used/provided as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

Antibodies and antigen-binding fragments according to the present disclosure comprise the complementarity-determining regions (CDRs) of an antibody which is capable of binding to the relevant target molecule (i.e. IL-11/an IL-11 containing complex/a receptor for IL-11).

Antibodies capable of binding to IL-11 include e.g. monoclonal mouse anti-human IL-11 antibody clone #22626: Catalog No. MAB218 (R&D Systems, MN, USA), used e.g. in Bockhorn et al. Nat. Commun. (2013) 4(0):1393, clone 6D9A (Abbiotec), clone KT8 (Abbiotec), clone M3103F11 (BioLegend), clone 1F1 (Abnova Corporation), clone 3C6 (Abnova Corporation), clone GF1 (LifeSpan Biosciences), clone 13455 (Source BioScience) and anti-IL-11 antibodies disclosed in US 2009/0202533 A1, WO 99/59608 A2, and WO 2018/109174 A2.

Antibodies capable of binding to IL-11 Rα include e.g. monoclonal antibody clone 025 (Sino Biological), clone EPR5446 (Abcam), clone 473143 (R & D Systems), clones 8E2 and 8E4 described in US 2014/0219919 A1, the monoclonal antibodies described in Blanc et al (J. Immunol Methods. 2000 Jul. 31; 241(1-2); 43-59), antibodies disclosed in WO 2014121325 A1 and US 2013/0302277 A1, and anti-IL-11Rα antibodies disclosed in US 2009/0202533 A1, WO 99/59608 A2, and WO 2018/109170 A2.

The antibodies/fragments may be antagonist antibodies/fragments that inhibit or reduce a biological activity of IL-11. The antibodies/fragments may be neutralising antibodies that neutralise the biological effect of IL-11, e.g. its ability to stimulate productive signalling via an IL-11 receptor. Neutralising activity may be measured by ability to neutralise IL-11 induced proliferation in the T11 mouse plasmacytoma cell line (Nordan, R. P. et al. (1987) J. Immunol. 139:813).

Antibodies generally comprise six CDRs; three in the light chain variable region (VL): LC-CDR1, LC-CDR2, LC-CDR3, and three in the heavy chain variable region (VH): HC-CDR1, HC-CDR2 and HC-CDR3. The six CDRs together define the paratope of the antibody, which is the part of the antibody which binds to the target molecule. There are several different conventions for defining antibody CDRs, such as those described in Kabat et al., Sequences of Proteins of Immunological Interest, 5th Ed. Public Health Service, National Institutes of Health, Bethesda, Md. (1991), Chothia et al., J. Mol. Biol. 196:901-917 (1987), and VBASE2, as described in Retter et al., Nucl. Acids Res. (2005) 33 (suppl 1): D671-D674.

Antibodies and antigen-binding fragments according to the present disclosure may be designed and prepared using the sequences of monoclonal antibodies (mAbs) capable of binding to the relevant target molecule. Antigen-binding regions of antibodies, such as single chain variable fragment (scFv), Fab and $Fab_2$ fragments may also be used/provided. An 'antigen-binding region' is any fragment of an antibody which is capable of binding to the target for which the given antibody is specific.

In some embodiments the antibodies/fragments comprise the VL and VH regions of an antibody which is capable of binding to IL-11, an IL-11 containing complex, or a receptor for IL-11. The VL and VH region of an antigen-binding region of an antibody together constitute the Fv region. In some embodiments the antibodies/fragments comprise or consist of the Fv region of an antibody which is capable of binding to IL-11, an IL-11 containing complex, or a receptor for IL-11. The Fv region may be expressed as a single chain wherein the VH and VL regions are covalently linked, e.g. by a flexible oligopeptide. Accordingly, antibodies/fragments may comprise or consist of an scFv comprising the VL and VH regions of an antibody which is capable of binding to IL-11, an IL-11 containing complex, or a receptor for IL-11.

The VL and light chain constant (CL) region, and the VH region and heavy chain constant 1 (CH1) region of an antigen-binding region of an antibody together constitute the Fab region. In some embodiments the antibodies/fragments comprise or consist of the Fab region of an antibody which is capable of binding to IL-11, an IL-11 containing complex, or a receptor for IL-11.

In some embodiments, antibodies/fragments comprise, or consist of, whole antibody capable of binding to IL-11, an IL-11 containing complex, or a receptor for IL-11. A "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety. Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies capable of binding to IL-11, an IL-11 containing complex, or a receptor for IL-11 may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Bio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies/fragments include bi-specific antibodies, e.g. composed of two different fragments of two different antibodies, such that the bi-specific antibody binds two types of antigen. The bispecific antibody comprises a antibody/fragment as described herein capable of binding to IL-11, an IL-11 containing complex, or a receptor for IL-11. The antibody may contain a different fragment having affinity for a second antigen, which may be any desired antigen. Techniques for the preparation of bi-specific antibodies are well known in the art, e.g. see Mueller, D et al., (2010 *Biodrugs* 24 (2): 89-98), Wozniak-Knopp G et al., (2010 *Protein Eng Des* 23 (4): 289-297. Baeuerle, P A et al., (2009 *Cancer Res* 69 (12): 4941-4944). Bispecific antibodies and bispecific antigen-binding fragments may be provided in any suitable format, such as those formats described in Kontermann MAbs 2012, 4(2): 182-197, which is hereby incorporated by reference in its entirety. For example, a bispecific antibody or bispecific antigen-binding fragment may be a bispecific antibody conjugate (e.g. an IgG2, F(ab')2 or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (db), dsDb, DART, scDb, tandAbs, tandem scFv (taFv), tandem dAb/VHH, triple body, triple head, Fab-scFv, or F(ab')$_2$-scFv$_2$), a bispecific Fc and C$_H$3 fusion protein (e.g. a taFv-Fc, Di-diabody, scDb-C$_H$3, scFv-Fc-scFv, HCAb-VHH, scFv-kih-Fc, or scFv-kih-C$_H$3), or a bispecific fusion protein (e.g. a scFv$_2$-albumin, scDb-albumin. taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

Methods for producing bispecific antibodies include chemically crosslinking antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen-binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339.

For example, a DNA construct encoding the light and heavy chain variable domains for the two antigen binding domains (i.e. the light and heavy chain variable domains for the antigen binding domain capable of binding to IL-11, an IL-11 containing complex, or a receptor for IL-11, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Decoy Receptors

Peptide or polypeptide based agents capable of binding to IL-11 or IL-11 containing complexes may be based on the IL-11 receptor, e.g. an IL-11 binding fragment of an IL-11 receptor.

In some embodiments, the binding agent may comprise an IL-11-binding fragment of the IL-11Rα chain, and may preferably be soluble and/or exclude one or more, or all, of the transmembrane domain(s). In some embodiments, the binding agent may comprise an IL-11-binding fragment of gp130, and may preferably be soluble and/or exclude one or more, or all, of the transmembrane domain(s). Such molecules may be described as decoy receptors.

Curtis et al (Blood 1997 Dec. 1; 90 (11):4403-12) report that a soluble murine IL-11 receptor alpha chain (sIL-11R) was capable of antagonizing the activity of IL-11 when tested on cells expressing the transmembrane IL-11R and gp130. They proposed that the observed IL-11 antagonism by the sIL-11R depends on limiting numbers of gp130 molecules on cells already expressing the transmembrane IL-11R.

The use of soluble decoy receptors as the basis for inhibition of signal transduction and therapeutic intervention has also been reported for other signalling molecule:receptor pairs, e.g. VEGF and the VEGF receptor (De-Chao Yu et al., Molecular Therapy (2012); 20 5, 938-947; Konner and Dupont Clin Colorectal Cancer 2004 October; 4 Suppl 2:S81-5).

As such, in some embodiments a binding agent may be a decoy receptor, e.g. a soluble receptor for IL-11 and/or IL-11 containing complexes. Competition for IL-11 and/or IL-11 containing complexes provided by a decoy receptor has been reported to lead to IL-11 antagonist action (Curtis et al., supra). Decoy IL-11 receptors are also described in WO 2017/103108 A1 and WO 2018/109168 A1, which are hereby incorporated by reference in their entirety.

Decoy IL-11 receptors preferably bind IL-11 and/or IL-11 containing complexes, and thereby make these species unavailable for binding to gp130, IL-11Rα and/or gp130: IL-11Rα receptors. As such, they act as 'decoy' receptors for IL-11 and IL-11 containing complexes, much in the same way that etanercept acts as a decoy receptor for TNFα. IL-11-mediated signalling is reduced as compared to the level of signalling in the absence of the decoy receptor.

Decoy IL-11 receptors preferably bind to IL-11 through one or more cytokine binding modules (CBMs). The CBMs are, or are derived from or homologous to, the CBMs of naturally occurring receptor molecules for IL-11. For example, decoy IL-11 receptors may comprise, or consist of, one or more CBMs which are from, are derived from or homologous to the CBM of gp130 and/or IL-11Rα.

In some embodiments, a decoy IL-11 receptor may comprise, or consist of, an amino acid sequence corresponding to the cytokine binding module of gp130. In some embodiments, a decoy IL-11 receptor may comprise an amino acid sequence corresponding to the cytokine binding module of IL-11Rα. Herein, an amino acid sequence which 'corresponds' to a reference region or sequence of a given peptide/polypeptide has at least 60%, e.g. one of at least 65%, 70%, 75%, 80%, 85%, 90%, 91%, 92%, 93%, 94%. 95%, 96%, 97%, 98% or 99% sequence identity to the amino acid sequence of the reference region/sequence.

In some embodiments a decoy receptor may be able to bind IL-11, e.g. with binding affinity of at least 100 μM or less, optionally one of 10 μM or less, 1 μM or less, 100 nM or less, or about 1 to 100 nM. In some embodiments a decoy receptor may comprise all or part of the IL-11 binding domain and may optionally lack all or part of the transmembrane domains. The decoy receptor may optionally be fused to an immunoglobulin constant region, e.g. IgG Fc region.

Inhibitors

The present invention contemplates the use of inhibitor molecules capable of binding to one or more of IL-11, an IL-11 containing complex, IL-11Rα, gp130, or a complex containing IL-11Rα and/or gp130, and inhibiting IL-11 mediated signalling.

In some embodiments the agent is a peptide or polypeptide based binding agents based on IL-11, e.g. mutant, variant or binding fragment of IL-11. Suitable peptide or polypeptide based agents may bind to a receptor for IL-11 (e.g. IL-11Rα, gp130, or a complex containing IL-11Rα and/or gp130) in a manner that does not lead to initiation of signal transduction, or which produces sub-optimal signaling. IL-11 mutants of this kind may act as competitive inhibitors of endogenous IL-11.

For example, W147A is an IL-11 antagonist in which the amino acid 147 is mutated from a tryptophan to an alanine, which destroys the so-called 'site III' of IL-11. This mutant can bind to IL-11Rα, but engagement of the gp130 homodimer fails, resulting in efficient blockade of IL-11 signalling (Underhill-Day et al., 2003; Endocrinology 2003 August; 144(8):3406-14). Lee et al (Am J respire Cell Mol Biol. 2008 December; 39(6):739-746) also report the generation of an IL-11 antagonist mutant (a "mutein") capable of specifically inhibiting the binding of IL-11 to IL-11Rα. IL-11 muteins are also described in WO 2009/052588 A1.

Menkhorst et al (Biology of Reproduction May 1, 2009 vol. 80 no. 5 920-927) describe a PEGylated IL-11 antagonist, PEGIL11A (CSL Limited, Parkvill, Victoria, Australia) which is effective to inhibit IL-11 action in female mice.

Pasqualini et al. Cancer (2015) 121(14):2411-2421 describe a ligand-directed, peptidomimetic drug, bone metastasis-targeting peptidomimetic-11 (BMTP-11) capable of binding to IL-11Rα.

In some embodiments a binding agent capable of binding to a receptor for IL-11 may be provided in the form of a small molecule inhibitor of one of IL-11Rα, gp130, or a complex containing IL-11Rα and/or gp130. In some embodiments a binding agent may be provided in the form of a small molecule inhibitor of IL-11 or an IL-11 containing complex, e.g. IL-11 inhibitor described in Lay et al., Int. J. Oncol. (2012); 41(2): 759-764, which is hereby incorporated by reference in its entirety.

Aptamers

In some embodiments, an agent capable of binding to IL-11/an IL-11 containing complex or a receptor for IL-11 (e.g. IL-11Rα, gp130, or a complex containing IL-11Rα and/or gp130) is an aptamer. Aptamers, also called nucleic acid/peptide ligands, are nucleic acid or peptide molecules characterised by the ability to bind to a target molecule with high specificity and high affinity. Almost every aptamer identified to date is a non-naturally occurring molecule.

Aptamers to a given target (IL-11, an IL-11 containing complex or a receptor for IL-11) may be identified and/or produced by the method of Systematic Evolution of Ligands by EXponential enrichment (SELEX™), or by developing SOMAmers (slow off-rate modified aptamers) (Gold L et al. (2010) PLoS ONE 5(12):e15004). Aptamers and SELEX are described in Tuerk and Gold, Science (1990) 249(4968): 505-10, and in WO 91/19813. Applying the SELEX and the SOMAmer technology includes for instance adding functional groups that mimic amino acid side chains to expand the aptamer's chemical diversity. As a result high affinity aptamers for a target may be enriched and identified.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesised by methods which are well known to the skilled person. For example, aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992). Tetrahedron 48 (12): 2223).

Suitable nucleic acid aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Suitable nucleic acid aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Suitable nucleic acid aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Aptamers may be peptides selected or engineered to bind specific target molecules. Peptide aptamers and methods for their generation and identification are reviewed in Reverdatto et al., Curr Top Med Chem. (2015) 15(12):1082-101, which is hereby incorporated by reference in its entirety. Peptide aptamers may optionally have a minimum length of one of 2, 3, 4, 5, 6, 7, 8, 9 or 10 amino acids. Peptide aptamers may optionally have a maximum length of one of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. Suitable peptide aptamers may optionally have a length of one of 2-30, 2-25, 2-20, 5-30, 5-25 or 5-20 amino acids.

Aptamers may have $K_d$'s in the nM or pM range, e.g. less than one of 500 nM, 10 nM, 50 nM, 10 nM, 1 nM. 500 pM, 100 pM.

Properties of IL-11 Binding Agents

Agents capable of binding to IL-11/an IL-11 containing complex or a receptor for IL-11 according to the present invention may exhibit one or more of the following properties:

Specific binding to IL-11/IL-11 containing complex or a receptor for IL-11;
Binding to IL-11/IL-11 containing complex, or a receptor for IL-11, with a $K_D$ of 10 µM or less, preferably one of ≤5 µM≤1 µM, ≤100 nM, ≤10 nM, ≤1 nM or ≤100 µM;
Inhibition of interaction between IL-11 and IL-11Rα;
Inhibition of interaction between IL-11 and gp130;
Inhibition of interaction between IL-11 and IL-11Rα: gp130 receptor complex;
Inhibition of interaction between IL-11:IL-11Rα complex and gp130.

These properties can be determined by analysis of the relevant agent in a suitable assay, which may involve comparison of the performance of the agent to suitable control agents. The skilled person is able to identify an appropriate control conditions for a given assay.

For example, a suitable negative control for the analysis of the ability of a test antibody/antigen-binding fragment to bind to IL-11/an IL-11 containing complex/a receptor for IL-11 may be an antibody/antigen-binding fragment directed against a non-target protein (i.e. which is not specific for IL-11/an IL-11 containing complex/a receptor for IL-11). A suitable positive control may be a known, validated (e.g. commercially available) IL-11- or IL-11 receptor-binding antibody. Controls may be of the same isotype as the putative IL-11/IL-11 containing complex/IL-11 receptor-binding antibody/antigen-binding fragment being analysed, and may e.g. have the same constant regions.

In some embodiments, the agent may be capable of binding specifically to IL-11 or an IL-11 containing complex, or a receptor for IL-11 (e.g. IL-11Rα, gp130, or a complex containing IL-11 Rα and/or gp130). An agent which specifically binds to a given target molecule preferably binds the target with greater affinity, and/or with greater duration than it binds to other, non-target molecules.

In some embodiments the agent may bind to IL-11 or an IL-11 containing complex with greater affinity than the affinity of binding to one or more other members of the IL-6 cytokine family (e.g. IL-6, leukemia inhibitory factor (LIF), oncostatin M (OSM), cardiotrophin-1 (CT-1), ciliary neurotrophic factor (CNTF), and cardiotrophin-like cytokine (CLC)). In some embodiments the agent may bind to a receptor for IL-11 (e.g. IL-11 Rα, gp130, or a complex containing IL-11Rα and/or gp130) with greater affinity than the affinity of binding to one or more other members of the IL-6 receptor family. In some embodiments the agent may bind with greater affinity to IL-11Rα than the affinity of binding to one or more of IL-6Rα, leukemia inhibitory factor receptor (LIFR), oncostatin M receptor (OSMR) and ciliary neurotrophic factor receptor alpha (CNTFRα).

In some embodiments, the extent of binding of a binding agent to a non-target is less than about 10% of the binding of the agent to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the binding agent binds to IL-11, an IL-11 containing complex or a receptor for IL-11 with a $K_D$ that is at least 0.1 order of magnitude (i.e. $0.1 \times 10^n$, where n is an integer representing the order of magnitude) greater than the $K_D$ towards another, non-target molecule. This may optionally be one of at least 0.2, 0.3, 0.4, 0.5, 0.6, 0.7, 0.8, 0.9, 1.0, 1.5, or 2.0.

Binding affinity for a given binding agent for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442; or Rich et al., Anal Biochem. 2008 Feb. 1; 373(1):112-20), Bio-Layer Interferometry (see e.g. Lad et al., (2015) J Biomol Screen 20(4): 498-507; or Concepcion et al., Comb Chem High Throughput Screen. 2009 September: 12(8): 791-800), MicroScale Thermophoresis (MST) analysis (see e.g. Jerabek-Willemsen et al., Assay Drug Dev Technol. 2011 August; 9(4): 342-353), or by a radiolabelled antigen binding assay (RIA).

In some embodiments, the agent is capable of binding to IL-11 or an IL-11 containing complex, or a receptor for IL-11 with a $K_D$ of 50 µM or less, preferably one of ≤10 µM, ≤5 µM, ≤4 µM, ≤3 µM, ≤2 µM, ≤1 µM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, 58 nM, ≤7 nM, ≤6 nM, ≤5 nM, ≤4 nM 53 nM, ≤2 nM, ≤1 nM, ≤500 µM, ≤400 µM, ≤300 µM, ≤200 µM, or ≤100 µM.

In some embodiments, the agent binds to IL-11, an IL-11 containing complex or a receptor for IL-11 with an affinity of binding (e.g. as determined by ELISA) of EC50=10,000 ng/ml or less, preferably one of ≤5,000 ng/ml, ≤1000 ng/ml, ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml. Such ELISAs can be performed e.g. as described in Antibody Engineering, vol. 1 ($2^{nd}$ Edn), Springer Protocols, Springer (2010), Part V, pp 657-665.

In some embodiments, the agent binds to IL-11 or an IL-11-containing complex in a region which is important for binding to a receptor for the IL-11 or IL-11-containing complex, e.g. gp130 or IL-11 Rα, and thereby inhibits interaction between IL-11 or an IL-11-containing complex and a receptor for IL-11, and/or signalling through the receptor. In some embodiments, the agent binds to a receptor for IL-11 in a region which is important for binding to IL-11 or an IL-11-containing complex, and thereby inhibits interaction between IL-11 or an IL-11-containing complex and a receptor for IL-11, and/or signalling through the receptor.

The ability of a given binding agent (e.g. an agent capable of binding IL-11/an IL-11 containing complex or a receptor for IL-11) to inhibit interaction between two proteins can be determined for example by analysis of interaction in the presence of, or following incubation of one or both of the interaction partners with, the binding agent. An example of a suitable assay to determine whether a given binding agent is capable of inhibiting interaction between two interaction partners is a competition ELISA.

An binding agent which is capable of inhibiting a given interaction (e.g. between IL-11 and IL-11Rα, or between IL-11 and gp130, or between IL-11 and IL-11Rα:gp130, or between IL-11:IL-11Rα and gp130) is identified by the observation of a reduction/decrease in the level of interaction between the interaction partners in the presence of—or following incubation of one or both of the interaction partners with—the binding agent, as compared to the level of interaction in the absence of the binding agent (or in the presence of an appropriate control binding agent). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the binding agent may be labelled or used in conjunction with a detectable entity for the purposes of detecting and/or measuring the level of interaction. For example, the agent may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding agent may be directly labelled with a detectable label or it may be indirectly labelled. For example, the binding agent may be unlabelled, and detected by another binding agent which is itself labelled. Alternatively, the second binding agent may have bound to it biotin and binding of labelled streptavidin to the biotin may be used to indirectly label the first binding agent.

Ability of a binding agent to inhibit interaction between two binding partners can also be determined by analysis of the downstream functional consequences of such interaction, e.g. IL-11-mediated signalling. For example, downstream functional consequences of interaction between IL-11 and IL-11Rα:gp130 or between IL-11:IL-11Rα and gp130 may include e.g. a process mediated by IL-11, myofibroblast generation from fibroblasts, proliferation or migration by secretory SMCs, or gene/protein expression of e.g. collagen or IL-11.

The ability of a binding agent to inhibit interaction between IL-11 or an IL-11 containing complex and a receptor for IL-11 can, for example, be analysed by stimulating fibroblasts with TGFβ1, incubating the cells in the presence of the binding agent and analysing the proportion of cells having αSMA-positive phenotype after a defined period of time. In such examples, inhibition of interaction between IL-11 or an IL-11 containing complex and a receptor for IL-11 can be identified by observation of a lower proportion of cells having an αSMA-positive phenotype as compared to positive control condition in which cells are treated with TGFβ1 in the absence of the binding agent (or in the presence of an appropriate control binding agent), or in the presence of an appropriate control binding agent. Such assays are also suitable for analysing the ability of a binding agent to inhibit IL-11-mediated signalling. Inhibition of interaction between IL-11 or an IL-11 containing complex and a receptor for IL-11 can also be analysed using $^3$H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

In some embodiments, the binding agent may be capable of inhibiting interaction between IL-11 and IL-11Rα to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the binding agent (or in the presence of an appropriate control binding agent). In some embodiments, the binding agent may be capable of inhibiting interaction between IL-11 and IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11 Rα in the absence of the binding agent (or in the presence of an appropriate control binding agent).

In some embodiments, the binding agent may be capable of inhibiting interaction between IL-11 and gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the binding agent (or in the presence of an appropriate control binding agent). In some embodiments, the binding agent may be capable of inhibiting interaction between IL-11 and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the binding agent (or in the presence of an appropriate control binding agent).

In some embodiments, the binding agent may be capable of inhibiting interaction between IL-11 and IL-11Rα:gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the binding agent (or in the presence of an appropriate control binding agent). In some embodiments, the binding agent may be capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα:gp130 in the absence of the binding agent (or in the presence of an appropriate control binding agent).

In some embodiments, the binding agent may be capable of inhibiting interaction between IL-11:IL-11Rα complex and gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the binding agent (or in the presence of an appropriate control binding agent). In some embodiments, the binding agent is capable of inhibiting interaction between IL-11:IL-11 Rα complex and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the binding agent.

Agents Capable of Reducing Expression of IL-11 or an IL-11 Receptor

In aspects of the present invention the agent capable of inhibiting IL-11-mediated signalling may be provided capable of preventing or reducing the expression of one or more of IL-11, IL-11Rα or gp130.

Expression may be gene or protein expression, and may be determined as described herein. Expression may be by a cell/tissue/organ/organ system of a subject. For example, expression may be prevented/reduced in smooth muscle cells.

Suitable agents may be of any kind, but in some embodiments an agent capable of preventing or reducing the expression of one or more of IL-11, IL-11Rα or gp130 may be a small molecule or an oligonucleotide.

An agent capable of preventing or reducing of the expression of one or more of IL-11, IL-11 Rα or gp130 may do so e.g. through inhibiting transcription of the gene encoding IL-11, IL-11Rα or gp130, inhibiting post-transcriptional processing of RNA encoding IL-11, IL-11 Rα or gp130, reducing the stability of RNA encoding IL-11, IL-11Rα or gp130, promoting degradation of RNA encoding IL-11, IL-11Rα or gp130, inhibiting post-translational processing of IL-11, IL-11Rα or gp130 polypeptide, reducing the stability of IL-11, IL-11Rα or gp130 polypeptide or promoting degradation of IL-11, IL-11Rα or gp130 polypeptide.

Taki et al. Clin Exp Immunol (1998) April; 112(1): 133-138 reported a reduction in the expression of IL-11 in rheumatoid synovial cells upon treatment with indomethacin, dexamethasone or interferon-gamma (IFNγ).

The present invention contemplates the use of antisense nucleic acid to prevent/reduce expression of IL-11, IL-11Rα or gp130. In some embodiments, an agent capable of preventing or reducing the expression of IL-11, IL-11 Rα or gp130 may cause reduced expression by RNA interference (RNAi).

In some embodiments, the agent may be an inhibitory nucleic acid, such as antisense or small interfering RNA, including but not limited to shRNA or siRNA.

In some embodiments the inhibitory nucleic acid is provided in a vector. For example, in some embodiments the agent may be a lentiviral vector encoding shRNA for one or more of IL-11, IL-11Rα or gp130.

Oligonucleotide molecules, particularly RNA, may be employed to regulate gene expression. These include antisense oligonucleotides, targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single-stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for IL-11, IL-11Rα and gp130 (e.g. the known mRNA sequences available from GenBank under Accession No.s: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 G1:254281268 (mouse IL-11Rα), NM_139116.1 GI:20806172 (rat IL-11Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the IL-11, IL-11Rα or gp130 mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of expression of IL-11, IL-11Rα or gp130 will preferably result in a decrease in the quantity of IL-11, IL-11 Rα or gp130 expressed by a cell/tissue/organ/organ system/subject. For example, in a given cell the repression of IL-11, IL-11Rα or gp130 by administration of a suitable nucleic acid will result in a decrease in the quantity of IL-11, IL-11 Rα or gp130 expressed by that cell relative to an untreated cell.

Repression may be partial. Preferred degrees of repression are at least 50%, more preferably one of at least 60%, 70%, 80%, 85% or 90%. A level of repression between 90% and 100% is considered a 'silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5 overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of IL-11, IL-11Rα or gp130. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of IL-11, IL-11 Rα or gp130.

In one embodiment, the siRNA, longer dsRNA or miRNA is produced endogenously (within a cell) by transcription from a vector. The vector may be introduced into the cell in any of the ways known in the art.

Optionally, expression of the RNA sequence can be regulated using a tissue specific (e.g. heart, liver, kidney or eye specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of IL-11, IL-11 Rα or gp130 repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long term expression of the therapeutic oligonucleotide. Examples include lentiviral (Nature 2009 Jan. 22; 457 (7228):426-433), adenovirus (Shen et al., FEBS Lett 2003 Mar. 27; 539(1-3)111-4) and retroviruses (Barton and Medzhitov PNAS Nov. 12, 2002 vol. 99, no.23 14943-14945).

In other embodiments a vector may be configured to assist delivery of the therapeutic oligonucleotide to the site at which repression of IL-11, IL-11Rα or gp130 expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations (Wang et al., AAPS J. 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R; P(O)OR6; CO; or CONR'2 wherein R is H (or a salt) or alkyl (1-12C) and R6 is alkyl (1-9C) is joined to adjacent nucleotides through-O-or-S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3'position and other than a phosphate group at the 5'position. Thus modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine,5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methylthio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6, diaminopurine, methylpsuedouracil, 1-methylguanine, 1-methylcytosine.

Methods relating to the use of RNAi to silence genes in *C. elegans, Drosophila*, plants, and mammals are known in the art (Fire A, et al., 1998 Nature 391:806-811; Fire A, Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000): Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058: WO9932619, and Elbashir S M, et al., 2001 Nature 411:494-498).

Accordingly, the invention provides nucleic acid that is capable, when suitably introduced into or expressed within a mammalian, e.g. human, cell that otherwise expresses IL-11, IL-11Rα or gp130, of suppressing IL-11, IL-11Rα or gp130 expression by RNAi.

nucleic acid sequences for IL-11, IL-11Rα and gp130 (e.g. the known mRNA sequences available from GenBank under Accession No.s: BC012506.1 GI:15341754 (human IL-11), BC134354.1 GI:126632002 (mouse IL-11), AF347935.1 GI:13549072 (rat IL-11), NM_001142784.2 GI:391353394 (human IL-11Rα), NM_001163401.1 GI:254281268 (mouse IL-11Rα), NM_139116.1 GI:20806172 (rat IL-11 Rα), NM_001190981.1 GI:300244534 (human gp130), NM_010560.3 GI:225007624 (mouse gp130), NM_001008725.3 GI:300244570 (rat gp130)) oligonucleotides may be designed to repress or silence the expression of IL-11, IL-11Rα or gp130.

The nucleic acid may have substantial sequence identity to a portion of IL-11, IL-11Rα or gp130 mRNA, e.g. as defined in GenBank accession no. NM_000641.3 GI:391353405 (IL-11), NM_001142784.2 GI:391353394 (IL-11Rα), NM_001190981.1 GI:300244534 (gp130) or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridise with each other. In a mammalian cell, the hairpin structure may be cleaved from the molecule by the enzyme DICER, to yield two distinct, but hybridised, RNA molecules.

In some preferred embodiments, the nucleic acid is generally targeted to the sequence of one of SEQ ID NOs 6 to 9 (IL-11) or to one of SEQ ID NOs 10 to 13 (IL-11Rα).

Only single-stranded (i.e. non selt-hybridised) regions of an mRNA transcript are expected to be suitable targets for RNAi. It is therefore proposed that other sequences very close in the IL-11 or IL-11 Rα mRNA transcript to the sequence represented by one of SEQ ID NOs 6 to 9 or 10 to 13 may also be suitable targets for RNAi. Such target sequences are preferably 17-23 nucleotides in length and preferably overlap one of SEQ ID NOs 6 to 9 or 10 to 13 by at least 1, 2, 3, 4, 5, 6, 7, 8, 9, 10, 11, 12, 13, 14, 15, 16, 17, 18 or all 19 nucleotides (at either end of one of SEQ ID NOs 6 to 9 or 10 to 13).

Accordingly, the invention provides nucleic acid that is capable, when suitably introduced into or expressed within a mammalian cell that otherwise expresses IL-11 or IL-11Rα, of suppressing IL-11 or IL-11Rα expression by RNAi, wherein the nucleic acid is generally targeted to the sequence of one of SEQ ID NOs 6 to 9 or 10 to 13.

By "generally targeted" the nucleic acid may target a sequence that overlaps with SEQ ID NOs 6 to 9 or 10 to 13. In particular, the nucleic acid may target a sequence in the mRNA of human IL-11 or IL-11Rα that is slightly longer or shorter than one of SEQ ID NOs 6 to 9 or 10 to 13 (preferably from 17-23 nucleotides in length), but is otherwise identical to one of SEQ ID NOs 6 to 9 or 10 to 13.

It is expected that perfect identity/complementarity between the nucleic acid of the invention and the target sequence, although preferred, is not essential. Accordingly, the nucleic acid of the invention may include a single mismatch compared to the mRNA of IL-11 or IL-11Rα. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences shown in SEQ ID NOs 14 to 17. In another embodiment, the nucleic acid (herein referred to as double-stranded siRNA) includes the double-stranded RNA sequences shown in SEQ ID NOs 18 to 21.

However, it is also expected that slightly shorter or longer sequences directed to the same region of IL-11 or IL-11Rα mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in Drosophila show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c: Czauderna et al. 2003).

Any dinucleotide overhang may therefore be used in the antisense strand of the siRNA. Nevertheless, the dinucleotide is preferably -UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The invention also provides single-stranded nucleic acids (herein referred to as single-stranded siRNAs) respectively consisting of a component strand of one of the aforementioned double-stranded nucleic acids, preferably with the 3'-overhangs, but optionally without. The invention also provides kits containing pairs of such single-stranded nucleic acids, which are capable of hybridising with each other in vitro to form the aforementioned double-stranded siRNAs, which may then be introduced into cells.

The invention also provides DNA that, when transcribed in a mammalian cell, yields an RNA (herein also referred to as an shRNA) having two complementary portions which are capable of self-hybridising to produce a double-stranded motif, e.g. including a sequence selected from the group consisting of SEQ ID NOs: 14 to 17 or 18 to 21 or a sequence that differs from any one of the aforementioned sequences by a single base pair substitution.

The complementary portions will generally be joined by a spacer, which has suitable length and sequence to allow the two complementary portions to hybridise with each other. The two complementary (i.e. sense and antisense) portions may be joined 5-3 in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Wash., USA) is UUCAAGAGA. In this and other cases, the ends of the spacer may hybridise with each other, e.g. elongating the double-stranded motif beyond the exact sequences of SEQ ID NOs 14 to 17 or 18 to 21 by a small number (e.g. 1 or 2) of base pairs.

Similarly, the transcribed RNA preferably includes a 3' overhang from the downstream complementary portion. Again, this is preferably —UU or -UG, more preferably -UU.

Such shRNA molecules may then be cleaved in the mammalian cell by the enzyme DICER to yield a double-stranded siRNA as described above, in which one or each strand of the hybridised dsRNA includes a 3' overhang.

Techniques for the synthesis of the nucleic acids of the invention are of course well known in the art.

The skilled person is well able to construct suitable transcription vectors for the DNA of the invention using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-III promoter (H1) and a T5 transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the invention may be introduced into mammalian cells in vitro or in vivo using known techniques, as described below, to suppress expression of IL-11 or a receptor for IL-11. Similarly, transcription vectors containing the DNAs of the invention may be introduced into tumour cells in vitro or in vivo using known techniques, as described below, for transient or stable expression of RNA, again to suppress expression of IL-11 or a receptor for IL-11.

Accordingly, the invention also provides a method of suppressing expression of IL-11 or a receptor for IL-11 in a mammalian, e.g. human, cell, the method comprising administering to the cell a double-stranded siRNA of the invention or a transcription vector of the invention.

Similarly, the invention further provides a method of treating a disease/condition in which secretory SMCs are pathologically implicated, the method comprising administering to a subject a double-stranded siRNA of the invention or a transcription vector of the invention.

The invention further provides the double-stranded siRNAs of the invention and the transcription vectors of the invention, for use in a method of treatment, preferably a method of treating a disease/condition in which secretory SMCs are pathologically implicated.

The invention further provides the use of the double-stranded siRNAs of the invention and the transcription vectors of the invention in the preparation of a medicament for the treatment of a disease/condition in which secretory SMCs are pathologically implicated.

The invention further provides a composition comprising a double-stranded siRNA of the invention or a transcription vector of the invention in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the invention are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE, dextran and calcium phosphate precipitation. In vivo gene transfer techniques include transfection with viral (typically retroviral) vectors and viral coat protein-liposome mediated transfection (Dzau et al. (2003) Trends in Biotechnology 11, 205-210).

In particular, suitable techniques for cellular administration of the nucleic acids of the invention both in vitro and in vivo are disclosed in the following articles:

General reviews: Borkhardt, A. 2002. Blocking oncogenes in malignant cells by RNA interference—new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCR5. Proc Natl Aced Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7. Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in US patent numbers 6,649,192B and 5,843,509B.

Inhibition of IL-11-Mediated Signalling

In embodiments of the present invention, agents capable of inhibiting the action of IL-11 may possess one or more of the following functional properties:

Inhibition of signalling mediated by IL-11;
Inhibition of signalling mediated by binding of IL-11 to IL-11Rα:gp130 receptor complex;
Inhibition of signalling mediated by binding of IL-11:IL-11Rα complex to gp130 (i.e. IL-11 trans signalling);
Inhibition of a process mediated by IL-11;
Inhibition of myofibroblast generation;
Inhibition of SMC proliferation/migration;
Inhibition of gene/protein expression of collagen or IL-11.

These properties can be determined by analysis of the relevant agent in a suitable assay, which may involve comparison of the performance of the agent to suitable control agents. The skilled person is able to identify an appropriate control conditions for a given assay.

IL-11-mediated signalling and/or processes mediated by IL-11 includes signalling mediated by fragments of IL-11 and polypeptide complexes comprising IL-11 or fragments thereof. IL-11-mediated signalling may be signalling mediated by human IL-11 and/or mouse IL-11. Signalling mediated by IL-11 may occur following binding of IL-11 or an IL-11 containing complex to a receptor to which IL-11 or said complex binds.

In some embodiments, an agent may be capable of inhibiting the biological activity of IL-11 or an IL-11-containing complex.

In some embodiments, the agent is an antagonist of one or more signalling pathways which are activated by signal transduction through receptors comprising IL-11Rα and/or gp130, e.g. IL-11Rα:gp130. In some embodiments, the agent is capable of inhibiting signalling through one or more immune receptor complexes comprising IL-11 Rα and/or gp130, e.g. IL-11Rα:gp130.

In some embodiments, the agent may be capable of inhibiting IL-11-mediated signalling to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the agent (or in the presence of an appropriate control agent). In some embodiments, the agent is capable of reducing IL-11-mediated signalling to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the agent (or in the presence of an appropriate control agent).

In some embodiments, the IL-11-mediated signalling may be signalling mediated by binding of IL-11 to IL-11Rα: gp130 receptor. Such signalling can be analysed e.g. by treating cells expressing IL-11Rα and gp130 with IL-11, or by stimulating IL-11 production in cells which express IL-11Rα and gp130.

The $IC_{50}$ for agent for inhibition of IL-11-mediated signalling may be determined, e.g. by culturing Ba/F3 cells expressing IL-11 Rα and gp130 in the presence of human IL-11 and the agent, and measuring $^3$H-thymidine incorporation into DNA. In some embodiments, the agent may exhibit an $IC_{50}$ of 10 µg/ml or less, preferably one of ≤5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

In some embodiments, the IL-11-mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment, and IL-11. In some embodiments, the soluble IL-11Rα is a soluble (secreted) isoform of IL-11R, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα (e.g. hyper IL-11 as described herein).

In some embodiments, the agent may be capable of inhibiting signalling mediated by binding of IL-11:IL-11Rα complex to gp130, and is also capable of inhibiting signalling mediated by binding of IL-11 to IL-11Rα:gp130 receptor.

In some embodiments, the agent may be capable of inhibiting a process mediated by IL-11, e.g. following stimulation with TGFβ1. Processes mediated by IL-11 include e.g. myofibroblast generation from fibroblasts, proliferation/migration of SMCs, and gene/protein expression of e.g. collagen and IL-11, and can be evaluated either in vitro or in vivo.

In some embodiments, the agent may be capable of inhibiting myofibroblast generation from fibroblasts, e.g. following exposure of the fibroblasts to profibrotic factor (e.g. TGFβ 1). Myofibroblast generation from fibroblasts can be investigated by analysis for myofibroblast markers.

The fibroblasts may be derived from any tissue, including liver, lungs, kidney, heart, blood vessels, eye, skin, pancreas, spleen, bowel (e.g. large or small intestine), brain, and bone marrow. In particular embodiments, the fibroblasts may be cardiac fibroblasts (e.g. atrial fibroblasts), skin fibroblasts, lung fibroblasts, kidney fibroblasts or liver fibroblasts. Fibroblasts may be characterised by gene or protein expression of one or more of COL1A, ACTA2, prolyl-4-hydroxylase, MAS516, and FSP1. Myofibroblast markers may include one or more of increased αSMA, vimentin, palladin, cofilin or desmin (as compared to the level of expression by comparable fibroblasts (e.g. fibroblasts derived from the same tissue)). Myofibroblast generation from fibroblasts can analysed by measuring αSMA protein expression levels using Operetta High-Content Imaging System following stimulation of the fibroblasts with TGFβ1; see e.g. WO 2017/103108 A1, which is hereby incorporated by reference in its entirety.

In some embodiments, the agent may be capable of inhibiting myofibroblast generation from fibroblasts to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of myofibroblast generation from fibroblasts in the absence of the agent (or in the presence of an appropriate control agent). In some embodiments, the agent is capable of reducing myofibroblast generation from fibroblasts to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of myofibroblast generation from fibroblasts in the absence of the agent (or in the presence of an appropriate control agent).

In some embodiments, the agent may be capable of inhibiting proliferation of SMCs (e.g. secretory SMCs), e.g. following stimulation with TGFβ1. SMC proliferation can be measured using e.g. $^3$H-thymidine incorporation, CFSE dilution or EdU incorporation assays as described herein.

In some embodiments, the agent may be capable of inhibiting proliferation of SMCs to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of proliferation in the absence of the agent (or in the presence of an appropriate control agent). In some embodiments, the agent is capable of inhibiting proliferation of SMCs to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of proliferation in the absence of the agent (or in the presence of an appropriate control agent).

In some embodiments, the agent may be capable of inhibiting migration of SMCs (e.g. secretory SMCs), e.g. following stimulation with TGFβ1. SMC migration can be measured using a scratch assay e.g. as described in Example 9 and in Liang et al., Nat Protoc. (2007) 2(2):329-33, or using a Boyden chamber assay as described in Example 9 and in Chen, Methods Mol Biol. (2005) 294:15-22.

In some embodiments, the agent may be capable of inhibiting migration of SMCs to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of migration in the absence of the agent (or in the presence of an appropriate control agent). In some embodiments, the agent is capable of inhibiting migration of SMCs to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of migration in the absence of the agent (or in the presence of an appropriate control agent).

In some embodiments, the agent may be capable of inhibiting gene/protein expression of collagen or IL-11. Gene and/or protein expression can be measured as described herein.

In some embodiments, the agent may be capable of inhibiting gene/protein expression of collagen or IL-11 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of expression in the absence of the agent (or in the presence of an appropriate control agent). In some embodiments, the agent is capable of inhibiting gene/protein expression of collagen or IL-11 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of expression in the absence of the agent (or in the presence of an appropriate control agent).

SMC Dysfunction and Disease

SMC dysfunction is observed in many diseases/conditions, in which these cells aberrantly proliferate, are hypertrophic, migrate, invade, produce and/or modify extracellular matrix and die.

SMCs of the secretory phenotype are pathological effectors in such diseases/conditions. The development or progression of the disease/condition and/or symptoms of the disease/condition may be positively associated with one or more activities of secretory SMCs. That is, secretory SMC activity may cause or contribute to (e.g. exacerbate/potentiate) development/progression of the disease/condition and/or symptoms of the disease/condition.

In some cases the disease/condition may be caused/exacerbated by aberrant phenotype switching of contractile SMCs to a secretory SMC phenotype. In some cases the disease/condition may be caused/exacerbated by there being an increased number/proportion of secretory SMCs in a given tissue/organ/organ system/patient (e.g. as compared to the number/proportion in the absence of the disease/condition).

Diseases characterised by vascular SMC dysfunction include atherosclerosis, hypertension, vascular aneurysms, vascular stenosis and restenosis, atherosclerosis, supravalvular stenosis, pulmonary artery hypertension, plexiform lesions, fibromuscular dysplasia, telangiectasia, amongst others. SMC dysfunction in the visceral organs is implicated in e.g. dysphagia, diarrhoea, constipation, renal and bladder disease, and SMC dysfunction is also implicated in respiratory conditions such as asthma, cystic fibrosis, chronic obstructive pulmonary disease (COPD) and acute respiratory distress syndrome (ARDS).

The following sections provide further description relating to diseases/conditions in which SMCs are pathologically implicated.

Systemic Sclerosis/Scleroderma

Scleroderma (SSc) is a connective tissue condition characterised by complex interactions between endothelial cells, VSMCs, extracellular matrix and circulating mediators, contributing to vascular remodeling, vasospasm, and vessel occlusion[8]. VSMCs are involved in the formation of fibrotic intimal lesions in SSc[9]. Patients with SSc might are hyperresponsive to TGFβ signalling, which is important for the disease pathogenesis[2].

Pulmonary Artery Hypertension

Pulmonary artery hypertension (PAH) is a rare disease but a common complication of connective tissue conditions, the most common being SSc. Endothelial injury, followed by activation of SMC migration, proliferation and extracellular matrix deposition combined with endothelial cell proliferation is the critical underlying pathology of PAH[10]. VSMCs undergo a switch from a contractile to a secretory phenotype in the presence of pro-inflammatory, hypoxic and mitogenic stimuli to bring about the lesions seen in PAH[11].

The primary genetic cause of PAH is due to loss of function mutations in BMPR2[12], a negative regulator of smooth muscle function and TGFβ. In familial cases up to 70% of individuals will have BMPR2 mutations that are associated with VSMC proliferation and the development of PAH.

Plexiform lesions typically located in branching points of muscular arteries, are a hallmark for PAH and they consist of a network of vascular channels, lined up by endothelial cells and a core of myofibroblastic cells[10]. Loss of cytostatic signalling from TGFβ is regarded as the cause of abnormal proliferation of plexiform lesions[10].

Marfan's Syndrome, Aortic Aneurysms and Other Related Conditions

Marfan's syndrome (MFS) is an autosomal dominant connective tissue condition that affects multiple organ systems[13]. Aortic samples from MFS patients[14] show increased pSMADs 2/3 and RhoA protein levels, which points toward increased TGFβ signalling. Elevated TGFβ signalling in MFS has been accepted as the central dogma for MFS pathogenesis by the community based on a series of experiments by the Dietz lab[14-17] for over a decade. TGFβ-neutralizing antibodies can reduce the rate of aortic-root expansion, improve aortic-wall architecture and elastic-fiber maintenance, reduce aortic wall thickness and decrease collagen deposition in MFS models[18].

Furlongs syndrome and Sphrintzen-Goldberg syndrome are MFS-like diseases that manifest with premature closure of skull sutures, aortic dissection and premature closure of skull sutures, mental retardation respectively[13]. TβRI and TGFβR2 mutations have been identified in these diseases, which might explain the phenotypic overlap between them[13]. Similarly, in Loeys-Dietz syndrome (somatic mutations in TGFβR1 and TGFβR2), familial thoracic aortic aneurysm syndrome (germ-line mutation in TGFβR2 and missense mutation in TGFβR1) and arterial tortuosity syndrome show similar vascular manifestations to MFS, further amplifying the importance of TGFβ signalling[19].

Cerebral Aneurysms

Cerebral aneurysms occur in arteries of the brain, mainly at branching points where haemodynamic shear stress is high[20]. A change of VSMC phenotype (to the proinflammatory, sectretory phenotype), increases MMP expression and contributes to the loss of internal elastic lamina, which is the way in which most cerebral aneurysms form[20]. Studies have shown corresponding morphological changes (spindle-shaped to spider-like cells) and reduced expression and staining of contractile markers (smooth muscle myosin heavy chain and smooth muscle-α-actin) in SMCs[21]. Due to its link with TGFβ[20] and other factors that might have an indirect link to IL-11 signal transduction pathway, inhibition of IL-11-mediated signalling may be useful for the prevention or treatment of cerebral aneurysms.

Restenosis Restenosis is characterised by fibrosis, VSMC proliferation and remodeling which results from iatrogenic causes of vascular injury, e.g. angioplasty[13]. VSMC apoptosis drives platelet and fibrin aggregation. Thrombin is also a potent inducer of growth factor production, VSMC proliferation and ECM deposition. Moreover activated platelets release vasoconstrictors (thromboxane, serotonin) and mitogens such as FDGF (potent inducer), EGF, and TGFβ that aggravate this proliferative process. TGFβ mRNA levels are highly upregulated in human restenosis specimens[22]. Overexpression of TGFβ in uninjured porcine arteries results in increased ECM deposition and cellular proliferation in the arterial wall[23]. Similarly blockade of TGFβ by antibodies has been shown to suppress restenosis in rabbit balloon-catheter-injured carotid arteries[24]. In human stenotic lesions, SMAD3 is upregulated as compared to primary atherosclerotic plaques[25]. SMAD3 overexpression is associated with increased intima to medial ratio and an increase in medial and sub intimal cellular proliferation (PCNA positive cells)[26]. Overexpression of (inhibitory) SMAD 7 also reduces restenosis after angioplasty[27]. These studies suggest a strong link between restenosis and TGFβ signalling.

Atherosclerosis

Atherosclerosis is a chronic inflammatory response of the arterial wall initiated by injury resulting from e.g. chemical insults (hyperglycemia), modified low-density lipoprotein (LDL) or physical forces (hypertension)[28]. VSMC proliferation and migration is essential for the stability of atherosclerotic plaques[29]. In late stages of atherosclerosis, apoptosis of VSMC due to the activity of inflammatory cells is known to cause plaque rupture. TGFβ signalling has been shown to inhibit the proliferation, migration, and stimulate apoptosis of VSMCs and endothelial cells[13]. VSMCs isolated from human atherosclerotic lesions, have been shown to be resistant to the anti-proliferative and apoptotic effects of TGFβ, and to possess mutations in and/or decreased expression of TβRII[30]. Blocking systemic TGFβ signalling through neutralizing antibodies[31], expressing dominant negative type II receptors[32] and targeted deletion of one allele[33] worsens atherosclerosis. Increasing TGFβ through administration of tamoxifen improves atherosclerosis[34].

Fibromuscular Dysplasia

Fibromuscular dysplasia (FMD) is a rare non-arteriosclerotic disease, affecting medium sized arteries, and is a known cause for arterial stenosis, beading, dissection, and aneurysms[35]. Renal artery involvement is most common (60-75%), followed by the cervicocranial arteries (25-30%), visceral arteries (9%), and the arteries in the extremities (5%)[36]. Histopathologically, FD lesions are categorized based on the dominant arterial layer involved (media, intima, or adventitia) and the composition of the arterial lesion (collagen deposition, known as fibroplasia, or, less commonly, hyperplasia of smooth muscle cells)[35]. Increased TGFβ1 and TGFβ2 secretion as well as increased circulating levels of TGFβ1 and TGFβ2 have been demonstrated in FMD patients as compared to matched controls[37].

Renal Artery Stenosis

Renal artery stenosis is a disease which encompasses three major clinical syndromes; ischemic nephropathy, hypertension, and destabilizing cardiac syndromes[38]. The most common causes for RAS are atherosclerosis (90%) and fibromuscular dysplasia (10%), and so the pathophysiology follows that of both these diseases[38].

Hypertension

Angiotensin II (AGII) regulates VSMC growth signalling through MAPKs (ERK1/2, JNK, and p38 kinase), Janus kinase (JAK)/signal transducer and activator of transduction (STAT), NF-κB, and phosphatidylinositol 3-kinase (PI3K)[39]. ECM deposition by VSMCs and VSMC growth is important for vascular remodeling in hypertension, particularly hypertension of ageing where vascular compliance is reduced and systolic blood pressures and elevated[39]. In hypertensive rats, VSMCs show greater proliferative and migratory tendencies compared to wild-type controls[40]. Reduction of contractile makers, namely, smooth muscle actin (SMA) and SM22α is associated with a reduction PPAR-γ in rats, and so hypertension may regulates VSMC phenotypic switch via inhibiting PPAR-γ induced PI3K/Akt signalling[40]. The most recent and very large GWAS strongly annotates VSMC function as an important determinant of blood pressure[41].

Kidney Disease

Focal and segmental glomerulosclerosis (FSGS), IgA nephropathy, crescentic glomerulonephritis, lupus nephritis and diabetic nephropathy (DN) are important kidney diseases[42]. Mesangial cell proliferation is important in the progression of these kidney diseases that lead to glomerulosclerosis, a process quite similar to atherosclerosis. Mesangial cells are very similar to VSMCs in terms of origin, microscopic anatomy, histochemistry, and contractility[43] and may be a VSMC subtype. Mesangial cells secrete and surround themselves with the mesangial matrix, which is pivotal in structural support of the glomerulus. In pathological states, mesangial cells de-differentiate to a myofibroblast-like phenotype (mesangioblast), similar to the phenotypic switch VSMC show in response to vascular injury, and produce excessive matrix components[44]. During de-differentiation, mesangial cells also upregulate expression of markers such as αSMA. Increased mesangial compartment size, as a result of mesangial matrix deposition as well as mesangial cell proliferation and hypertrophy, is a hallmark of glomerulosclerosis[45]. As with VSMCs, PDGF has been identified as a potent inducer of mesangial cell proliferation[42]. Other vital transcription factors that promote mesangial proliferation include c-los, c-myc and c-jun. C-fos dimerizes with c-jun to form the AP-1 complex, which transactivates a number of target genes[42]. Mesangial and/or VSMC proliferation or contractile dysfunction of the efferent glomerular artery can lead to glomerular dysfunction and hypertension.

Lung Disease

Airway smooth muscle cells (ASMCs) are strongly involved in lung conditions such as Asthma, Cystic Fibrosis and Chronic Obstructive Pulmonary Disease (COPD)[46]. Airway smooth muscle cells are characterised by comparatively lower expression of contractile proteins, such as smooth muscle myosin heavy chain, calponin, and smooth muscle α-actin, and they remain in a proliferative mode[47]. TGFβ increases the expression of smooth muscle contractile proteins, such as smooth muscle α-actin and calponin, in airway smooth muscle and fibroblasts, and it increases airway smooth muscle cell size and number[48].

Asthma

Asthma is a chronic disease that affects over 300 million patients worldwide, and 250,000 deaths are attributed to asthma annually. Asthma is characterised by airway inflammation, hyper-responsiveness, and remodeling[49]. Frequent stimulation of airway SMCs (ASMCs) by contractile agonists, inflammatory mediators, and growth factors causes structural remodelling that results in irreversible airway obstruction in late stages of the disease. Of the various mediators, TGFβ has been identified[50]. McMillan et al. demonstrated that mice treated with anti-TGFβ antibodies have significantly reduced peribronchiolar extracellular matrix deposition, airway smooth muscle cell proliferation, and mucus production in the lung without affecting established airway inflammation and Th2 cytokine production[51]. The primary treatment of acute asthmatic exacerbations in beta-blockade that alleviates ASMC contractility, highlighting the central role of ASMCs in asthma[52]. ASMCs also produce collagen and secrete pro-inflammatory cytokines that contribute to disease pathogenesis[53].

Chronic Obstructive Pulmonary Disease (COPD)

COPD is a chronic lung condition that is estimated to cause 3 million deaths globally every year. COPD is characterised by tissue repair and epithelial metaplasia that contribute to airway wall thickening and airflow obstruction[48]. Studies have shown that the amount of airway smooth muscle is inversely correlated with lung function and that peribronchial adventitial fibrosis may limit the degree of relaxation induced by bronchodilators, such as β-agonists or anticholinergic drugs[48]. TGFβ is shown to be overexpressed in the airway epithelium and ASMCs of smokers with COPD as compared with smokers without COPD[54].

Intestinal Pathology

Intestinal smooth muscle cells (iSMCs) play an important role in stricture formation within bowel walls (e.g. ileal stricture). This process is commonly seen in inflammatory bowel diseases (e.g. coeliac disease, irritable bowel syndrome, Crohn's disease and ulcerative colitis) and other conditions that result in bowel wall inflammation and thickening. Under physiological conditions, iSMCs are contractile and non-proliferative, and are required for normal bowel function[55]. However in response to various pathological states, they dedifferentiate, re-enter the cell cycle, hypertrophy and switch to a secretory SMC phenotype[55]. The myenteric Interstitial cells of Cajal are specific type of SMC that regulates peristalsis of the gut. These cells are particularly susceptible to transformation into secretory SMCs that adversely affects contraction of the gut (Vetuschi et al., Eur J Clin Invest. (2006) 36(1):41-8). Intestinal SMCs have the potential to rapidly proliferate, synthesize and secrete ECM such as collagen. In vitro experiments have shown that TGFβ induces 100% increase in absolute collagen synthesis per cell in iSMCs[56].

Hutchinson-Gilford Progeria Syndrome (HGPS)

HGPS is a severe human premature aging condition caused by a lamin A mutant named progerin. Severe VSMC loss has been commonly attributed to this cardiovascular mortality in patients with progeria[57]. Progerin expression has been shown to downregulate PARP1 which in turn causes mitotic catastrophe causing SMC death[57]. TGFβ and SMAD are up regulated in progeria, and the MAPK pathway is amongst those which are altered in this disease[58].

Leiomyoma and Leiomyosarcoma

A leiomyoma, also known as fibroids, is a benign smooth muscle tumour that can occur in any organ. Leiomyomas commonly occur in the uterus (i.e. uterine leiomyomas/fibroids), oesophagus, stomach and intestine. They are predominantly derived from the proliferation of a single smooth muscle cell and include vascular SMC phenotypes. Fibroids have also been found to include differentiated cell populations such as fibroblasts and fibroid-associated fibroblasts[65].

Leiomyomas may occur in the skin, such as solitary cutaneous leiomyoma, multiple cutaneous (or pilar) leiomyomas arising from the arrectores pilorum muscles, angioleiomyomas (vascular leiomyomas) that arise from vascular smooth muscle, dartoic (or genital) leiomyomas originating in the dartos muscles of the genitalia, areola and nipple, and angiolipoleiomyoma.

Altered 17β-estradiol (E2) signalling in leiomyomas reportedly causes MAPK activation and pathological cell proliferation via increased levels of phosphorylated ERK1/2[66].

Leiomyosarcoma (LMS) is a malignant smooth muscle tumour that can occur in any organ. Leiomyomas are not generally thought to develop into malignant LMS but leiomyosarcomas often coexist within a fibroid context, e.g. a fibroid uterus[67]. LMS typically express smooth muscle actin (SMA), desmin and caldesmon and thus may display a secretory SMC phenotype.

Hermansky-Pudlak Syndrome (HPS)

HPS is a rare autosomal recessive disorder characterised by oculocutaneous albinism and platelet dysfunction. Individuals with HPS may develop fatal pulmonary fibrosis, inflammation of the gastro-intestinal tract and/or colon (colitis), and/or kidney failure[68]. Murine models of HPS develop fibrosis in the lung and demonstrate elevated TGFβ1 levels[69].

Treatment/Prevention of SMC-Related Diseases/Conditions

The present invention provides methods and compositions for the treatment/prevention of diseases and conditions associated with SMC dysfunction. Diseases/conditions to be treated/prevented in accordance with the present invention may be referred to as being SMC-related or SMC-mediated.

In particular, the invention provides methods and compositions for the treatment/prevention of diseases and conditions in which secretory SMCs are pathologically implicated.

The methods generally involve inhibition of secretory SMC activity, i.e. inhibition of (reduction in the level of) a functional property of secretory SMCs. This is achieved by inhibition of IL-11 mediated signalling.

That is, the present invention provides for the treatment/prevention of diseases/conditions caused/exacerbated by secretory SMCs through inhibition of IL-11 mediated signalling, in e.g. a cell, tissue/organ/organ system/subject It will be clear to the person skilled in the art that the therapeutic and prophylactic utility of the present invention extends to essentially any disease/condition which would benefit from a reduction in the number or activity of secretory SMCs.

A disease/condition in which secretory SMCs are 'pathologically implicated' may be e.g. a disease/condition in which secretory SMCs, or an increased number/proportion of secretory SMCs, is positively associated with onset, development or progression of the disease/condition, and/or severity of one or more symptoms of the disease/condition, or a disease/condition for which secretory SMCs, or an increased number/proportion of secretory SMCs, is a risk factor for the onset, development or progression of the disease/condition. The secretory SMCs may be present in an organ/tissue which is affected by the disease (e.g. an organ/issue in which the symptoms of the disease/condition manifest). The proportion of secretory SMCs may be determined as a proportion of the total number of secretory SMCs plus non-secretory SMCs (e.g. contractile SMCs) in the relevant organ/tissue.

In some embodiments, the disease/condition to be treated/prevented in accordance with the present invention is a disease characterised by an increase in the number/proportion/activity of secretory SMCs, e.g. in an organ/tissue which is affected by the disease/condition (e.g. an organ/tissue in which the symptoms of the disease/condition manifest).

In some embodiments, the disease/condition to be treated/prevented may be characterised by an increase in one or more of the following in an organ/tissue/subject affected by the disease, e.g. as compared to normal (i.e. non-diseased) organ/tissue/subject: number/proportion/activity of secretory SMCs, expression of one or more of: an extracellular matrix component (e.g. collagen I), IL-11, osteopontin, I-caldesmon, NM-B MHC, vimentin, tropomyosin 4, CRBP-1, secretory vesicles and α4β1 integrin. In some embodiments, the disease/condition to be treated/prevented may be characterised by an increase in one or more of the following in an organ/tissue/subject affected by the disease, e.g. as compared to normal (i.e. non-diseased) organ/tissue/subject: number/proportion/activity secretory SMCs, expression of one or more of: an extracellular matrix component, collagen and IL-11.

In some embodiments, the disease/condition to be treated/prevented may be characterised by a decrease in one or more of the following in an organ/tissue/subject affected by the disease, e.g. as compared to normal (i.e. non-diseased) organ/tissue/subject: number/proportion of contractile SMCs, expression of one or more of: myosin 11, smoothelin, SMMHC, αSMA, SM22α, h1-calponin, h-caldesmon, α1β1 integrin, α7β1 integrin, actin filaments and the dystrophin-glycoprotein complex (DGPC). In some embodiments, the disease/condition to be treated/prevented may be characterised by a decrease in one or more of the following in an organ/tissue/subject affected by the disease, e.g. as compared to normal (i.e. non-diseased) organ/tissue/subject: number/proportion of contractile SMCs, expression of one or more of: myocardin and SM22α.

The disease/condition may affect any tissue or organ or organ system. In some embodiments the disease/condition may affect several tissues/organs/organ systems.

In some embodiments, the disease/condition affects one or more of: the cardiovascular system, the digestive system, the excretory system, the respiratory system, the renal system or the reproductive system.

In some embodiments the disease/condition to be treated/prevented affects one or more organs of the cardiovascular system, e.g. the blood vessels (i.e. is a vascular disease/condition). In some embodiments the disease/condition is one or more of: atherosclerosis, hypertension, vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, atherosclerosis, fibromuscular dysplasia (FMD), supravalvular stenosis, renal artery stenosis, pulmonary artery hypertension (PAH), plexiform lesions, fibromuscular dysplasia, telangiectasia, systemic sclerosis, Hutchinson-Gilford Progeria Syndrome (HGPS), leiomyoma or leiomyosarcoma.

In some embodiments the disease/condition to be treated/prevented affects one or more organs of the digestive or excretory systems. In some embodiments the disease/condition is one or more of: achalasia, dysphagia, diarrhoea, constipation, inflammatory bowel disease (IBD), bowel stricture, pyloric stenosis, coeliac disease, irritable bowel syndrome, diverticulitis, Crohn's disease, ulcerative colitis or Hermansky-Pudlak Syndrome (HPS).

In some embodiments the disease/condition to be treated/prevented affects one or more organs of the respiratory system e.g. the airways (i.e. is a respiratory disease/condition). In some embodiments the disease/condition is one or more of: lung disease, asthma, cystic fibrosis, chronic obstructive pulmonary disease (COPD), acute respiratory distress syndrome (ARDS) or Hermansky-Pudlak Syndrome (HPS).

In some embodiments the disease/condition to be treated/prevented affects one or more organs of the renal system e.g. the kidneys or bladder (i.e. is a renal disease/condition). In some embodiments the disease/condition is one or more of: renal disease, focal and segmental glomerulosclerosis (FSGS), IgA nephropathy, crescentic glomerulonephritis, lupus nephritis, diabetic nephropathy (DN), bladder disease or Hermansky-Pudlak Syndrome (HPS).

In some embodiments, the disease/condition to be treated/prevented is one or more of: atherosclerosis, hypertension, vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, atherosclerosis, fibromuscular dysplasia (FMD), supravalvular stenosis, renal artery stenosis, pulmonary artery hypertension (PAH), plexiform lesions, libromuscular dysplasia, telangiectasia, achalasia, dysphagia, diarrhoea, constipation, inflammatory bowel disease (IBD), bowel stricture, pyloric stenosis, coeliac disease, irritable bowel syndrome, diverticulitis, Crohn's disease, ulcerative colitis, renal disease, focal and segmental glomerulosclerosis (FSGS), IgA nephropathy, crescentic glomerulonephritis, lupus nephritis, diabetic nephropathy (DN), bladder disease, lung disease, asthma, cystic fibrosis, chronic obstructive pulmonary disease (COPD), acute respiratory distress syndrome (ARDS), systemic sclerosis, Hutchinson-Gilford Progeria Syndrome (HGPS), leiomyoma, leiomyosarcoma and Hermansky-Pudlak Syndrome (HPS).

In some embodiments the disease/condition is not a disease/condition that affects one or more organs of the respiratory system e.g. the airways (i.e. is not a respiratory disease/condition). In embodiments the disease/condition to be treated/prevented is one or more of: atherosclerosis, hypertension, vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, atherosclerosis, fibromuscular dysplasia (FMD), supravalvular stenosis, renal artery stenosis, pulmonary artery hypertension (PAH), plexiform lesions, fibromuscular dysplasia, telangiectasia, achalasia, dysphagia, diarrhoea, constipation, inflammatory bowel disease (IBD), bowel stricture, pyloric stenosis, coeliac disease, irritable bowel syndrome, diverticulitis, Crohn's disease, ulcerative colitis, renal disease, focal and segmental glomerulosclerosis (FSGS), IgA nephropathy, crescentic glomerulonephritis, lupus nephritis, diabetic nephropathy (DN), bladder disease, systemic sclerosis, Hutchinson-Gilford Progeria Syndrome (HGPS), leiomyoma, leiomyosarcoma and non-airway/non-lung-related pathology of Hermansky-Pudlak Syndrome (HPS). In embodiments, the disease/condition to be treated/prevented is not lung disease, asthma, cystic fibrosis, chronic obstructive pulmonary disease (COPD), acute respiratory distress syndrome (ARDS) or airway/lung-related pathology of Hermansky-Pudlak Syndrome (HPS)

Treatment/prevention of diseases and conditions according to the present invention may be of a disease/condition that is associated with an upregulation of IL-11, e.g. an upregulation of IL-11 in cells or tissue in which the symptoms of the disease/condition manifests or may occur, or upregulation of extracellular IL-11 or IL-11Rα.

Treatment may be effective to prevent progression of the disease/condition, e.g. to reduce/delay/prevent worsening of the disease/condition or to reduce/delay/prevent development of the disease/condition. In some embodiments treatment may lead to an improvement in the disease/condition, e.g. a reduction in the severity of, and/or a reversal of, the symptoms of the disease/disorder. In some embodiments treatment may increase survival.

Prevention may refer to prevention of development of the disease/condition, and/or prevention of worsening of the disease/condition, e.g. prevention of progression of the disease/condition to a later or chronic stage.

Administration

Administration of an agent capable of inhibiting IL-11-mediated signalling is preferably in a "therapeutically effective" or "prophylactically effective" amount, this being sufficient to show benefit to the subject.

The actual amount administered, and rate and time-course of administration, will depend on the nature and severity of the disease/condition and the nature of the agent. Prescription of treatment, e.g. decisions on dosage etc., is within the responsibility of general practitioners and other medical doctors, and typically takes account of the disease/condition to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Multiple doses of the agent may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In therapeutic applications, agents capable of inhibiting IL-11-mediated signalling are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium. The formulation and mode of administration may be selected according to the agent and disease/condition to be treated.

An agent capable of inhibiting IL-11-mediated signalling may be administered for treatment as described herein in conjunction with other treatments for diseases and conditions associated with SMC dysfunction. Suitable other treatments will be known by a person skilled in the art. An agent may be administered alone or in combination with other treatments, either simultaneously or sequentially dependent upon the disease/condition to be treated. For example, the article may be administered before, at the same time as, or after the treatment. The article and the treatment may be formulated together, e.g. in a formulation described above, or formulated separately.

Detection of IL-11 and Receptors for IL-11

Some aspects and embodiments of the present invention concern detection of expression of IL-11 or a receptor for IL-11 (e.g. IL-11Rα, gp130, or a complex containing IL-11Rα and/or gp130) in a sample obtained from a subject.

In some aspects and embodiments the present invention concerns the upregulation of expression (over-expression) of IL-11 or a receptor for IL-11 (as a protein or oligonucleotide encoding the respective IL-11 or receptor for IL-11) and detection of such upregulation as an indicator of suitability for treatment with an agent capable of inhibiting the action of IL-11 or with an agent capable of preventing or reducing the expression of IL-11 or a receptor for IL-11.

Upregulated expression comprises expression at a level that is greater than would normally be expected for a cell or tissue of a given type. Upregulation may be determined by measuring the level of expression of the relevant factor in a cell or tissue. Comparison may be made between the level of expression in a cell or tissue sample from a subject and a reference level of expression for the relevant factor, e.g. a value or range of values representing a normal level of expression of the relevant factor for the same or corresponding cell or tissue type. In some embodiments reference levels may be determined by detecting expression of IL-11 or a receptor for Il-11 in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of IL-11 or a receptor for IL-11 (e.g. IL-11Rα, gp130, or a complex containing IL-11Rα and/or gp130) may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

Expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of IL-11 or a receptor for IL-11 in a sample by contacting the sample with an agent capable of binding IL-11 or a receptor for IL-11 and detecting the formation of a complex of the agent and IL-11 or receptor for IL-11. The agent may be any suitable binding molecule, e.g. an antibody, polypeptide, peptide, oligonucleotide, aptamer or small molecule, and may optionally be labelled to permit detection, e.g. visualisation, of the complexes formed. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. $^{32}$P, $^{33}$P, $^{35}$S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of IL-11 or receptor for IL-11 in a sample. Quantified amounts of IL-11 or receptor for IL-11 from a test sample may be compared with reference values, and the comparison used to determine whether the test sample contains an amount of IL-11 or receptor for IL-11 that is higher or lower than that of the reference value to a selected degree of statistical significance.

Quantification of detected IL-11 or receptor for IL-11 may be used to determine up- or down-regulation or amplification of genes encoding IL-11 or a receptor for IL-11. In cases where the test sample contains fibrotic cells, such up-regulation, down-regulation or amplification may be compared to a reference value to determine whether any statistically significant difference is present.

A sample obtained from a subject may be of any kind. A biological sample may be taken from any tissue or bodily fluid, e.g. a blood sample, blood-derived sample, serum sample, lymph sample, semen sample, saliva sample, synovial fluid sample. A blood-derived sample may be a selected fraction of a patient's blood, e.g. a selected cell-containing fraction or a plasma or serum fraction. A sample may comprise a tissue sample or biopsy; or cells isolated from a subject. Samples may be collected by known techniques, such as biopsy or needle aspirate. Samples may be stored and/or processed for subsequent determination of IL-11 expression levels.

Samples may be used to determine the upregulation of IL-11 or receptor for IL-11 in the subject from which the sample was taken.

In some preferred embodiments a sample may be a tissue sample, e.g. biopsy, taken from vascular or cardiac tissue, visceral organ tissue, or respiratory system organ tissue. A sample may contain cells, and may preferably contain smooth muscle cells (SMCs).

A subject may be selected for therapy/prophylaxis in accordance with the present invention based on determination that the subject has an upregulated level of expression of IL-11 or of a receptor for IL-11 (e.g. IL-11Rα, gp130, or a complex containing IL-11Rα and/or gp130). Unregulated expression of IL-11 or of a receptor for IL-11 may serve as a marker of a disease/condition in which SMCs are pathologically implicated suitable for treatment with an agent capable of inhibiting IL-11 mediated signalling.

Upregulation may be in a given tissue or in selected cells from a given tissue. A preferred tissue may be vascular or cardiac tissue, visceral organ tissue, or respiratory system organ tissue. A preferred cell type may be SMCs. Upregulation of expression of IL-11 or of a receptor for IL-11 may also be determined in a circulating fluid, e.g. blood, or in a blood derived sample. Upregulation may be of extracellular IL-11 or IL-11Rα. In some embodiments expression may be locally or systemically upregulated.

Following selection, a subject may be administered with an agent capable of inhibiting IL-11 mediated signalling.

Diagnosis and Prognosis

Detection of upregulation of expression of IL-11 or a receptor for IL-11 (e.g. IL-11Rα, gp130, or a complex containing IL-11Rα and/or gp130) may also be used in a method of diagnosing a disease/condition in which secretory SMCs are pathologically implicated, identifying a subject at risk of developing such disease/condition, and in methods of prognosing or predicting a subject's response to treatment with an agent capable of inhibiting IL-11 mediated signalling.

In some embodiments a subject may be suspected of having a disease/condition in which secretory SMCs are pathologically implicated, e.g. based on the presence of other symptoms indicative of such disease/condition in the subject's body or in selected cells/tissues of the subject's body, or be considered at risk of developing a disease/condition in which secretory SMCs are pathologically implicated, e.g. because of genetic predisposition or exposure to environmental conditions, known to be risk factors for such disease/condition. Determination of upregulation of expression of IL-11 or a receptor for IL-11 may confirm a diagnosis or suspected diagnosis, or may confirm that the subject is at risk of developing the disease/condition. The determination may also diagnose the condition or predisposition as one suitable for treatment with an agent capable of inhibiting IL-11-mediated signalling.

As such, a method of providing a prognosis for a subject having, or suspected of having a disease/condition in which secretory SMCs are pathologically implicated may be provided, the method comprising determining whether the expression of IL-11 or a receptor for IL-11 is upregulated in a sample obtained from the subject and, based on the determination, providing a prognosis for treatment of the subject with an agent capable of inhibiting IL-11-mediated signalling.

In some aspects, methods of diagnosis or methods of prognosing or predicting a subject's response to treatment with an agent capable of inhibiting IL-11-mediated signalling may not require determination of the expression of IL-11 or a receptor for IL-11, but may be based on determining genetic factors in the subject that are predictive of upregulation of expression or activity. Such genetic factors may include the determination of genetic mutations, single nucleotide polymorphisms (SNPs) or gene amplification in IL-11, IL-11Rα and/or gp130 which are correlated with and/or predictive of upregulation of expression or activity and/or IL-11 mediated signalling. The use of genetic factors to predict predisposition to a disease state or response to treatment is known in the art, e.g. see Peter Stärkel *Gut* 2008; 57:440-442; Wright et al., Mol. Cell. Biol. March 2010 vol. 30 no. 6 1411-1420.

Genetic factors may be assayed by methods known to those of ordinary skill in the art, including PCR based assays, e.g. quantitative PCR, competitive PCR. By determining the presence of genetic factors, e.g. in a sample obtained from a subject, a diagnosis may be confirmed, and/or a subject may be classified as being at risk of developing a disease/condition, and/or a subject may be identified as being suitable for treatment with an agent capable of inhibiting IL-11 mediated signalling.

Some methods may comprise determination of the presence of one or more SNPs linked to secretion of IL-11 or susceptibility to development a disease/condition in which secretory SMCs are pathologically implicated. SNPs are usually bi-allelic and therefore can be readily determined using one of a number of conventional assays known to those of skill in the art (e.g. see Anthony J. Brookes. The essence of SNPs. Gene Volume 234, Issue 2, 8 Jul. 1999, 177-186: Fan et al., Highly Parallel SNP Genotyping. Cold Spring Harb Symp Quant Biol 2003. 68: 69-78: Matsuzaki et al., Parallel Genotyping of Over 10,000 SNPs using a one-primer assay on a high-density oligonucleotide array. Genome Res. 2004. 14: 414-425).

The methods may comprise determining which SNP allele is present in a sample obtained from a subject. In some embodiments determining the presence of the minor allele may be associated with increased IL-11 secretion or susceptibility to development of a disease/condition in which secretory SMCs are pathologically implicated.

Accordingly, in one aspect of the present invention a method for screening a subject is provided, the method comprising:
  obtaining a nucleic acid sample from the subject;
  determining which allele is present in the sample at the polymorphic nucleotide position of one or more of the SNPs listed in FIG. 33, FIG. 34, or FIG. 35 of WO 2017/103108 A1 (incorporated by reference herein), or a SNP in linkage disequilibrium with one of the listed SNPs with an $r^2 \geq 0.8$.

The determining step may comprise determining whether the minor allele is present in the sample at the selected polymorphic nucleotide position. It may comprise determining whether 0, 1 or 2 minor alleles are present.

The screening method may be, or form part of, a method for determining susceptibility of the subject to development of a disease/condition in which secretory SMCs are pathologically implicated, or a method of diagnosis or prognosis as described herein.

The method may further comprise the step of identifying the subject as having susceptibility to, or an increased risk of, developing a disease/condition in which secretory SMCs are pathologically implicated, e.g. if the subject is determined to have a minor allele at the polymorphic nucleotide position. The method may further comprise the step of selecting the subject for treatment with an agent capable of inhibiting IL-11 mediated signalling and/or administering an agent capable of inhibiting IL-11 mediated signalling to the subject in order to provide a treatment for the disease/condition in the subject or to prevent development or progression of the disease/condition in the subject.

SNPs that may be determined include one or more of the SNPs listed in FIG. 33, FIG. 34, or FIG. 35 of WO 2017/103108 A1 (incorporated by reference herein). In some embodiments the method may comprise determining one or more of the SNPs listed in FIG. 33 of WO 2017/103108 A1. In some embodiments the method may comprise determining one or more of the SNPs listed in FIG. 34 of WO 2017/103108 A1. In some embodiments the method may comprise determining one or more of the SNPs listed in FIG. 35 of WO 2017/103108 A1. SNPs may be selected for determination as having a low P value or FDR (false discovery rate).

In some embodiments SNPs are selected as being good predictors of response to anti-IL-11 treatment based on regulation of VSTstim in trans (FIG. 33 of WO 2017/103108 A1). In some embodiments a method may comprise determining which allele is present for one or more of the following SNPs: rs10831850, rs4756936, rs6485827, rs7120273, and rs895468. In some embodiments SNPs are selected as being good predictors of response to anti-IL-11 treatment based on regulation VSTstim-VSTunstim in cis (FIG. 34 of WO 2017/103108 A1).

In some embodiments SNPs are selected as being good predictors of response to anti-IL-11 treatment based on regulation VSTstim-VSTunstim in trans (FIG. 35 of WO 2017/103108 A1). In some embodiments a method may comprise determining which allele is present for one or more of the following SNPs: rs7120273, rs10831850, rs4756936, rs6485827 (FIG. 35 of WO 2017/103108 A1).

SNPs: rs7120273, rs10831850, rs4756936, rs6485827 are in high linkage disequilibrium (LD) with one another on chromosome 11 (in a so-called LD block), and are therefore very commonly co-inherited.

The square of the correlation of gene frequencies ($r^2$) reflects the degree of linkage disequilibrium (LD) between two SNPs. As a result of LD between SNPs in local and therefore co-inherited regions of the genome, the genotype of a given SNP can be inferred by determining the genotype of a tagging/proxy SNP. The threshold of LD used in the art to identify pairwise tagging/proxy SNPs is an rz value of 0.8 (Wang et al. 2005, Nat. Rev. Genet. 6(2): 109-18; Barrett et al. 2006, Nat Genet., 38 (6): 659-662). The genotype of a given SNP can therefore be inferred by determining the genotype of a tagging/proxy SNP in linkage disequilibrium with an $r^2$ value $\geq 0.8$.

The nucleotide sequence of SNPs is indicated using the "rs" number. The full sequence is available from the National Center for biotechnology Information (NCBI) database of single nucleotide polymorphisms (dbSNP) accessible at: https://www.ncbi.nlm.nih.gov/snp.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body.

Other diagnostic or prognostic tests may be used in conjunction with those described here to enhance the accuracy of the diagnosis or prognosis or to confirm a result obtained by using the tests described here.

Subjects

Subjects may be animal or human. Subjects are preferably mammalian, more preferably human. The subject may be a non-human mammal, but is more preferably human. The subject may be male or female. The subject may be a patient. The patient may have a disease/condition as described herein. A subject may have been diagnosed with a disease/condition requiring treatment, may be suspected of having such a disease/condition, or may be at risk from developing such disease/condition.

In embodiments according to the present invention the subject is preferably a human subject. In some embodiments, the subject to be treated according to a therapeutic or prophylactic method of the invention herein is a subject having, or at risk of developing, a cancer. In embodiments according to the present invention, a subject may be selected for treatment according to the methods based on characterisation for certain markers of such disease/disorder/condition. A subject may have been diagnosed with the disease or disorder requiring treatment, or be suspected of having such a disease/disorder/condition.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human IL-11 (UniProt P20809) | MNCVCRLVLVVLSLWPDTAVAPGPPPGPPRVSPDPRAELDSTVLLTRSLLADTRQLAAQLRD KFPADGDHNLDSLPTLAMSAGALGALQLPGVLTRLRADLLSYLRHVQWLRRAGGSSLKTLEP ELGTLQARLDRLLRRLQLLMSRLALPQPPPDPPAPPLAPPSSAWGGIRAAHAILGGLHLTLDW AVRGLLLLKTRL |
| 2 | Human gp130 (UniProt P40189-1) | MLTLQTWLVQALFIFLTTESTGELLDPCGYISPESPVVQLHSNFTAVCVLKEKCMDYFHVNANY IVWKTNHFTIPKEQYTIINRTASSVTFTDIASLNIQLTCNILTFGQLEQNVYGITIISGLPPEKPKNL SCIVNEGKKMRCEWDGGRETHLETNFTLKSEWATHKFADCKAKRDTPTSCTVDYSTVYFVNI EVWVEAENALGKVTSDHINFDPVYKVKPNPPHNLSVINSEELSSILKLTWTNPSIKSVIILKYNIQ YRTKDASTWSQIPPEDTASTRSSSFTVQDLKPFTEYVFRIRCMKEDGKGYWSDWSEEASGITY EDRPSKAPSFWYKIDPSHTQGYRTVQLVWKTLPPFEANGKILDYEVTLTRWKSHLQNYTVNA TKLTVNLTNDRYLATLTVRNLVGKSDAAVLTIPACDFQATHPVMDLKAFPKDNMLWVEWTTPR ESVKKYILEWCVLSDKAPCITDWQQEDGTVHRTYLRGNLAESKCYLITVTPVYADGPGSPESI KAYLKQAPPSKGPTVRTKKVGKNEAVLEWDQLPVDVQNGFIRNYTIFYRTIIGNETAVNVDSS HTEYTLSSLTSDTLYMVRMAAYTDEGGKDGPEFTFTTPKFAQGEIEAIVVPVCLAFLLTTLLGV LFCFNKRDLIKKHIWPNVPDPSKSHIAQWSPHTPPRHNFNSKDQMYSDGNFTDVSVVEIEAND KKPFPEDLKSLDLFKKEKINTEGHSSGIGGSSCMSSSRPSISSSDENESSQNTSSTVQYSTVV HSGYRHQVPSVQVFSRSESTQPLLDSEERPEDLQLVDHVDGGDGILPRQQYFKQNCSQHES SPDISHFERSKQVSSVNEEDFVRLKQQISDHISQSCGSGQMKMFQEVSAADAFGPGTEGQVE RFETVGMEAATDEGMPKSYLPQTVRQGGYMPQ |
| 3 | Human 1L11RA (UniProt Q14626) | MSSSCSGLSRVLVAVATALVSASSPCPQAWGPPGVQYGQPGRSVKLCCPGVTAGDPVSWF RDGEPKLLQGPDSGLGHELVLAQADSTDEGTYICQTLDGALGGTVTLQLGYPPARPVVSCQA ADYENFSCTWSPSQISGLPTRYLTSYRKKTVLGADSQRRSPSTGPWPCPQDPLGAARCVVH GAEFWSQYRINVTEVNPLGASTRLLDVSLQSILRPDPPQGLRVESVPGYPRRLRASWTYPAS WPCQPHFLLKFRLQYRPAQHPAWSTVEPAGLEEVITDAVAGLPHAVRVSARDFLDAGTWST WSPEAWGTPSTGTIPKEIPAWGQLHTQPEVEPQVDSPAPPRPSLQPHPRLLDHRDSVEQVA VLASLGILSFLGLVAGALALGLWLRLRRGGKDGSPKPGFLASVIPVDRRPGAPNL |
| 4 | Hyper IL-11 (IL-11RA:IL-11 fusion) | MSSSCSGLSRVLVAVATALVSASSPCPQAWGPPGVQYGQPGRSVKLCCPGVTAGDPVSWF RDGEPKLLQGPDSGLGHELVLAQADSTDEGTYICQTLDGALGGTVTLQLGYPPARPVVSCQA ADYENFSCTWSPSQISGLPTRYLTSYRKKTVLGADSQRRSPSTGPWPCPQDPLGAARCVVH GAEFWSQYRINVTEVNPLGASTRLLDVSLQSILRPDPPQGLRVESVPGYPRRLRASWTYPAS WPCQPHFLLKFRLQYRPAQHPAWSTVEPAGLEEVITDAVAGLPHAVRVSARDFLDAGTWST WSPEAWGTPSTGPAGQSGGGGSGGGSGGGSVPGPPPGPPRVSPDPRAELDSTVLLTRSL LADTRQLAAQLRDKFPADGDHNLDSLPTLAMSAGALGALQLPGVLTRLRADLLSYLRHVQWL RRAGGSSLKTLEPELGTLQARLDRLLRRLQLLMSRLALPQPPPDPPAPPLAPPSSAWGGIRAA HAILGGLHLTLDWAVRGLLLLKTRL |
| 5 | 20 amino acid linker | GPAGQSGGGGSGGGSGGGSV |
| 6 | siRNA target IL-11 | CCTTCCAAAGCCAGATCTT |
| 7 | siRNA target IL-11 | GCCTGGGCAGGAACATATA |
| 8 | siRNA target IL-11 | CCTGGGCAGGAACATATAT |
| 9 | siRNA target IL-11 | GGTTCATTATGGCTGTGTT |
| 10 | siRNA target IL-11Ra | GGACCATACCAAAGGAGAT |
| 11 | siRNA target IL-11Ra | GCGTCTTTGGGAATCCTTT |
| 12 | siRNA target IL-11Ra | GCAGGACAGTAGATCCCT |
| 13 | siRNA target IL-11Ra | GCTCAAGGAACGTGTGTAA |
| 14 | siRNA to IL-11 (NM_000641.3) | CCUUCCAAAGCCAGAUCUUdTdT-AAGAUCUGGCUUUGGAAGGdTdT |

-continued

| SEQ ID NO: | DESCRIPTION | SEQUENCE |
|---|---|---|
| 15 | siRNA to IL-11 (NM_000641.3) | GCCUGGGCAGGAACAUAUAdTdT-UAUAUGUUCCUGCCCAGGCdTdT |
| 16 | siRNA to IL-11 (NM_000641.3) | CCUGGGCAGGAACAUAUAUdTdT-AUAUAUGUUCCUGCCCAGGdTdT |
| 17 | siRNA to IL-11 (NM_000641.3) | GGUUCAUUAUGGCUGUGUUdTdT-AACACAGCCAUAAUGAACCdTdT |
| 18 | siRNA to IL-11Ra (U32324.1) | GGACCAUACCAAAGGAGAUdTdT-AUCUCCUUUGGUAUGGUCCdTdT |
| 19 | siRNA to IL-11Ra (U32324.1) | GCGUCUUUGGGAAUCCUUUdTdT-AAAGGAUUCCCAAAGACGCdTdT |
| 20 | siRNA to IL-11Ra (U32324.1) | GCAGGACAGUAGAUCCCUAdTdT-UAGGGAUCUACUGUCCUGCdTdT |
| 21 | siRNA to IL-11Ra (U32324.1) | GCUCAAGGAACGUGUGUAAdTdT-UUACACACGUUCCUUGAGCdTdT |

Numbered Statements

The following numbered paragraphs (paras) describe particular aspects and embodiments of the present invention:

1. An agent capable of inhibiting interleukin 11 (IL-11)-mediated signalling for use in a method of treating or preventing a disease in which smooth muscle cells (SMCs) are pathologically implicated.

2. Use of an agent capable of inhibiting interleukin 11 (IL-11)-mediated signalling for use in the manufacture of a medicament for use in a method of treating or preventing a disease in which smooth muscle cells (SMCs) are pathologically implicated.

3. A method of treating or preventing a disease in which smooth muscle cells (SMCs) are pathologically implicated, the method comprising administering to a subject in need of treatment a therapeutically effective amount of an agent capable of inhibiting interleukin 11 (IL-11)-mediated signalling.

4. The agent for use in a method according to para 1, the use according to para 2 or the method according to para 3, wherein the disease is a disease in which secretory SMCs are pathologically implicated.

5. The agent for use, the use or the method according to any one of paras 1 to 4, wherein the agent is an agent capable of binding to IL-11 or a receptor for IL-11.

6. The agent for use, the use or the method according to para 5, wherein the agent is selected from the group consisting of: an antibody or an antigen-binding fragment thereof, a polypeptide, a peptide, an oligonucleotide, an aptamer or a small molecule.

7. The agent for use, the use or the method according to para 6, wherein the agent is an antibody or antigen-binding fragment thereof.

8. The agent for use, the use or the method according to para 6, wherein the agent is a decoy IL-11 receptor.

9. The agent for use, the use or the method according to any one of paras 1 to 4, wherein the agent is capable of reducing the expression of IL-11 or a receptor for IL-11.

10. The agent for use, the use or the method according to para 9, wherein the agent is an oligonucleotide or a small molecule.

11. The agent for use, the use or the method according to any one of paras 1 to 10, wherein the disease is a disease of the cardiovascular system the digestive system, the excretory system, the respiratory system, the renal system or the reproductive system.

12. The agent for use, the use or the method according to any one of paras 1 to 11, wherein the disease is selected from the group consisting of: atherosclerosis, hypertension, vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, atherosclerosis, fibromuscular dysplasia (FMD), supravalvular stenosis, renal artery stenosis, pulmonary artery hypertension (PAH), plexiform lesions, fibromuscular dysplasia, telangiectasia, achalasia, dysphagia, diarrhoea, constipation, inflammatory bowel disease (IBD), bowel stricture, pyloric stenosis, coeliac disease, irritable bowel syndrome, diverticulitis, Crohn's disease, ulcerative colitis, renal disease, focal and segmental glomerulosclerosis (FSGS), IgA nephropathy, crescentic glomerulonephritis, lupus nephritis, diabetic nephropathy (DN), bladder disease, lung disease, asthma, cystic fibrosis, chronic obstructive pulmonary disease (COPD), acute respiratory distress syndrome (ARDS), systemic sclerosis and Hutchinson-Gilford Progeria Syndrome (HGPS).

13. The agent for use, the use or the method according to any one of paras 1 to 12, wherein the method of treating or preventing comprises administering the agent to a subject in which expression of IL-11 or a receptor for IL-11 is upregulated.

14. The agent for use, the use or the method according to any one of paras 1 to 13, wherein the method of treating or preventing comprises administering the agent to a subject in expression of IL-11 or a receptor for IL-11 has been determined to be upregulated.

15. The agent for use, the use or the method according to any one of paras 1 to 14, wherein the method of treating or preventing comprises determining whether expression of IL-11 or a receptor for IL-11 is upregulated in the subject and administering the agent to a subject in which expression of IL-11 or a receptor for IL-11 is upregulated.

16. Use of an agent capable of inhibiting interleukin 11 (IL-11)-mediated signalling to inhibit smooth muscle cell (SMC) activity.

17. A method for inhibiting the activity of smooth muscle cells (SMCs), the method comprising contacting SMCs with an agent capable of inhibiting interleukin 11 (IL-11)-mediated signalling.

18. A method for inhibiting the activity of smooth muscle cells (SMCs) in a subject, the method comprising administering an agent capable of inhibiting interleukin 11 (IL-11)-mediated signalling to the subject.

19. The use or the method according to any one of paras 16 to 18, wherein SMCs are secretory SMCs.

20. The use or the method according to any one of paras 16 to 19, wherein the agent is an agent capable of binding to IL-11 or a receptor for IL-11.

21. The use or the method according to any one of paras 16 to 20, wherein the agent is selected from the group consisting of: an antibody or an antigen-binding fragment thereof, a polypeptide, a peptide, an oligonucleotide, an aptamer or a small molecule.

22. The use or the method according to any one of paras 16 to 21, wherein the agent is an antibody or antigen-binding fragment thereof.

23. The use or the method according to any one of paras 16 to 21, wherein the agent is a decoy IL-11 receptor.

24. The use or the method according to any one of paras 16 to 21, wherein the agent is capable of reducing the expression of IL-11 or a receptor for IL-11.

25. The use or the method according to any one of paras 16 to 21, wherein the agent is an oligonucleotide or a small molecule.

26. A method of determining the suitability of a subject for the treatment or prevention of a disease in which smooth muscle cells (SMCs) are pathologically implicated with an agent capable of inhibiting the action of Interleukin 11 (IL-11), the method comprising determining, optionally in vitro, whether IL-11 or an Interleukin 11 receptor (IL-11R) expression is upregulated in the subject.

27. A method of selecting a subject for the treatment or prevention of a disease in which smooth muscle cells (SMCs) are pathologically implicated with an agent capable of inhibiting interleukin 11 (IL-11)-mediated signalling, the method comprising determining, optionally in vitro, whether expression of IL-11 or a receptor for IL-11 is upregulated in the subject.

28. A method of diagnosing a disease in which smooth muscle cells (SMCs) are pathologically implicated or a risk of developing a disease in which SMCs are pathologically implicated in a subject, the method comprising determining, optionally in vitro, the upregulation of the expression of interleukin 11 (IL-11) or a receptor for IL-11 in a sample obtained from the subject.

29. The method of para 28, wherein the method is a method of confirming a diagnosis of a disease in which SMCs are pathologically implicated in a subject suspected of having a disease in which SMCs are pathologically implicated.

30. The method of para 28 or para 29, wherein the method further comprises selecting the subject for treatment with an agent capable of inhibiting IL-11-mediated signalling.

31. The method of any one of paras 26 to 30, wherein the disease is a disease in which secretory SMCs are pathologically implicated.

32. A method of providing a prognosis for a subject having, or suspected of having, a disease in which smooth muscle cells (SMCs) are pathologically implicated, the method comprising determining, optionally in vitro, whether expression of interleukin 11 (IL-11) or a receptor for IL-11 is upregulated in a sample obtained from the subject and, based on the determination, providing a prognosis for treatment of the subject with an agent capable of inhibiting IL-11-mediated signalling.

33. The method of para 32, wherein the method further comprises selecting a subject determined to have upregulated expression of expression of IL-11 or a receptor for IL-11 for treatment with an agent capable of inhibiting IL-11-mediated signalling.

34. A method of diagnosing a disease in which smooth muscle cells (SMCs) are pathologically implicated or a risk of developing a disease in which SMCs are pathologically implicated in a subject, the method comprising determining, optionally in vitro, one or more genetic factors in the subject that are predictive of upregulation of expression of IL-11 or a receptor for IL-11, or of upregulation of IL-11 mediated signalling.

35. The method of para 34, wherein the method is a method of confirming a diagnosis of a disease in which smooth muscle cells (SMCs) are pathologically implicated in a subject suspected of having a disease in which SMCs are pathologically implicated.

36. The method of para 34 or para 35, wherein the method further comprises selecting the subject for treatment with an agent capable of inhibiting IL-11-mediated signalling.

37. A method of providing a prognosis for a subject having, or suspected of having, a disease in which smooth muscle cells (SMCs) are pathologically implicated, the method comprising determining, optionally in vitro, one or more genetic factors in the subject that are predictive of upregulation of expression of IL-11 or a receptor for IL-11, or of upregulation of IL-11 mediated signalling.

38. The method of any one of paras 32 to 37, wherein the disease is a disease in which secretory SMCs are pathologically implicated.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Methods disclosed herein may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

Where a nucleic acid sequence is disclosed herein, the reverse complement thereof is also expressly contemplated.

BRIEF DESCRIPTION OF THE FIGURES

Embodiments and experiments illustrating the principles of the invention will now be discussed with reference to the accompanying figures.

(FIGS. 6A and 6B) MA plots showing DEseq263-corrected log 2 fold changes over the mean of normalized count in AB and LIMA respectively. (FIGS. 6C and 6D) graphical representation of all genes upregulated (FC>1) in response to TGFβ1-stimulation of AB and LIMA VSMCs, and their chromosomal genomic position. IL-11 is highlighted.

(FIG. 12A) Percentage of SM22α-positive cells. (FIG. 12B) Intensity of myocardin immunostaining. (FIG. 12C) Intensity of collagen I immunostaining. (FIG. 12D) Collagen I content of cell culture supernatant as determined using Sirius Red total collagen assay on 5 biological replicates. (FIG. 12E) Representative high resolution fluorescent images after TGFβ1 and IL-11 treatment of VSMCs. Immunostaining for nuclei (DAPI), Collagen 1 (Col 1) and F-actin (Rhodamine) indicate that both TGFβ1 and IL-11 activate the secretory VSMC phenotype with increased collagen expression. White bar represents 200 μm. All data expressed as mean±SD and statistical significance analysed with one-way ANOVA with Dunnett's multiple comparisons.

(FIG. 15A) Percentage of EdU-positive cells. (FIG. 15B) Intensity of collagen I immunostaining. (FIG. 15C) Collagen I content of cell culture supernatant as determined using Sirius Red total collagen assay on 5 biological replicates. All data expressed as mean±SD., statistical significance was determined by one-way ANOVA with Dunnett's multiple comparisons.

FIG. 23D shows that SMRS mice lungs show increased lung fibrosis and infiltrating cell infiltrates compared to SMWT controls in two representative examples.

FIG. 32A). FIGS. 32B to 32D depict densitometry assessment of IL-11 expression as compared to GAPDH expression in heart, lung, and aorta of MFS mice, respectively.

FIGS. 33A and 33B show aortic root internal dimension at end-systole and end-diastole for sham controls without TAC, and post-TAC mice after treatment with anti-IL11, anti-IL11Rα or IgG control antibodies. FIGS. 33C and 33D show aortic arch peak velocity and pressure gradient, respectively. *, , * denote P<0.05, P<0.01 and P<0.001 respectively.

FIGS. 35A and 35B. Representative images (FIG. 35A) and cumulative plots (FIG. 35B) show migration of VSMCs from mice treated with recombinant mouse IL-11 (5 ng/ml) and recombinant mouse TGFβ1 (5 ng/ml) with and without anti-IL11 antibody (2 μg/ml) or equivalent concentration of IgG isotype control for 0 h (upper panels) or 24 h (lower panels). Scale bar represents 200 μm.*, ** denotes P<0.05, P<0.01 respectively.

EXAMPLES

Figure 1:
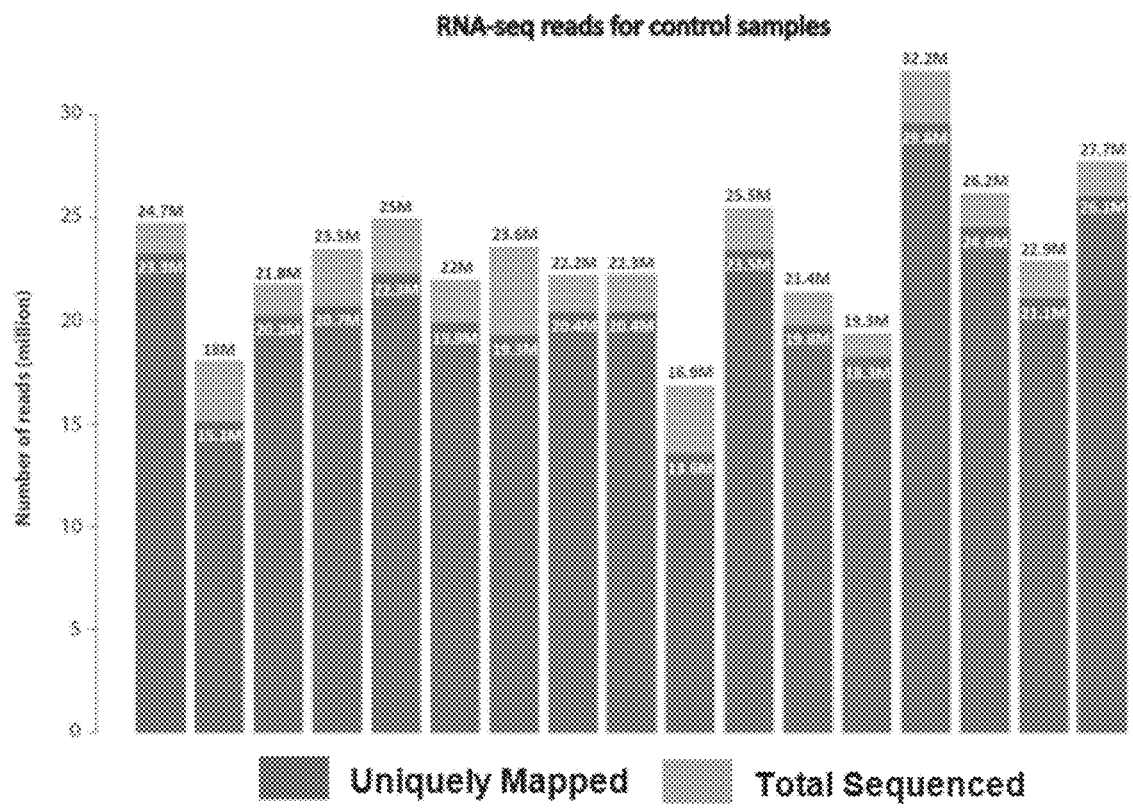
FIG. 1. Bar chart showing RNA-seq of human VSMCs at baseline. The bars indicate the number of reads generated per sample (n=17). Close to 20 million total reads were generated per sample to analyse RNA expression on a genome-wide scale for primary VSMCs.

In the following Examples, the inventors demonstrate that IL-11 gene and protein expression is upregulated in SMCs in response to treatment with TGFβ1, that IL-11 stimulation of SMCs causes production of IL-11 in an autocrine loop, that stimulation of SMCs with either of TGFβ1 or IL-11 decreases expression of the normal, contractile SMC phenotype and upregulates expression of markers of the pathological secretory SMC phenotype, and that inhibition of IL-11-mediated signalling with neutralising anti-IL-11 antibody abrogates the effects of TGFβ1 stimulation on SMC phenotype/activity.

SMC phenotype can switch between physiological contractile/relaxation phenotype and a pathological proliferative/hyperplastic/matrix-synthesizing state[3]. The latter pathological phenotype is implicated in several diseases which are often associated with increased TGFβ1-signalling, as well as activation of other pathways.

TGFβ1 and its receptors have been suggested as therapeutic targets for SMC related diseases, but their inhibition is associated with severe side effects[59,60]. The inventors sought to identify targetable factors downstream of TGFβ1 that are necessary for the effects of TGFβ1-signalling in SMCs. A systematic integrative target discovery platform was employed to identify a robust signature of the effects of TGFβ1 effect in SMCs, using primary human vascular SMCs (VSMCs) obtained from several individuals.

Example 1: Patient Cohort and VSMC Preparation

Patients aged ≥21 and ≤81 undergoing coronary artery bypass grafting (CABG) at the National Heart Centre Singapore were recruited to the study. Patients with valvular heart disease or previous atrial intervention were excluded. The aortic button (AB) and left internal mammary artery (LIMA) tissues were harvested and samples used to outgrow primary vascular smooth muscle cells (VSMCs) by explant-culture method. Biopsies of the aortic button and/or left internal mammary artery were obtained from 15 patients (AB: n=6; LIMA: n=11) undergoing CABG. VSMCs were then prepared from these samples as follows.

AB and LIMA biopsies were collected from CABG patients at the time of open chest surgery. The tunica adventitial layer was removed and the endothelium was gently scraped with forceps, tunica media layer was minced into 1-2 mm³ pieces, and placed in 6 cm dishes. The spacing between adjacent tissues was around 5 mm. Human VSMCs were cultured in vitro in M231 medium (M-231-500, Life Technologies) supplemented with smooth muscle growth supplement (SMGS; S-007-25, Life Technologies) and 1% antibiotic-antimycotic (15240062, Life Technologies), in a humidified atmosphere at 37° C. and 95% air/5% $CO_2$. Cell culture medium was changed with fresh medium every 2-3 days to remove cell debris and to maintain a physiological pH. At 80-90% confluence, cells were passaged by detachment with accutase (A6964, Sigma-Aldrich) using standard cell dissociation techniques. At passage 1-2, fibroblasts and endothelial cells were depleted from the cell cultures by magnetic separation with LD columns (130-042-901, Miltenyi Biotec) using micro-beads tagged with either CD90 (Thy-1, 130-096-253, Miltenyi Biotec) for fibroblast depletion, and CD144 (VE-Cadherin, 130-097-857, Miltenyi Biotec) for endothelial cell depletion. The negatively selected VSMCs remaining in the culture were used in further passaging. All experiments were carried out at low cell passages (SP4) and cells were synchronised in serum-starved with 0.2% fetal bovine serum (10500064, Life Technologies) in M231 basal media for 16 h prior to treatment in serum-free M231 medium.

Molecular and cellular phenotyping was performed to characterize the VSMC transition driven by TGFβ1-stimulation, and the results were integrated with large databases of gene expression in human tissues (GTEx[61]) and cell types (FANTOM[62]).

Example 2: RNA-Seq Analysis

RNA-seq analysis was performed on different cell types as follows.

Total RNA was isolated using Trizol Plus RNA mini kit (12183555, Life Technologies). RNA was quantified using Qubit RNA high sensitivity assay kit (Life Technologies) and assessed for degradation based on RNA integrity number (RIN) using the LabChip GX RNA Assay Reagent Kit (Perkin Elmer). TruSeq Stranded mRNA Library Prep kit (Illumina) was used to assess transcript abundance following standard instructions from the manufacturer. Briefly, poly (A)+ RNA was purified from 0.8-1 ug of total RNA with RIN>7, fragmented, and used for cDNA synthesis, followed by 3' adenylation, adaptor ligation, and PCR amplification. The final libraries were quantified using KAPA library quantification kits (KAPA Biosystems) on StepOnePlus Real-Time PCR system (Applied Biosystems) according to manufacturer's guide. The quality and average fragment size of the final libraries were determined using LabChip GX DNA High Sensitivity Reagent Kit (Perkin Elmer). Libraries were pooled and sequenced on a NextSeq 500 benchtop sequencer using 75-bp paired-end sequencing chemistry.

Raw sequencing data (.bcl files) were demultiplexed into individual FastQ read files with Illumina's bcl2fastq v2.16.0.10 based on unique index pairs. The adaptor sequences and low quality reads/bases were trimmed using Trimmomatic v0.36[6] and the read quality was assessed using FastQC v0.11.5. High-quality reads were mapped to Ensembl human GRCh38 v86 ref or mouse GRCm38 v86 reference genome using Spliced Transcripts Alignment to a Reference (STAR) v2.5.2b[7]. STAR alignment options were selected based on parameters used in ENCODE project. Strand-specific raw counts of uniquely mapped reads (paired-end) were summarized with featureCounts[8] to get gene-level quantification of genomic features: featureCounts -t exon -g gene_id -s 2-p. Differential expression (DE) was performed with DESeq2 v1.14.1 by using raw read counts from featureCounts. We performed a minimal pre-filtering to remove genes that have no reads or only 1 read across all samples to reduce the data size and speed up the analysis process. Sample IDs were included as covariates in DESeq2 design formula to remove batch effect due to samples and increase the sensitivity for finding differences among the conditions. Basal condition was always used as the reference level for pairwise comparison. Shrinkage MA-plot was generated to show the log 2 fold changes over the mean of normalized counts and points will be colored red if adjusted p value was less than 0.1.

Primary human VSMCs were sequenced to a depth of ~20M reads per sample. The vast majority of reads mapped to a unique position of the genome. Uniquely aligning reads were counted to assess the expression level of all annotated genes (FIG. 1).

Example 3: Validation of VSMC Culture Purity

To ensure the purity of the VSMC culture, Principal Component Analysis (PCA) was performed in which the RNA-seq data obtained for VSMC cultures (not stimulated with TGFβ1) was compared with RNA-seq data generated from primary cardiac fibroblasts (FIB) and human umbilical vein endothelial cells (EC).

Primary human fibroblasts were obtained using the explant method with atrial biopsies from the right atrium of patients (n=84) undergoing CABG procedure. Human cardiac fibroblasts (FIB) were prepared as follows: right atrial biopsies were weighed, minced into 1-2 mm³ pieces, and placed in 6 cm dishes. Human FIBs were grown and maintained in DMEM (Life technologies) supplemented with 20% fetal bovine serum (FBS, Hyclone) and 1% penicillin/streptomycin (Gibco), in a humidified atmosphere at 37° C. and 5% $CO_2$. Fresh medium was renewed every 2-3 days. At 80-90% confluence, cells were passaged using standard trypsinization techniques. All experiments were carried out at low cell passage (<P4) and cells were cultured in serum-free DMEM media for 16 h prior to treatment.

Figure 2:
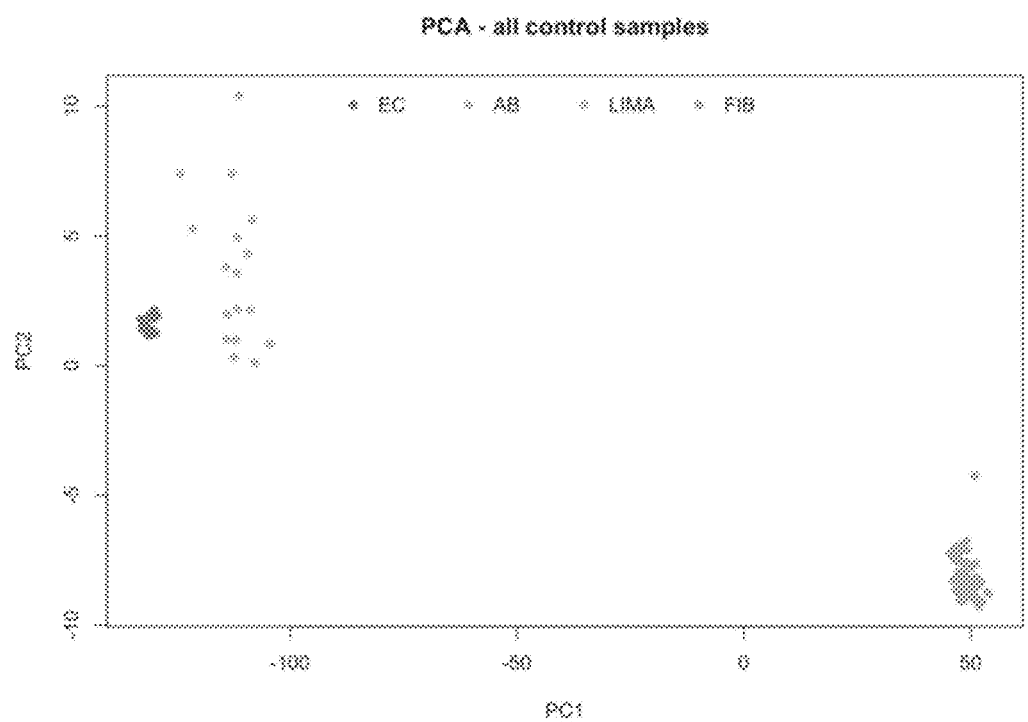
FIG. 2. Graph showing the results of principal component analysis of transcript levels of RNA-seq data from primary human AB (n=6) and LIMA (n=11) derived VSMCs, atrial fibroblasts (FIB; n=84) and endothelial cells (EC; n=17).
Figure 3A:
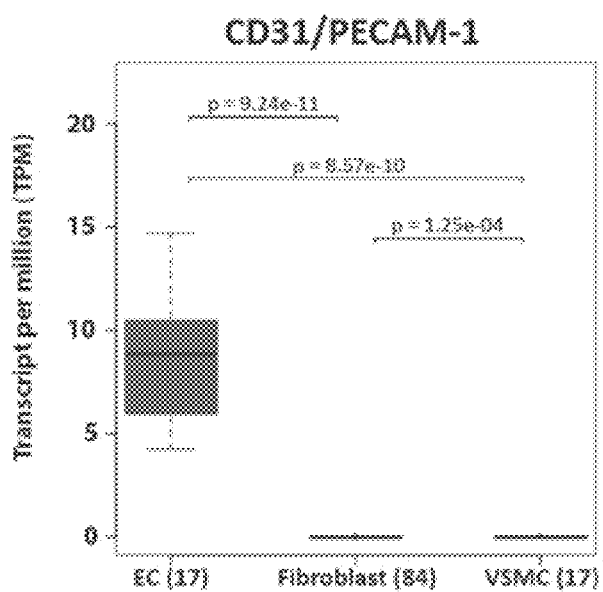
FIGS. 3A to 3D. Graphs showing RNA expression of (FIG. 3A) CD31 (EC marker), (FIG. 3B) THY-1 (Fibroblast marker), (FIG. 3C) elastin and (FIG. 3D) fibulin (VSMC markers), as determined by RNA-seq analysis [Mann-Whitney U test, 2-sided; Median, 10th-90th Percentile].
Figure 3B:
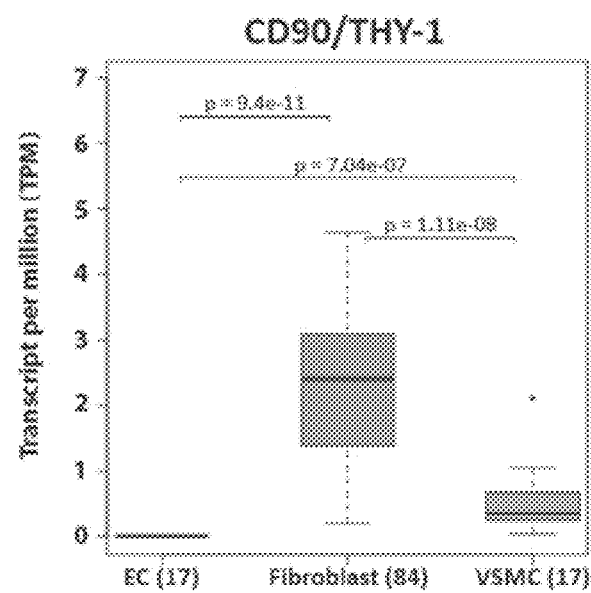
Figure 3C:
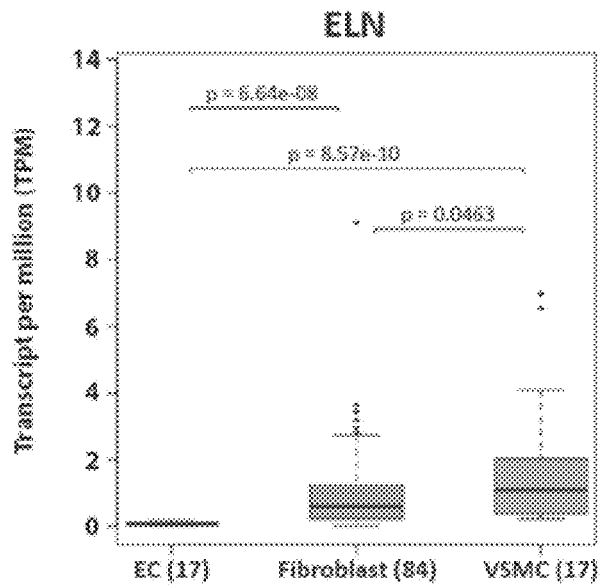
Figure 3D:
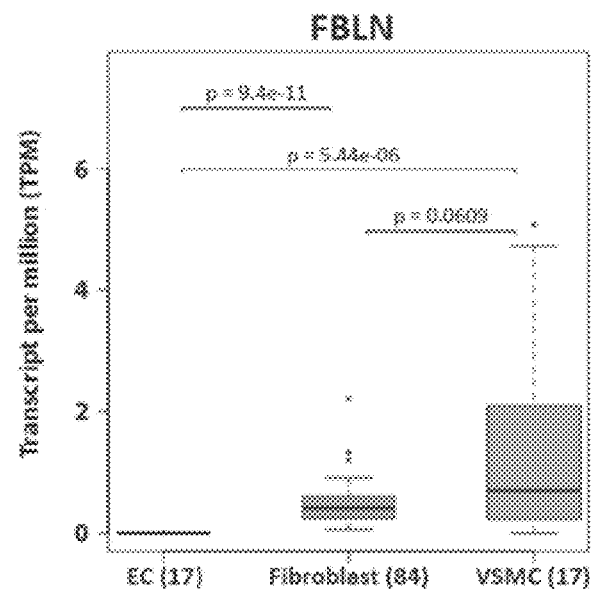

Human umbilical vein endothelial cells (EC) were sourced from Lonza (CC-2519). ECs were grown and maintained in 10 cm dishes with EGM-2 Bullet Kit medium (Lonza, CC-3162), in a humidified atmosphere at 37° C. and 5% $CO_2$. Fresh medium was renewed every 2-3 days. At 80-90% confluence, cells were passaged using standard trypsinization techniques. All experiments were carried out at low cell passage (<P4) and cells were cultured in serum-free EBM-2 basal media for 16 h prior to treatment. The results of the principal component analysis are shown in FIG. 2. Cell types were found to cluster into distinct groups, demonstrating that ensuring that AB and LIMA VSMC cultures were not ECs or FIBs. The analysis also showed that VSMCs derived from AB or LIMA are dissimilar.

Analysis of RNA expression levels of marker genes for ECs, FIBs and VSMCs also confirmed the results of the PCA: CD31, an endothelial cell marker gene, was highly expressed in the ECs, but not in VSMCs or FIB cultures. This further confirmed that ECs were not present in the VSMC cultures. VSMCs also express lower levels of THY-1, a fibroblast marker, and higher levels of the vascular smooth muscle markers ELN and FBLN as compared to the other cell types (FIGS. 3A to 3D).

Figure 4:
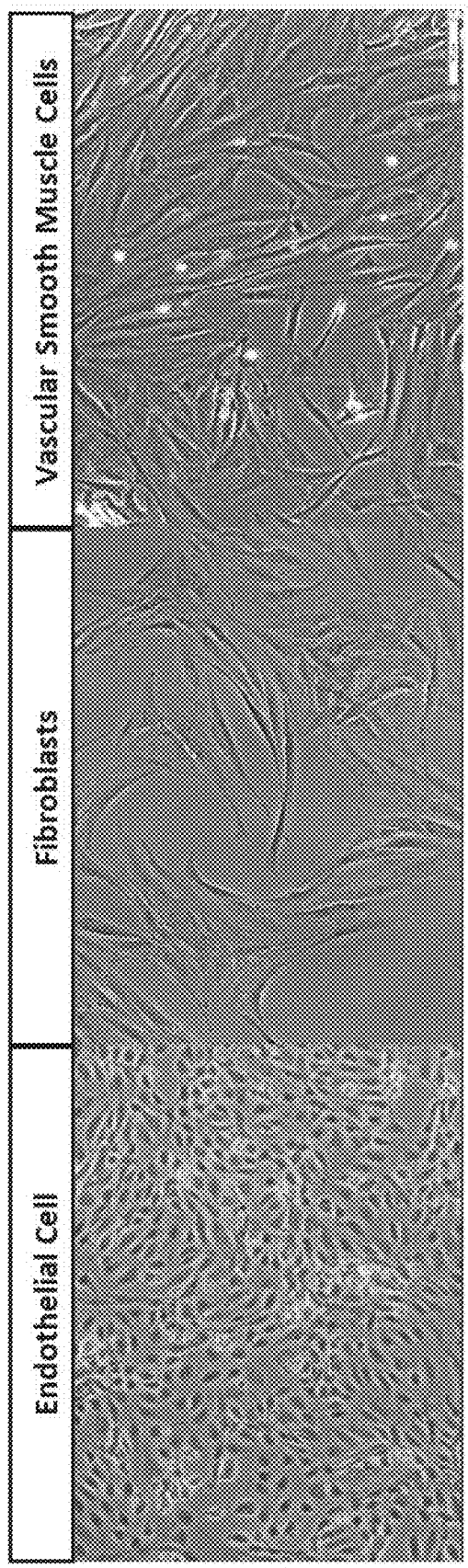
FIG. 4. Representative microscopic images of primary human VSMCs, atrial fibroblasts and endothelial cells in culture. White bar represents 100 μm.

FIG. 4 moreover demonstrates morphological differences between ECs, fibroblasts and VSMCs as determined by microscopy. Taken together, FIGS. 2, 3 and 4 demonstrate that the following studies were obtained using pure cultures of primary human VSMCs.

Figure 5:
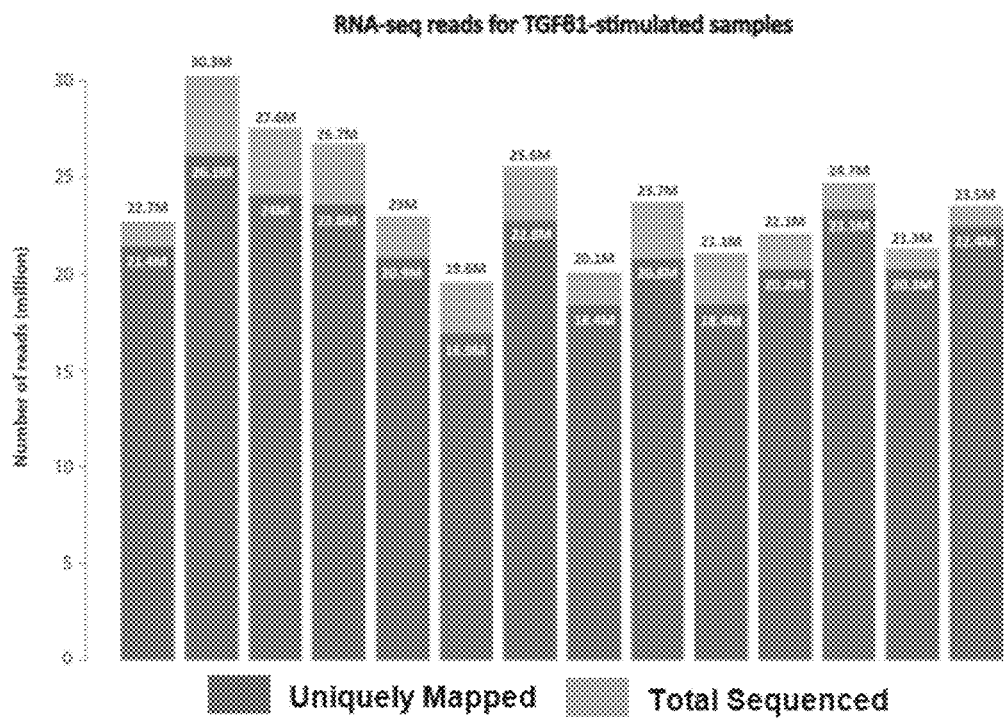
FIG. 5. Bar chart showing RNA-seq of TGFβ1-stimulated human VSMCs. The bars indicate the number of reads generated per sample (n=14). Close to 20 million total reads were generated per sample to analyse RNA expression on a genome-wide scale.
Figure 6A:
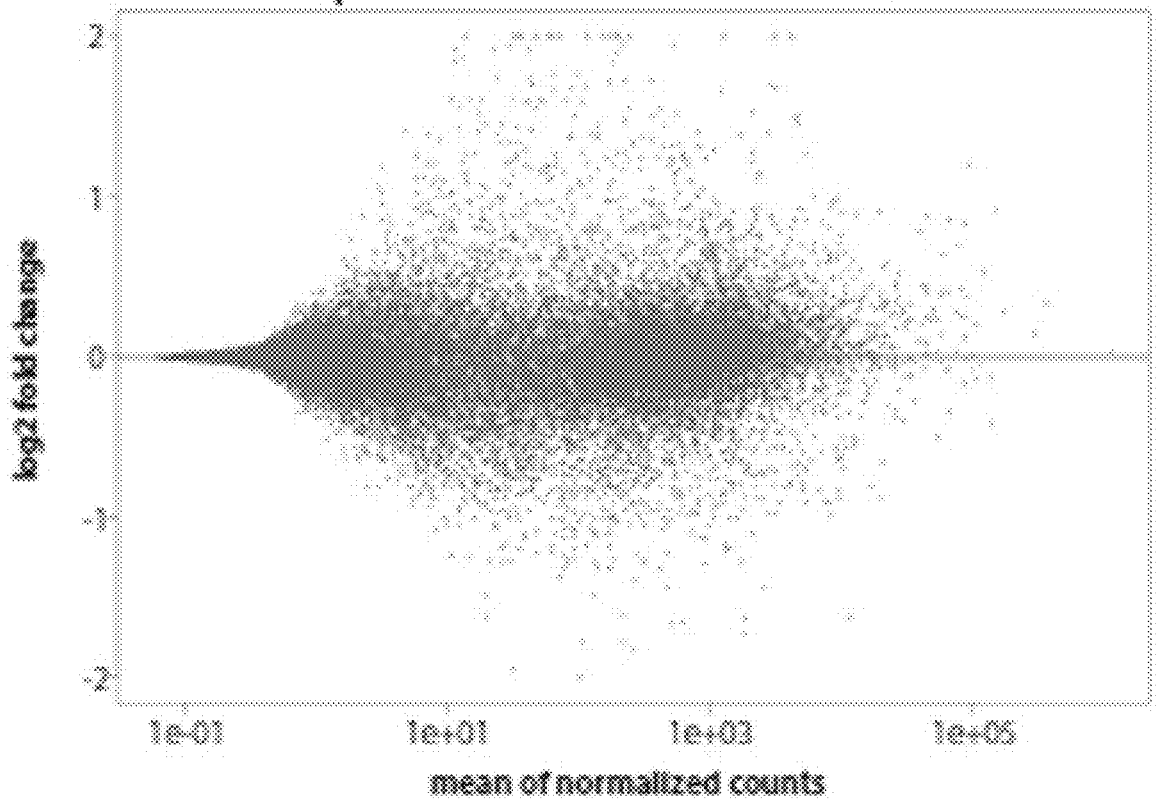
FIGS. 6A to 6D. Graphs and charts showing RNA expression signatures of unstimulated and TGFβ1-stimulated human VSMCs from AB and LIMA.
Figure 6B:
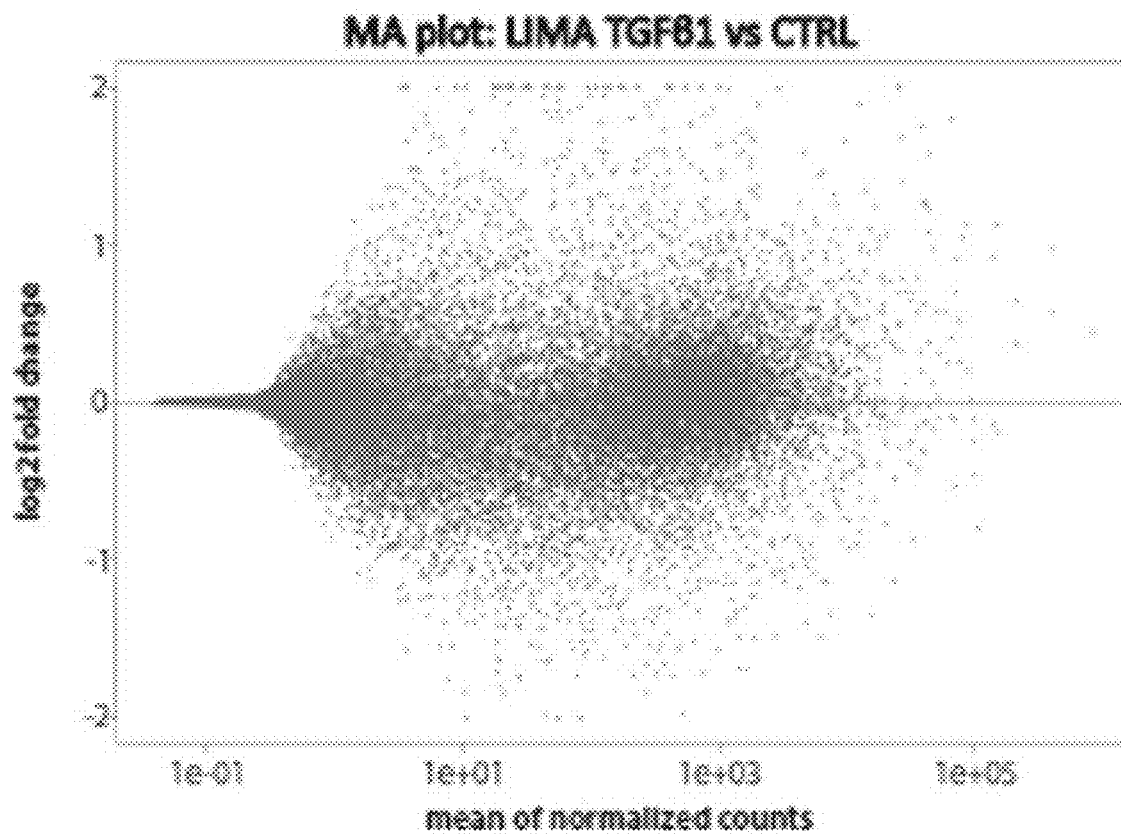
Figure 6C:
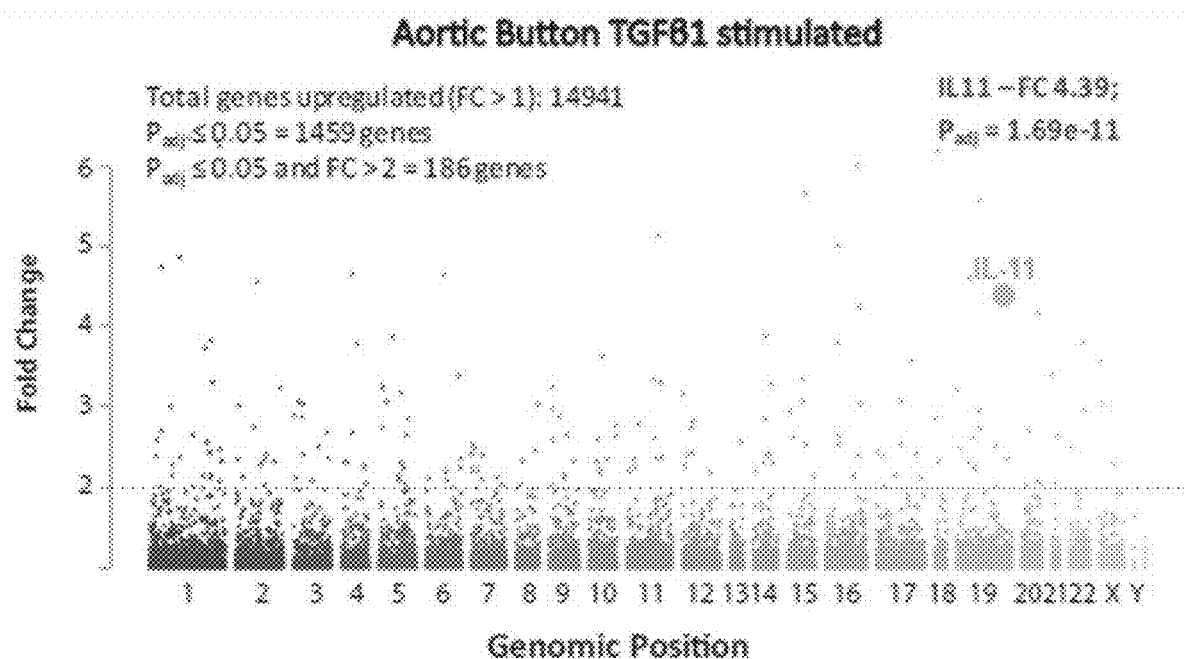
Figure 6D:
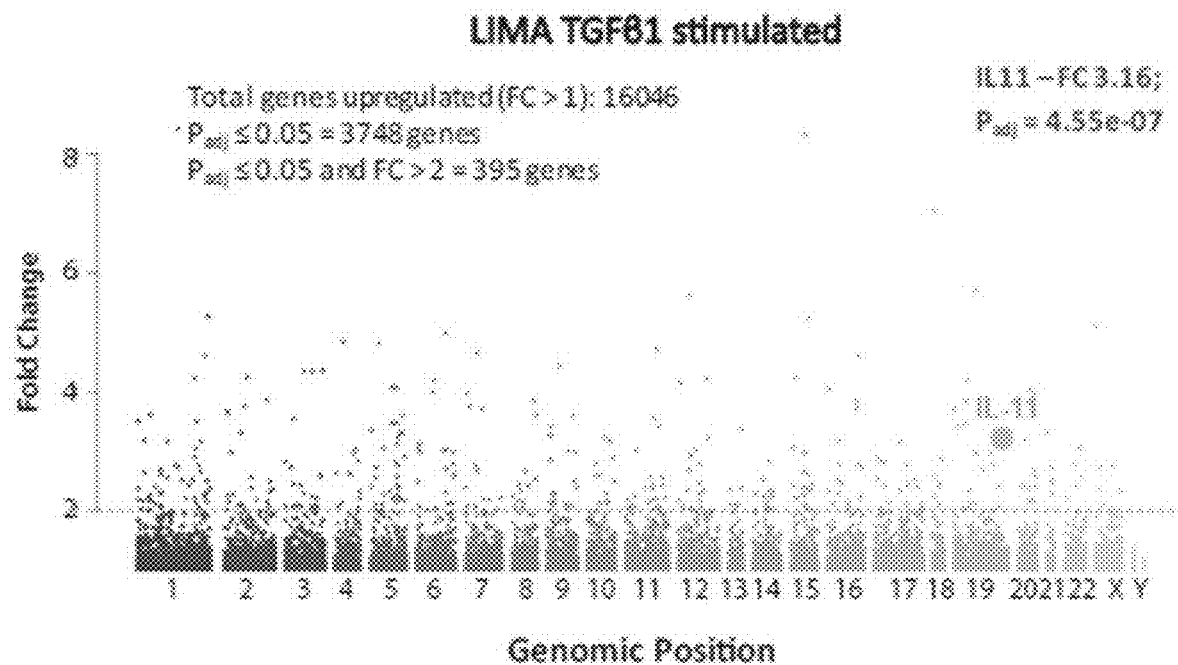

Example 4: RNA-Seq Analysis of Changes in RNA Expression Associated with TGFβ1 Signalling RNA-seq analysis was performed on both baseline and TGFβ1 stimulated VSMCs from the AB and LIMA at early passages 3-4 to assess genome-wide changes in RNA expression in response to TGFβ1 signalling. VSMCs were stimulated with TGFβ1 (5 ng/ml; 24 hours) and performed RNA-seq analysis was performed as described in Example 2 (FIG. 5).

RNA transcript levels were then compared between TGFβ1-stimulated and unstimulated VSMCs to identify genes that had their expression upregulated by stimulation with TGFβ1. Uniquely aligning reads were counted for each gene locus and differential expression was detected using the DEseq2[63] package.

The results of the analysis are shown in FIG. 6. IL-11 was found to be upregulated significantly in VSMCs derived from AB and LIMA in response to TGFβ1 stimulation (FC 4.39 and FC 3.16 respectively; adjusted P-values=$1.69^{e-11}$ and $4.55^{e-07}$ respectively). This highly significant upregulation of IL-11 in both AB and LIMA derived VSMCs confirmed that TGFβ 1 upregulates IL-11 at the RNA level across different types of VSMCs and in several individuals.

Figure 7:
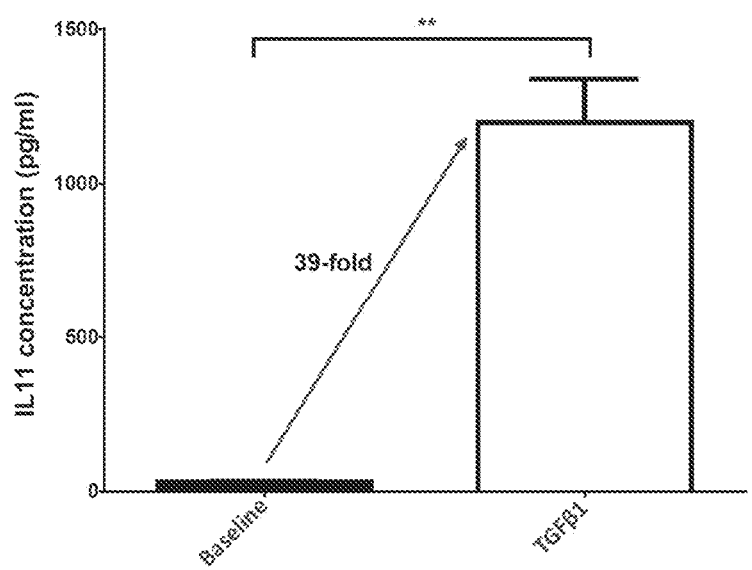
FIG. 7. Bar chart showing TGFβ1-induced upregulation of IL-11 secretion by VSMCs. VSMCs were unstimulated, or were incubated with TGFβ 1 (5 ng/ml, 24 h) and the collected supernatant was analysed by ELISA to determine the level of IL-11 (n=3). Data expressed as mean±SD, $P<0.01$ by two-sided paired sample T-test.

The inventors then confirmed that this robust signature of IL-11 upregulation also occurred at the protein level by performing ELISA analysis on cell culture supernatant obtained from unstimulated VSMCs, and VSMCs stimulated with TGFβ1 (5 ng/ml, 24 h), for 3 replicates. A 39-fold increase in IL-11 was detected in the cell culture supernatant of VSMCs stimulated with TGFβ1 (FIG. 7). The fact that the increase in secreted IL-11 induced by stimulation with TGFβ1 was larger than the increase in IL-11 RNA levels (compare FIGS. 6C and 6D with FIG. 7) suggests that TGFβ1 may influence IL-11 levels through post-transcriptional regulation.

Example 5: Analysis of Targets for IL-11

To explore whether IL-11 secreted by VMSCs in response to stimulation with TGFβ1 acts on VMSCs or only signals to other cell types in the proximity, expression of IL-11 receptor α (IL-11RA) was analysed across 500+ cell lines in the PHANTOM[62] catalogue.

Expression levels of all genes in primary cell types with replicates were downloaded from FANTOM5[62] web resource (119 cell types). Since the FANTOM5 data is at the level of transcription start site (TSS) expression derived from CAGE sequencing gene expression was calculated by summing all counts that were assigned to a given gene. These were then normalised by library size in order to calculate the TPM for each gene. In order to compare the expression profiles of IL-11RA and IL-6R the TPM for these two genes were extracted across different primary cell samples that covered cell types from all lineages. In each case, where the expression of either IL-11RA or IL-6R was above the level of noise these cell types were highlighted and categorized them as described in the FANTOM5 cell type ontology.

Figure 8:
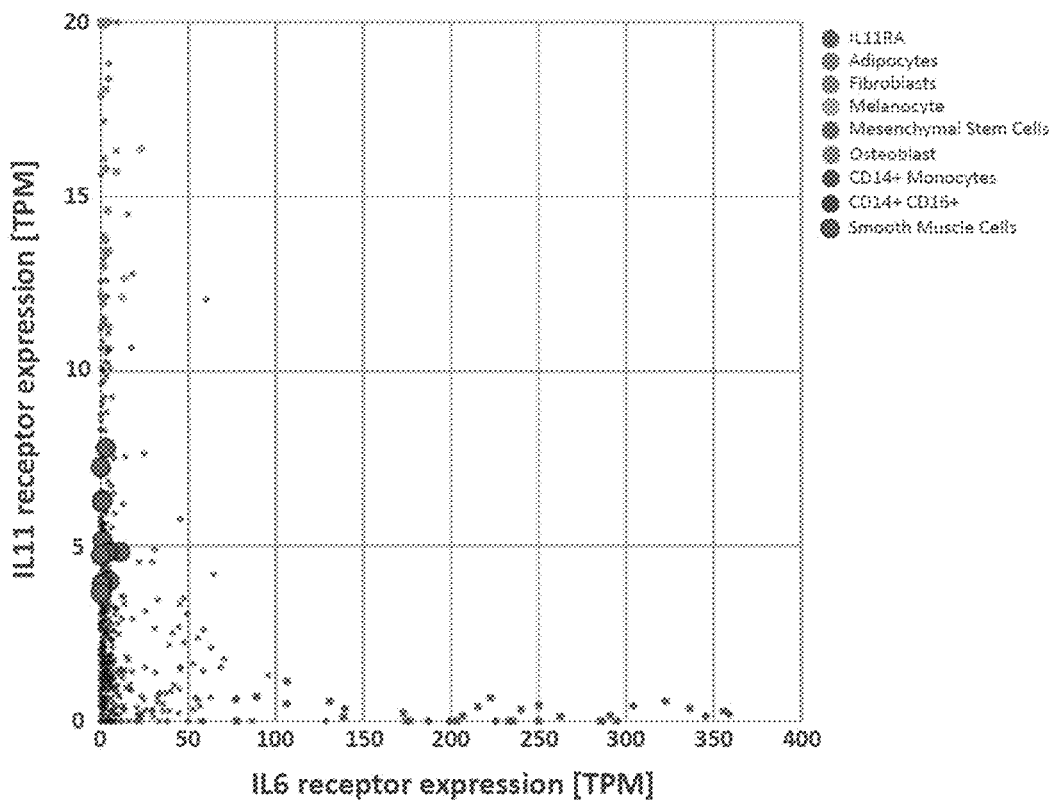
FIG. 8. Graph showing expression of IL-11 receptor (IL-11RA) and IL-6 receptor (IL-6R) in 500+ cell types. Large circles highlight IL-11 receptor expression by smooth muscle cells.

The results are shown in FIG. 8. It was found that cells tended to express either the IL-11 receptor or the IL-6 receptor, but rarely both together. IL-6 receptor expression was mostly on immune cells, whereas IL-11 receptor expression was detected mesenchymal lineage and smooth muscle cells (highlighted in FIG. 8).

Example 6: Production of IL-11 by VSMCs in Response to Stimulation with IL-11

Several smooth muscle cell lines express IL-11 receptor, implying that IL-11 is not only secreted, but also has a direct effect on VSMCs. This suggests the possibility for an autocrine IL-11 loop, if IL-11 induces its own expression on VSMCs. To test this hypothesis, an IL-11:IL-11RA fusion protein referred to as hyper IL-11[64] was prepared by recombinant DNA and protein expression techniques. Hyper IL-11 was constructed using fragment of IL-11 RA (amino acid residues 1 to 317 consisting of domain 1 to 3; UniProtKB: 014626) and IL-11 (amino acid residues 22 to 199 of UniProtKB: P20809) with a 20 amino acid long linker (SEQ ID NO:5). The amino acid sequence for Hyper IL-11 is shown in SEQ ID NO:4.

Figure 9:
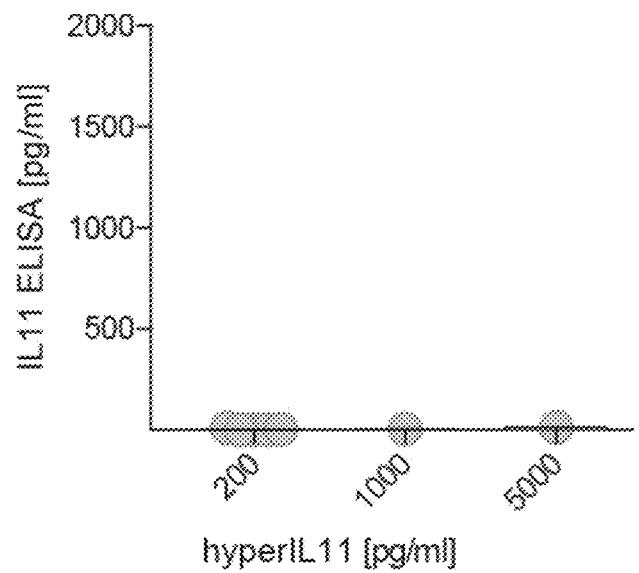
FIG. 9. Graph showing that hyper IL-11 is not detected by ELISA for IL-11. Recombinant hyper IL1 1 was added to wells of an ELISA plate at varying concentrations and subsequently measured using a commercially available ELISA for the detection of IL-11.

Hyper IL-11 is a powerful stimulator of IL-11 signalling, similar to the IL-6:IL-6R fusion protein described in Lokau et al., Cell Reports (2016) 14, 1761-1773. The inventors confirmed that the ELISA used for the detection of soluble secreted IL-11 does not recognize hyper IL-11 (FIG. 9). Briefly, IL-11 levels in equal volumes of cell culture media were added to wells of an ELISA plate, and IL-11 was quantified using the Human IL-11 Quantikine ELISA kit (D1100, R&D Systems) as per manufacturer's protocol.

The inventors then used the same ELISA kit to analyse IL-11 secretion into the cell culture medium of VSMCs stimulated with hyper IL-11. Briefly, VSMCs were cultured in the presence of 0.2, 0.5, and 1 ng/ml, hyper IL-11 for 24 h, and the cell culture supernatant was subsequently analysed for IL-11 using the Human IL-11 Quantikine ELISA kit. In this way, the inventors were able to determine whether IL-11-mediated signalling in VSMCs (triggered by hyper IL-11) results in the production of IL-11 by VSMCs in an autocrine fashion.

Figure 10:
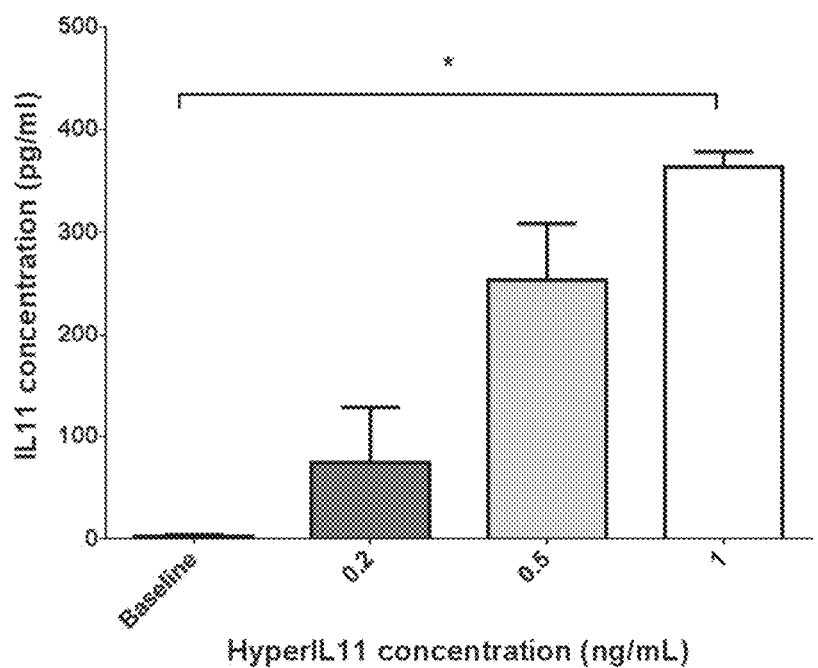
FIG. 10. Bar chart showing that Hyper IL-11 induces IL-11 secretion by VSMCs. VSMCs were incubated with increasing doses of hyper IL-11 and at the end of the experiment cell culture supernatant was analysed for IL-11 in 2 biological replicates. Data expressed as mean±SD, comparison by one-way ANOVA with Dunnett's multiple comparison. *=$P<0.05$.

The results are shown in FIG. 10. Hyper IL-11 was found to induce secretion of IL-11 by VSMCs, in a dose-dependent manner.

Example 7: Effect of IL-11 Stimulation on Gene Expression by VSMCs

The inventors next analysed the effects of IL-11 stimulation on RNA expression by VSMCs. Human AB and LIMA VSMCs were cultured for 24 h in the presence of 5 ng/ml recombinant human interleukin-11 (IL-11; PHC0115, Life Technologies), and RNA seq analysis was then performed as described in Example 2.

Figure 11:
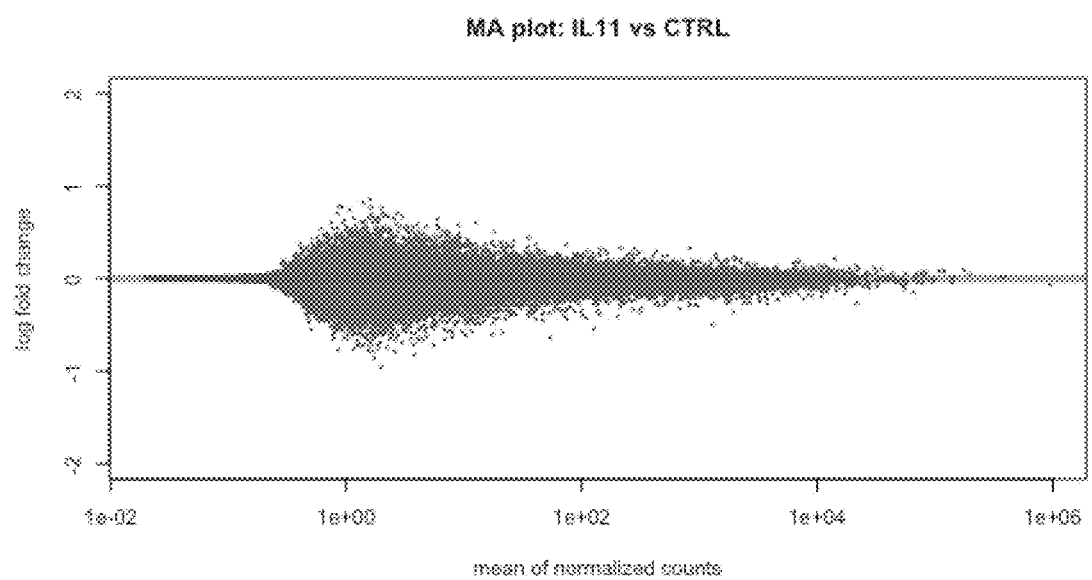
FIG. 11. Graph showing RNA expression signatures of unstimulated and IL-11-stimulated human VSMCs from AB and LIMA. The analysis is based on pooled biological replicates from the AB VSMCs (n=7) and LIMA VSMCs (n=11). MA plot demonstrates DEseq2-corrected log 2 fold changes over the mean of normalized count.
Figure 12A:
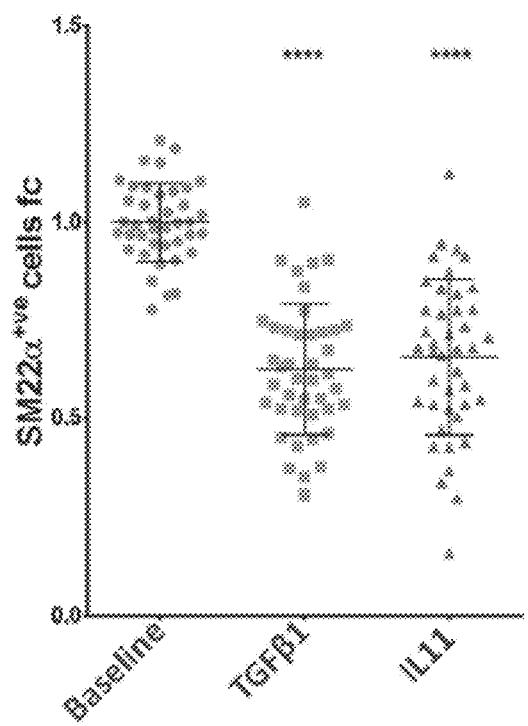
FIGS. 12A to 12E. Graphs and photographs showing the effect of TGFβ 1 and IL-11 stimulation on the expression of markers of VSMC contractile and secretory phenotypes. VSMCs were unstimulated, or were cultured in the presence of TGFβ 1 (5 ng/ml, 24 h) or IL-11 (5 ng/ml, 24 h). Cells were analysed by fluorescence and automated quantification of images in 4 biological replicates.
Figure 12B:
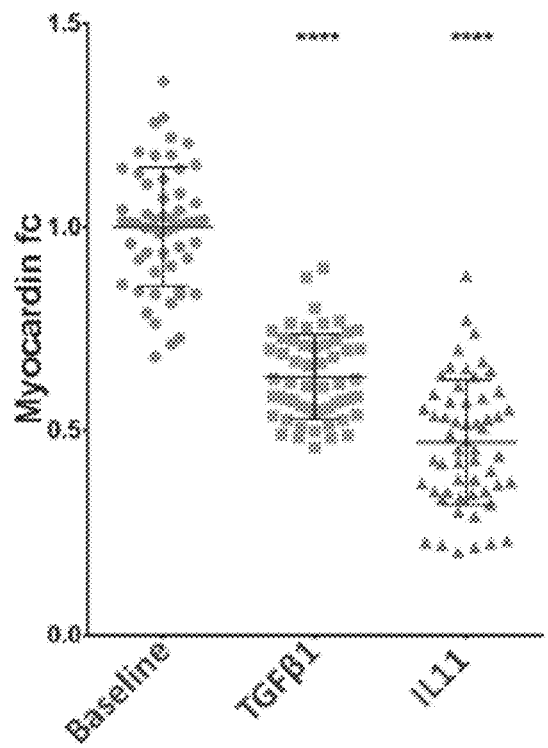
Figure 12C:
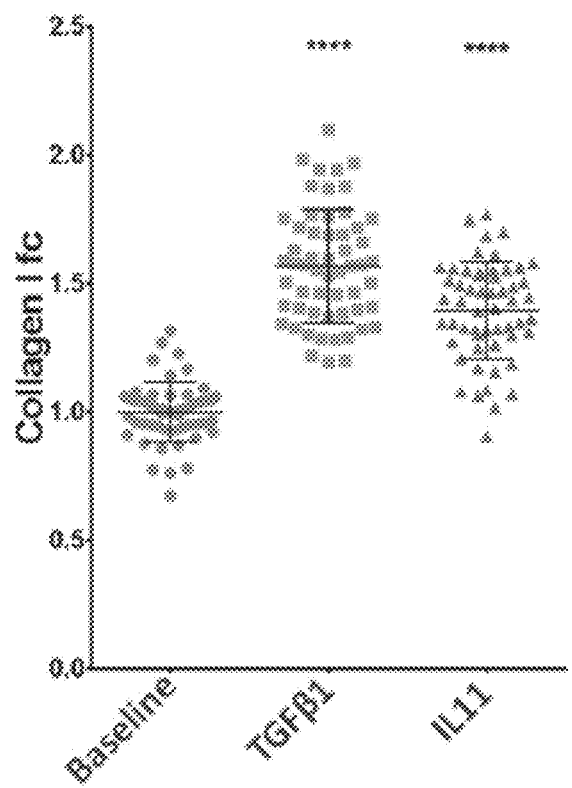
Figure 12D:
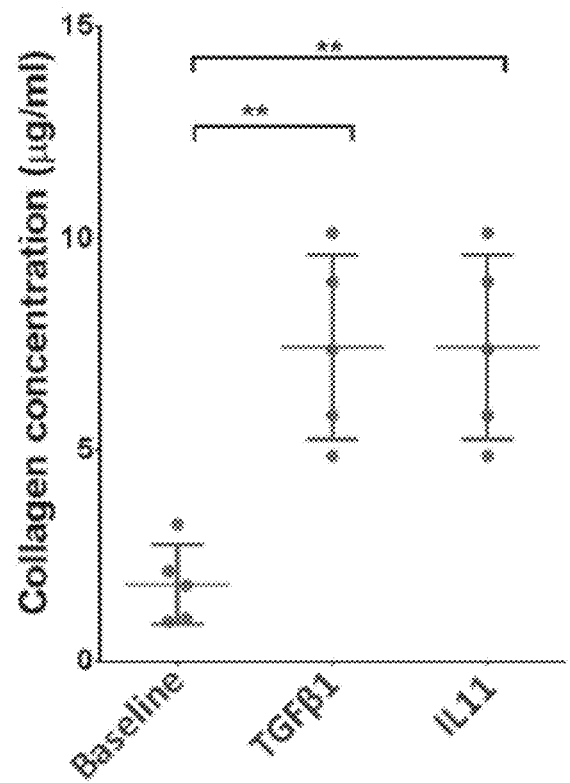
Figure 12E:
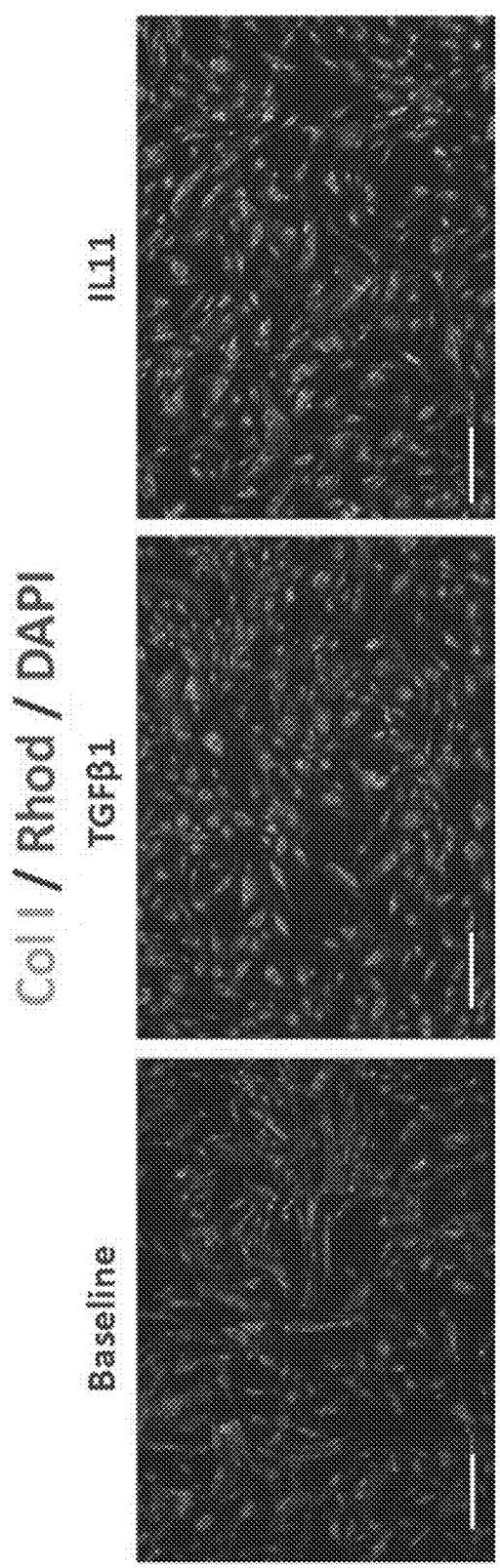

The results are shown in FIG. 11. IL-11 was found not to induce a strong transcriptional response in VSMCs. Moreover, stimulation with IL-11 did not strongly upregulate expression or IL-11 RNA, suggesting that increased IL-11 protein expression in response to treatment with IL-11 (FIG. 10) is achieved through post-transcriptional regulation.

Example 8: Effect of IL-11 Treatment on VSMC Phenotype

The inventors then further explored the effect of IL-11 on VSMCs phenotype and activity by analysis for markers of the different SMC phenotypes using the Operetta platform.

VSMCs were seeded in 96-well black CellCarrier plates (Perkin-Elmer) at a density of $1\times10^4$ cells/well and incubated in media for 24 h. Cells were then cultured without stimulation, or stimulated by culture for 24 h with TGFβ1 (5 ng/ml), IL-11 (5 ng/ml). Cells were subsequently rinsed in phosphate-buffered saline (PBS) and fixed in 4% paraformaldehyde (28908, Life Technologies) for 15 m. Cells were permeabilized with 0.1% Triton X-100 (Sigma-Aldrich) in PBS for 10 m, and rinsed in PBS and wash buffer (0.25% BSA and 0.1% Tween-20 in PBS). Non-specific sites were blocked using wash buffer with addition of 0.25% BSA (blocking solution; 30 m). Cells were incubated overnight at 4° C. with antibodies: transgelin (SM22α, 1:200; AB14106, Abcam), collagen I (Col1, 1:500; AB292, Abcam), myocardin (MYOCD, 1:200; AB203614, Abcam). All primary antibodies were diluted in blocking solution. Following wash buffer rinses, cells were incubated with goat anti-mouse (AB150113, Abcam) or anti-rabbit (AB150077, Abcam) AF488 for 1 h at room temperature (RT) in the dark. Secondary antibodies were diluted 1:1000 in blocking solution. Cells were counter-stained with rhodamine-phalloidin (1:1000, R415, Life Technologies) and DAPI (1 µg/ml, D1306, Life Technologies) in blocking solution (1 h). Plates were scanned and images were collected with an Operetta high-content imaging system 1438 (PerkinElmer) using a 10×objective lens. Each condition was assayed from at least two wells and a minimum of 7 fields per well. The quantification of SM22α positive cells was performed using Harmony software version 3.5.2 (PerkinElmer). The measurement of collagen I and MYOCD fluorescence intensity per area were performed with Columbus 2.7.1 (PerkinElmer).

Deposition of collagen was also analysed using a colorimetric assay. Total secreted collagen in cell culture supernatant was determined using the Sirius red collagen detection kit (9062, Chondrex) in accordance with the manufacturer's instructions.

The results of the experiments are showing FIGS. 12A to 12E. Both TGFβ1 and IL-11 were found to cause reduced expression of markers of the contractile VSMC phenotype (i.e. SM22α, myocardin) and to increase expression of collagen I, a marker of the secretory VSMC phenotype.

The results suggest that IL-11 is a driver of the pathogenic transition of VSMCs from the contractile to the secretory phenotype, and is not a protective response to stimulation with TGFβ1.

Example 9: Effect of IL-11 Treatment on VSMC Migration

An in vitro scratch and Boyden chamber assays were performed to analyse the influence of IL-11 stimulation on VSMCs migration.

In vitro scratch wound assays and Boyden chamber assays were performed in duplicate per patient sample. Scratch wound assays were performed with confluent monolayers of VSMCs. After synchronizing the cells by culture low serum media (M231 containing 0.2% FBS) for 24 h, a linear scratch was created with a sterile pipette tip and cells were treated with: either IL-11 (5 ng/ml) or TGFβ1 (5 ng/ml) for 24 h. The wound area was imaged at 0 and 24 h and migration was calculated using ImageJ software. Briefly, migration of VSMCs was calculated using the formula "migration=(A0-A1)/A0×100", wherein A0 is the area of the wound at 0 h and A1 is the area unoccupied by VSMCs after 24 h. 6 to 10 random regions were analysed per treatment and averaged.

Boyden chamber assays were performed using a Cell Migration Assay kit (CBA-100, Cell Biolabs Inc) as per the manufacturer's protocol. VSMCs ($5 \times 10^4$ cells/well) were seeded inside transwell inserts, and the bottom well of the Boyden chamber contained cell culture medium, or cell culture medium supplemented with either TGFβ1 (5 ng/ml) or IL-11 (5 ng/ml). After 24 h VSMC migration towards the bottom well was determined colorimetrically at OD 560 nm.

Figure 13A:
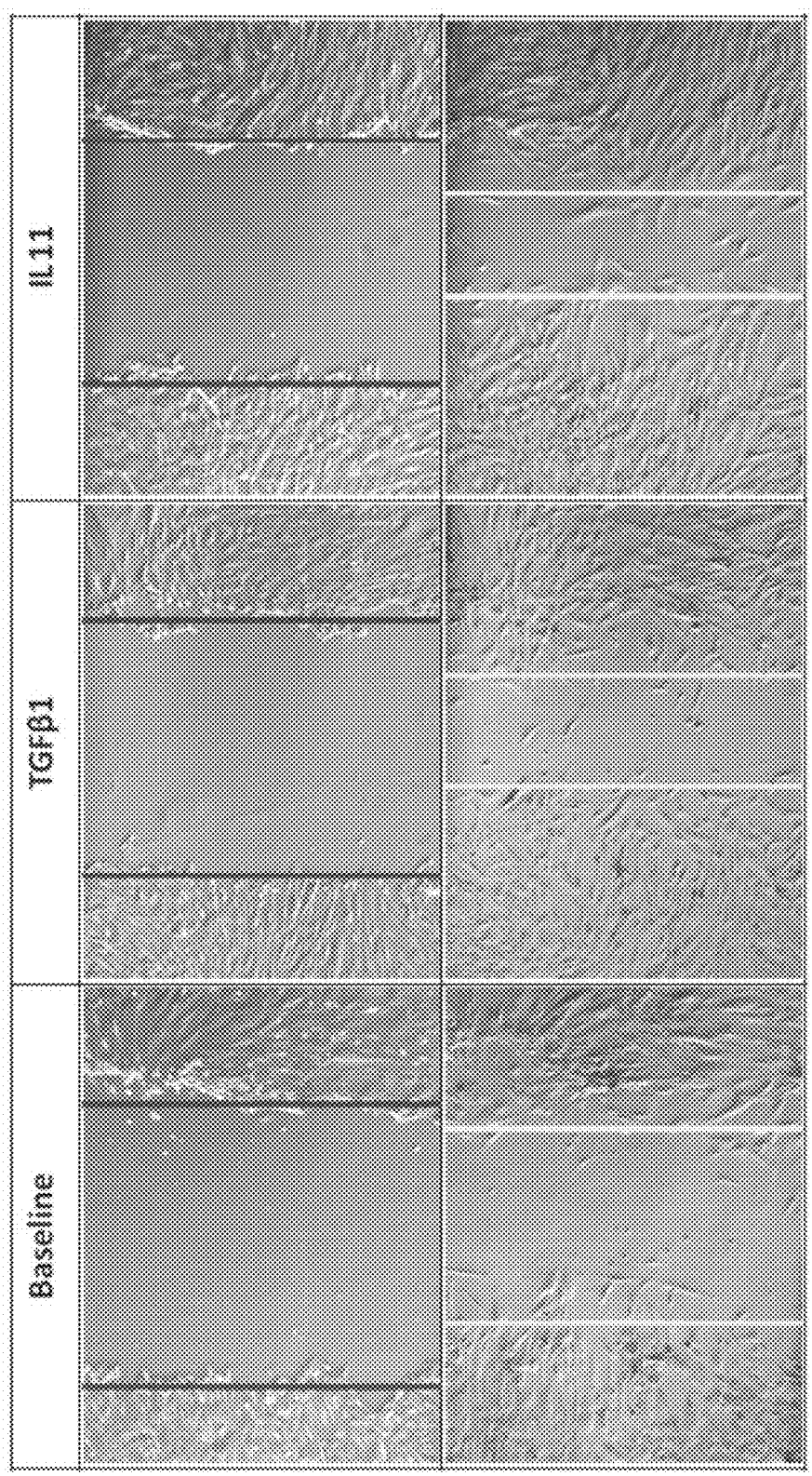
FIGS. 13A and 13B. Photographs (FIG. 13A) and bar chart (FIG. 13B) showing the effects of IL-11 and TGFβ1 on the migration of VSMCs in an in vitro wound healing assay. Scratch wound assays were performed with confluent monolayers of VSMCs. After synchronizing the cells by culture low serum media (M231 containing 0.2% FBS) for 24 h, a linear scratch was created with a sterile pipette tip and cells were either untreated (Baseline), or treated with either IL-11 (5 ng/ml) or TGFβ1 (5 ng/ml) for 24 h. The wound area was imaged at 0 h (upper panels) and 24 h (lower panels), and migration was calculated using ImageJ software. All data expressed as mean±SD. Statistical significance was established with one-way ANOVA with Dunnett's multiple comparisons.
Figure 13B:
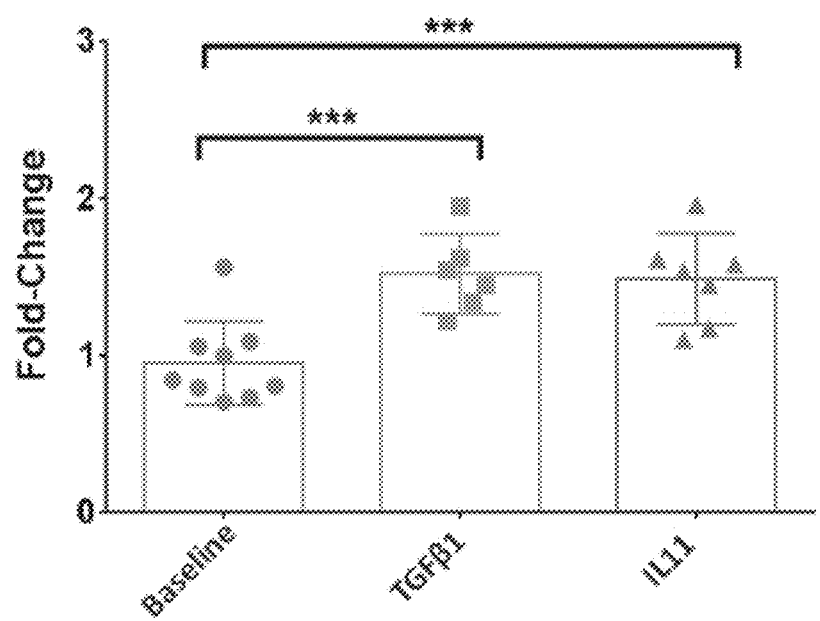
Figure 14A:
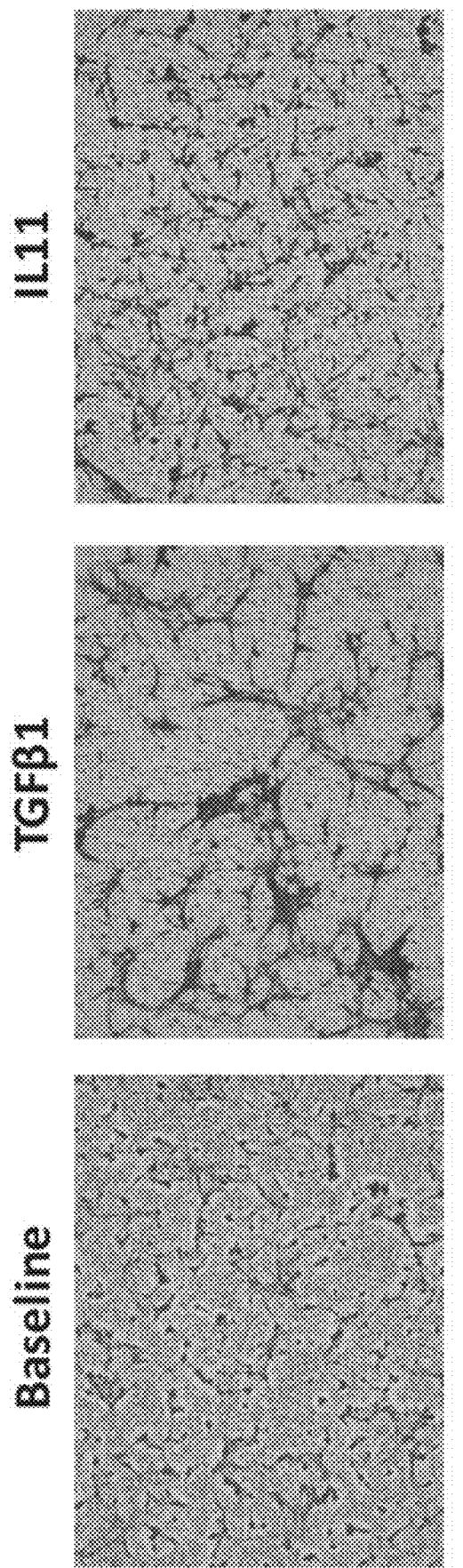
FIGS. 14A and 14B. Photographs (FIG. 14A) and graph (FIG. 14B) showing the effects of IL-11 and TGFβ 1 on the migration of VSMCs in a Boyden chamber assay. VSMC migration towards wells containing unsupplemented cell culture medium (Baseline), or medium containing either IL-11 (5 ng/ml) or TGFβ1 (5 ng/ml) was analysed after 24 h. Symbols in the bar represents biological replicates.
Figure 14B:
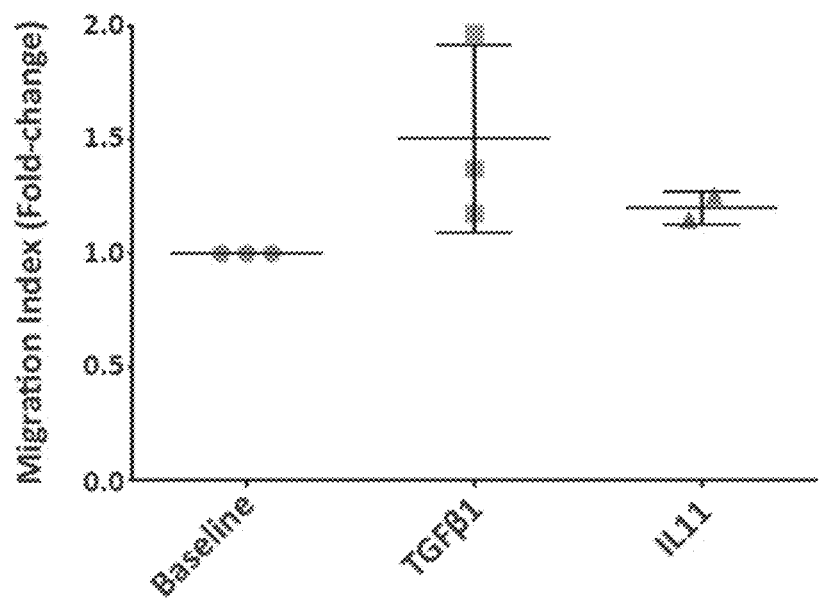

The results of the experiments are shown in FIGS. 13A-B and 14A-B. Treatment with IL-11 or TGFβ1 significantly increased wound closure (FIGS. 13A and 13B). A trend towards increased migration of VSMCs towards compartments containing TGFβ1 or IL-11 was observed (FIGS. 14A and 14B; P=0.15).

To inhibit IL-11 signalling, cells were treated with IL-11 neutralizing antibody (2 μg/mL, MAB218, R&D Systems) or mouse IgG type 2a (2 μg/mL, MAB003, R&D Systems) for 24 h in the presence of TGFβ1.

Example 10: Analysis of the Effect of IL-11 Neutralisation on TGFβ1-Mediated Effects on VSMCs The inventors next investigated whether IL-11 was required for the TGFβ1-mediated effect on VSMC phenotype and activity.

VSMCs were seeded in 96-well black CellCarrier plates and incubated in media for 24 h as described in Example 8. Cells were then cultured without stimulation, or stimulated by culture for 24 h with TGFβ 1 (5 ng/ml), IL-11 (5 ng/ml) in the presence of EdU (10 μM/ml); and in the presence or absence of an IgG control antibody or neutralizing anti-IL-11 antibody (2 μg/ml). Cells were subsequently rinsed, fixed and stained for analysis as described in Example 8. Incorporated EdU was labeled with AlexaFluor (AF) 488 using Click-iT EdU labeling kit (C10350, LifeTechnologies). 100 μl of Click-iT reaction cocktail was used per well and consisted of 85 μl Click-iT reaction buffer, 4 μl copper sulphate, 0.25 μl AF488 azide and 10 μl reaction buffer additive. This cocktail was incubated for 30 m at room temperature, cells washed once with 100 μl of Click-iT reaction rinse buffer. In addition, rinse with wash buffer (0.25% BSA and 0.1% Tween-20 in PBS). Plates were scanned and imaged as described in Example 8. Quantification of EdU positive cells was performed using Harmony software version 3.5.2 (PerkinElmer).

Figure 15A:
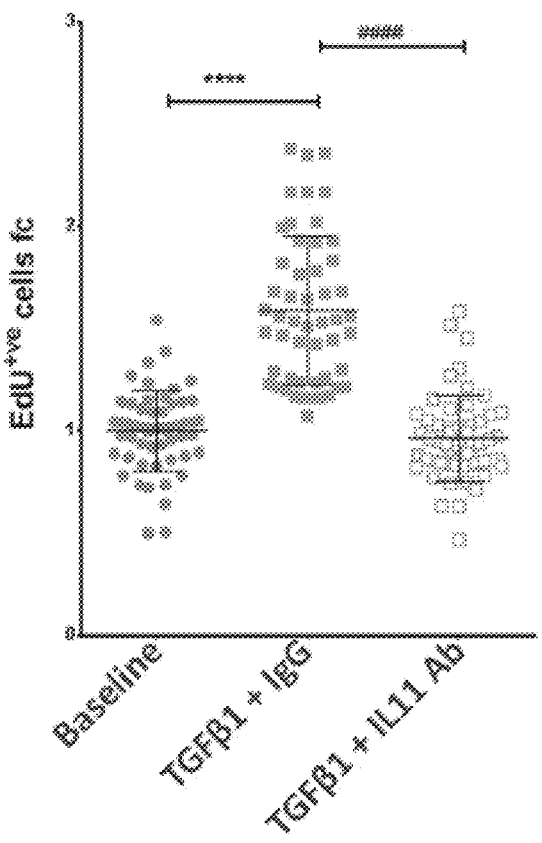
FIGS. 15A to 15C. Graphs showing the effect of neutralisation of IL-11-mediated signalling on TGFβ 1-mediated stimulation on the expression of markers of VSMC contractile and secretory phenotypes. VSMCs were unstimulated, or were cultured in the presence of TGFβ1 (5 ng/ml, 24 h) in the presence or absence of an IgG control antibody or neutralizing anti-IL-11 antibody (2 μg/ml).
Figure 15B:
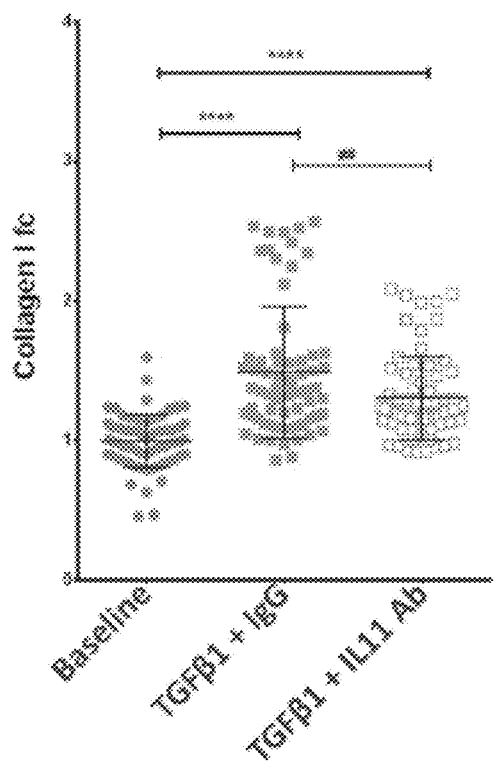
Figure 15C:
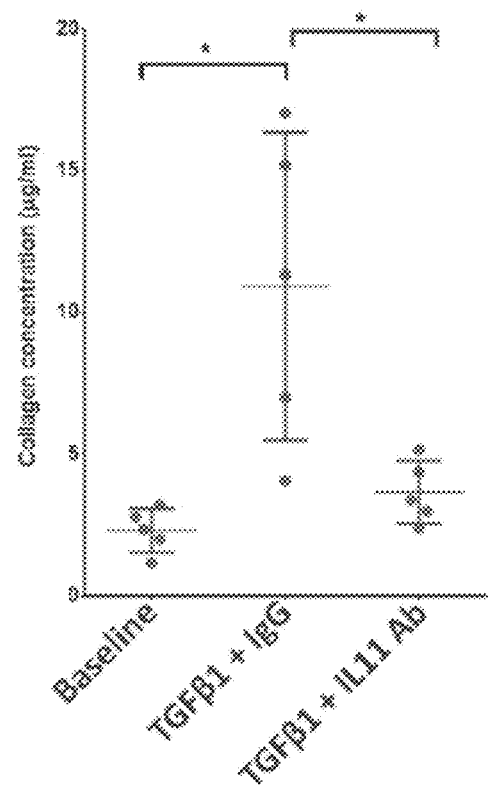

The results are shown in FIGS. 15A to 15C. Inhibition of IL-11-mediated signalling using neutralizing anti-IL-11 antibody was found to inhibit TGFβ1-mediated stimulation of VSMC proliferation (FIG. 15A), and collagen I production (FIGS. 15B and 15C).

In vitro scratch wound assays were performed as described in Example 9, in which cells were treated with either IL-11 (5 ng/ml) or TGFβ1 (5 ng/ml) in the presence of either neutralizing anti-IL-11 antibody (2 μg/ml, MAB218, R&D Systems) or mouse IgG type 2a (2 μg/ml, MAB003, R&D Systems) for 24 h. The wound areas were imaged and analysed as described in Example 9.

Figure 16A:
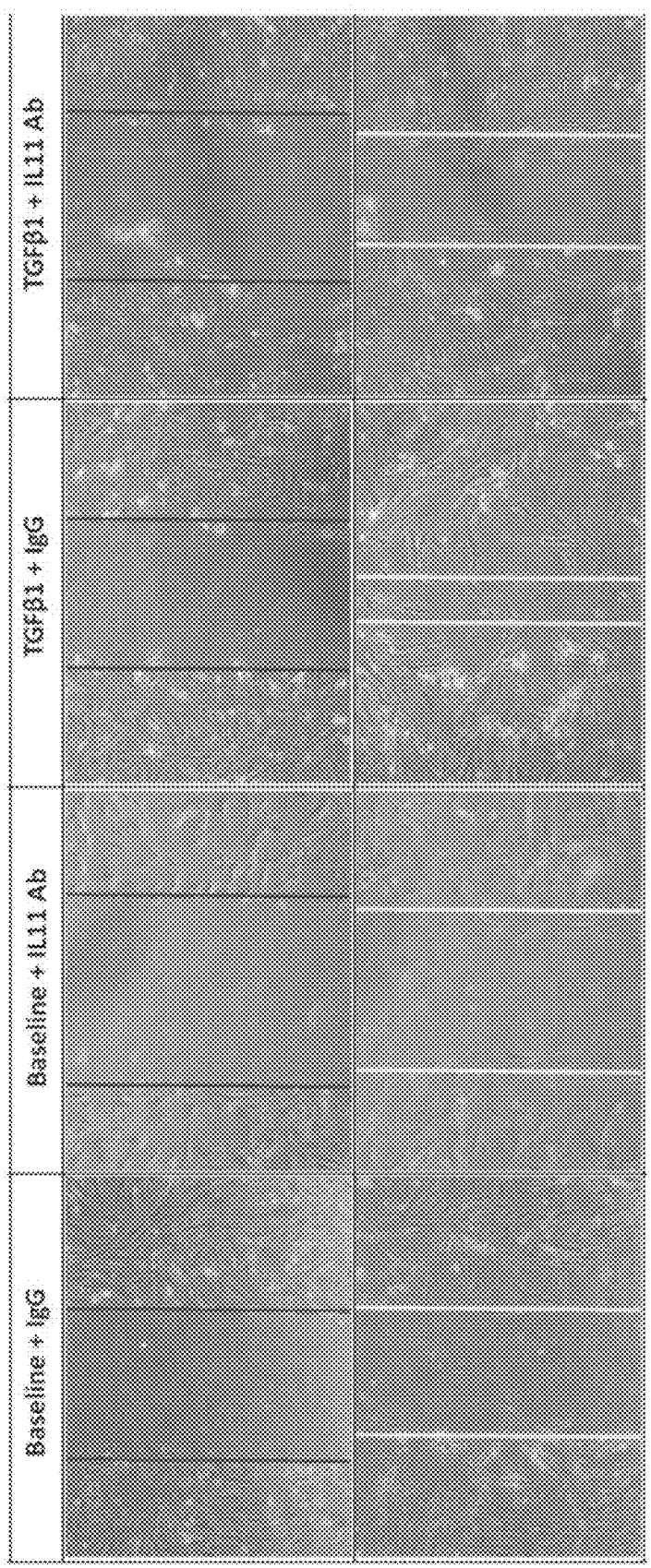
FIGS. 16A and 16B. Photographs (FIG. 16A) and bar chart (FIG. 165) showing the effects of IL-11 and TGFβ 1 on the migration of VSMCs in an in vitro wound healing assay. Scratch wound assays were performed with confluent monolayers of VSMCs. After synchronizing the cells by culture low serum media (M231 containing 0.2% FBS) for 24 h, a linear scratch was created with a sterile pipette tip and cells were either untreated (Baseline), or treated with TGFβ1 (5 ng/ml) for 24 h, in the presence or absence of an IgG control antibody or neutralizing anti-IL-11 antibody (2 μg/ml). The wound area was imaged at 0 h (upper panels) and 24 h (lower panels), and migration was calculated using ImageJ software. All data expressed as mean±SD. Statistical significance was established with one-way ANOVA with Dunnett's multiple comparisons. Closed symbols represent IgG control treatment and open symbols indicate ant-IL11 antibody treatment. Symbols represents biological replicates. All data expressed as mean t SD. Statistical significance was determined with one-way ANOVA with Holm-Sidak multiple comparisons.
Figure 16B:
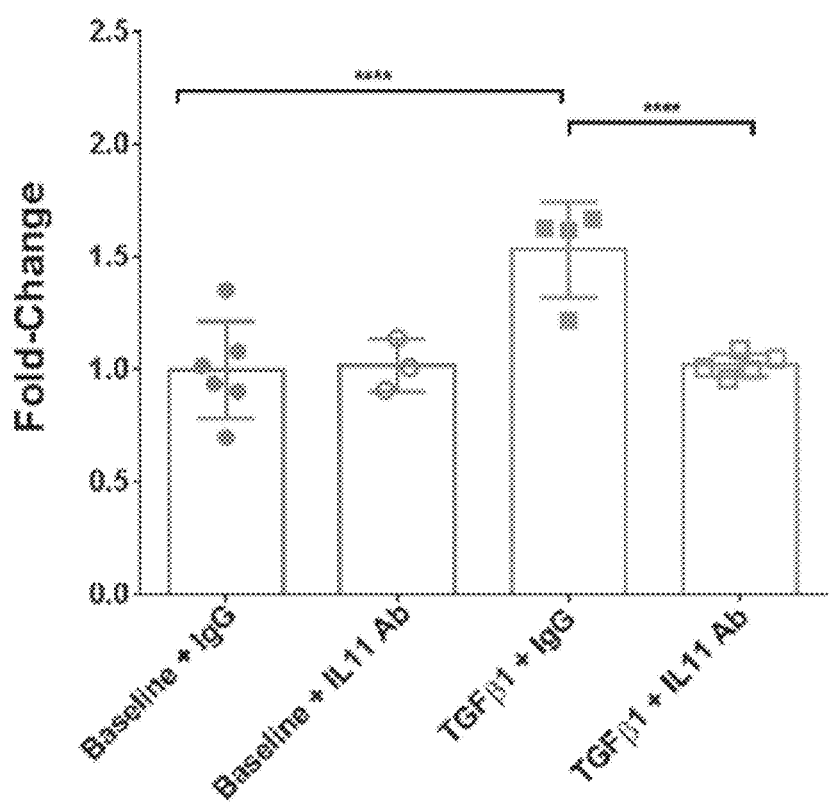

The results are shown in FIGS. 16A and 16B. Inhibition of IL-11-mediated signalling using neutralizing anti-IL-11 antibody was found to abrogate the TGFβ1-mediated increase in wound closure by VSMCs.

TGFβ1-induced cell proliferation and collagen production was reduced using IL-11 neutralizing antibodies (FIG. 13). This was also true for VSMC migration in wound closure (FIG. 14).

Example 11: Statistical Analysis

Statistical analyses of high content imaging and protein data was performed using GraphPad Prism 6 software. Fluorescence intensity (collagen I, MYOCD) was normalized to the number of cells detected in the field and recorded for 7 fields/well. Cells expressing EdU and SM22α were quantified using previously mentioned software and a percentage of EdU+ve or SM22α+ve VSMCs was determined for each field. Outliers (ROUT 2%, Prism Software) were removed before analysis. When several experimental groups were compared to one condition (i.e. to unstimulated cells), we corrected P values according to Dunnett's. When we compared several conditions within one experiment, we corrected for multiple testing according to Holm-Sidak. The criterion for statistical significance was $P<0.05$. Values of $P<0.05$, $P<0.01$, $P<0.001$, and $P<0.0001$ are denoted by *, , *, and ****, respectively.

Example 12: Conclusions

Taken together, the data suggest that IL-11 acts downstream of TGFβ1 signalling in VSMCs, and drives the pathological switch from the contractile to the secretory VSMC phenotype, and is required for the TGFβ1-mediated effects in VSMCs.

Thus inhibition of IL-11-mediated signalling is identified as a treatment option for diseases and conditions which involve transition of VSMCs from the contractile to the secretory VSMC phenotype, and/or effects of TGFβ1 signalling in VSMCs.

Example 13: IL-11 Increases Intestinal Smooth Muscle Cell Mass and Collagen Content 10-week old Col1a1-GFP reporter male mice were subjected to daily SC injection with either 100 μg/kg of recombinant mouse IL-11 (rmIL11) or an identical volume of PBS for 20 days (PBS: n=3, IL-11: n=4). At sacrifice, the colon was fixed in accordance with standard cryosectioning protocols. Frozen blocks were sectioned at 10 μm thickness. Serial sections were fixed and blocked with 5% bovine serum albumin followed by incubation overnight at 4° C. with primary rabbit anti-αSMA antibodies (1:200 dilution, Ab5694, Abcam). Following PBS washes, sections were incubated with goat anti-rabbit IgG H&L (Alexa Fluor® 647) antibodies (1:500 dilution, Ab150079, Abcam) and counterstained with DAPI nuclear staining. After mounting, images were captured on the Olympus BX51 microscope using fluorescence microscopy using ImagePro software.

Figure 17:
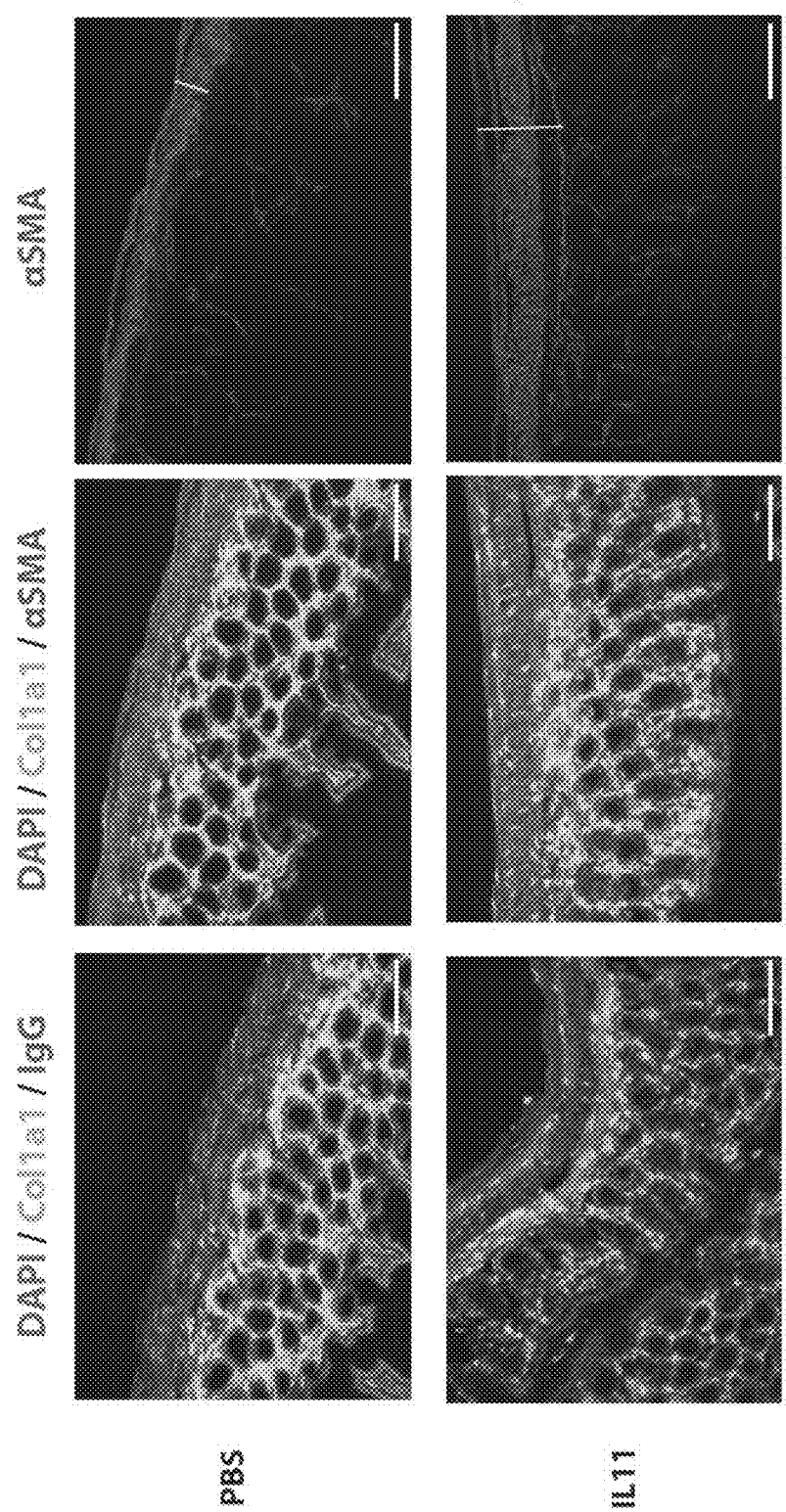
FIG. 17. Micrographs of cryosections of colon from Col1a1-GFP reporter mice treated with IL-11 or PBS. Top row: representative images from PBS-treated mice (n=3). Bottom row: representative images from mice treated with recombinant mouse IL-11 (n=4). Left: Col1a1 and nuclear staining with DAPI. Middle: Immunofluorescence for αSMA, Col1a1 and nuclear staining with DAPI. Right: Images showing expression of αSMA; bars demonstrate increased thickness of the combined smooth muscle layers in the IL-11-treated animals. Scale bar=100 μm.

The results are shown in FIG. 17. IL-11 was found to induce expansion of the muscularis mucosa, circular muscle and longitudinal muscle layers, and to cause an increase in collagen secreting smooth muscle cells in these layers in mouse colon.

IL-11 mediated signaling is thus demonstrated to increase secretory SMC number and activity in a variety of different tissues.

Example 14: IL-11 Overexpression Contributes to SMC Pathology in the Heart/Aorta The effect of increased IL-11 expression on fibrosis of the heart was investigated using mice that conditionally express IL-11 in smooth muscle cells upon induction with tamoxifen.

Smooth muscle cell specific Cre male mice (B6. FVB-Tg(Myh11-cre/ERT2)1Soff/J) were purchased from Jackson Laboratory (01979; Bar Harbor, Me.) and crossed with female mice carrying the ROSA-IL11 gene (C57BL/6N-Gt (ROSA)26Sor$^{tm1(CAG-il11)Cook}$/J) available from Jackson Laboratory (031928) to generate mice with conditional expression of mouse IL-11 solely in smooth muscle cells (SMRS). Tamoxifen induction procedure was initiated at 6 weeks of age and comprised of 3 doses of 1 mg/kg across a week injected intraperitoneally followed by a week of wash-out. Smooth muscle-specific Cre only littermates (SMWT) were designated as mouse strain controls and corn oil was administered as vehicle controls for tamoxifen.

Figure 18A:
FIGS. 18A to 18E. The effect of increased IL-11 expression on SMC pathology in the heart. Tamoxifen-induced Cre-mediated IL-11 overexpression in SMCs (SMRS) mice show elevated IL-11 protein expression in the heart (FIG. 18A) and increased heart weight to body weight (HW/BW) ratios (FIG. 18B) compared to SMWT controls. Heart tissue sections from SMRS mice stained with Masson's trichrome show perivascular fibrosis compared to SMWT controls (FIG. 18C). Ventricles of SMRS mice show elevated collagen expression compared to SMWT controls (FIG. 18D; , * denotes P<0.01 and P<0.0001 respectively). IL-11 overexpression causes elevated expression of ECM components and inflammatory genes in heart SMCs (FIG. 18E): left bars represent SMWT controls, right bars represent SMRS mice overexpressing IL-11. *, , * denotes P<0.05, P<0.01, and P<0.001 respectively.
Figure 18B:
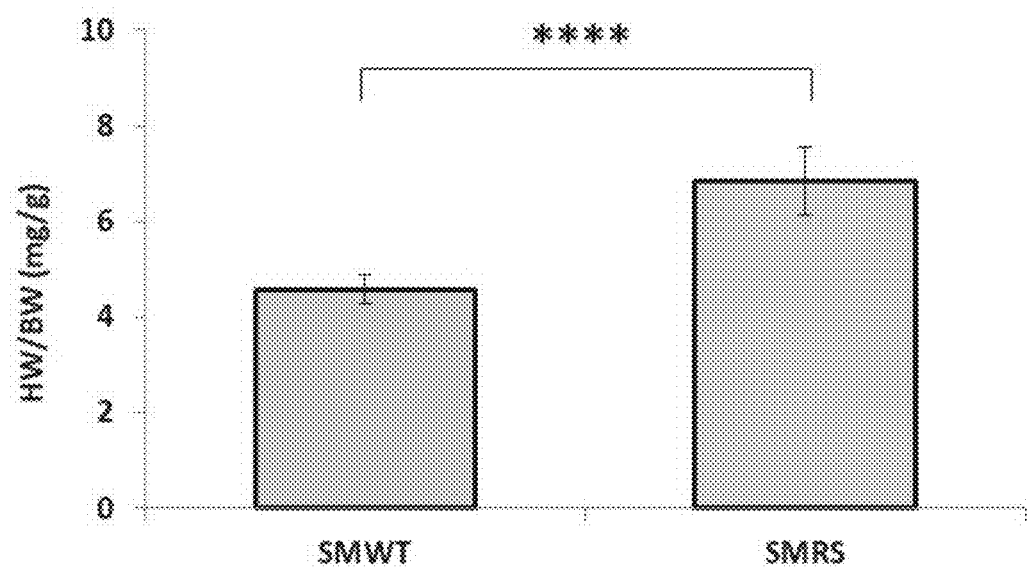

FIG. 18A shows elevated IL-11 protein expression in the hearts of 8-week old SMRS mice compared to SMWT controls following two weeks of tamoxifen induction (n=6-7 per group), detected by immunoblotting. FIG. 18B shows that heart weight to body weight (HW/BW) ratios in 8-week-old SMRS mice were elevated compared to SMWT controls (n=8 per group).

Heart sections from SMRS and SMWT mice were assessed for collagen by staining with Masson's trichrome stain. Increased expression/secretion of extracellular matrix (ECM) components such as collagen indicate a secretory SMC phenotype. Heart tissue was fixed in 10% neutral-buffered formalin for 24-48 hours, dehydrated and embedded in formalin. Sections (5 μm) were stained with Masson's trichrome staining. In addition, the amount of collagen in ventricular tissues was quantified by colorimetric detection of hydroxyproline using a Quickzyme Total Collagen assay kit (Quickzyme Biosciences).

Figure 18C:
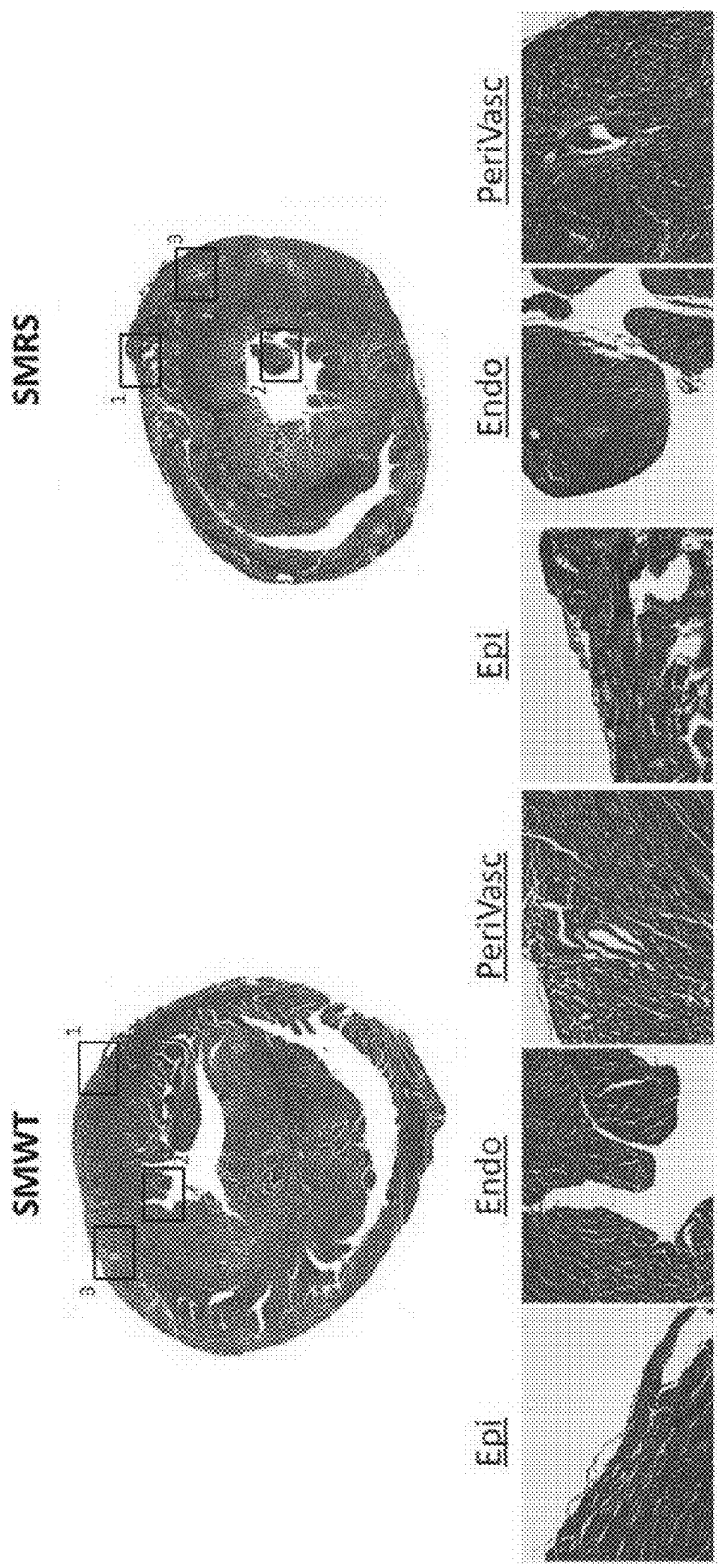
Figure 18D:
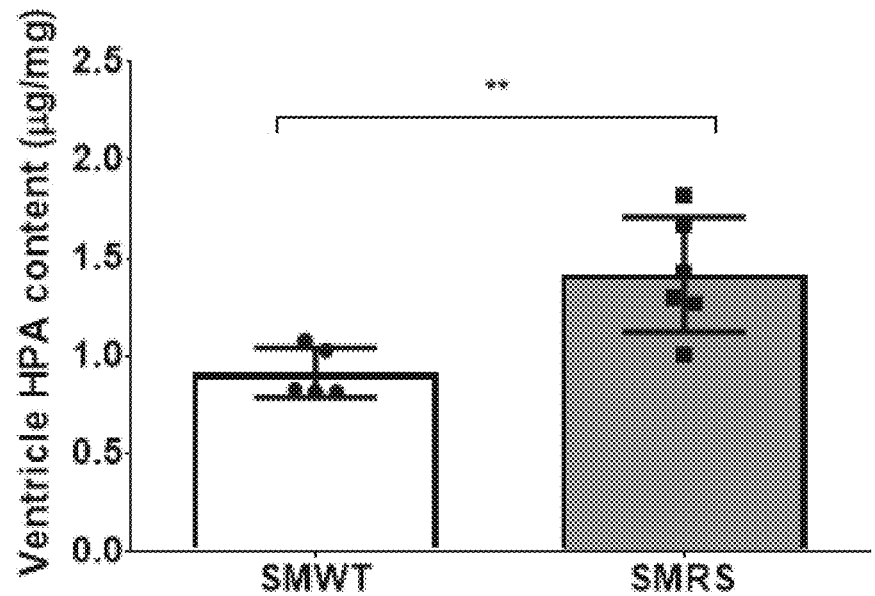

FIG. 18C shows representative heart sections stained with Masson's trichrome (n=3 per group). Heart tissue from SMRS mice demonstrates perivascular fibrosis compared to SMWT controls. FIG. 18D shows that ventricles of SMRS mice demonstrate elevated collagen expression compared to SMWT controls based on hydroxyproline assessment (HPA; n=5-6 per group). Statistical analyses were performed using two-tailed unpaired T-test. , ** denotes P<0.01 and P<0.0001 respectively.

Thus, overexpression of IL-11 in smooth muscle cells contributes to perivascular fibrosis in the heart.

Expression of ECM and Inflammatory Genes

Gene expression of a number of ECM components and inflammatory genes in heart tissue was quantified by RT-PCR. Heart tissue samples were obtained from tamoxifen-induced Cre-mediated SMC IL-11 overexpression mice.

Total RNA was extracted from snap-frozen tissues using Trizol reagent (Invitrogen) followed by Purelink RNA mini kit (Invitrogen) purification. The cDNA was prepared using an iScript cDNA synthesis kit, in which each reaction contained 1 μg of total RNA, as per manufacturer's instructions. Quantitative RT-PCR gene expression analysis was performed on duplicate samples with fast SYBR green (Qiagen) technology using QuantStudio (Applied Biossystem). Expression data were normalized to GAPDH mRNA expression levels and we used the $2^{-\Delta\Delta Ct}$ method to calculate fold change. Specific primer probes were obtained from Integrated DNA Technologies and are shown in Table 1.

| Genes | Forward primer (5' to 3') | Reverse primer (5' to 3') |
|---|---|---|
| IL-11 | AATTCCCAGCTGACGGAGATCACA | TCTACTCGAAGCCTTGTCAGCACA |
| IL-11ra | CAGCACGTCCTGAAGTCTCC | GGAAGTAAGGTAGCGGGTGG |
| TGFβ1 | CCCTATATTTGGAGCCTGGA | CTTGCGACCCACGTAGTAGA |
| Col1a1 | GGGGCAAGACAGTCATCGAA | GTCCGAATTCCTGGTCTGGG |
| Col1a2 | CCCAGAGTGGAACAGCGATT | ATGAGTTCTTCGCTGGGGTG |
| Col3a1 | ATGCCCACAGCCTTCTACAC | ACCAGTTGGACATGATTCACAG |
| FN1 | CACCCGTGAAGAATGAAGA | GGCAGGAGATTTGTTAGGA |
| MMP2 | ACAAGTGGTCCGCGTAAAGT | AAACAAGGCTTCATGGGGGC |
| TIMP-1 | GGGCTAAATTCATGGGTTCC | CTGGGACTTGTGGGCATATC |
| IL6 | AGGATACCACTCCCAACAGACC | AGTGCATCATCGTTGTTCATACA |
| TNFα | CTCTTCTCAAAATTCGAGTGACAA | TGGGAGTAGACAAGGTACAACCC |
| CCL2 | GAAGGAATGGGTCCAGACAT | ACGGGTCAACTTCACATTCA |
| CCL5 | GCTGCTTTGCCTACCTCTCC | TCGAGTGACAAACACGACTGC |

Figure 18E:
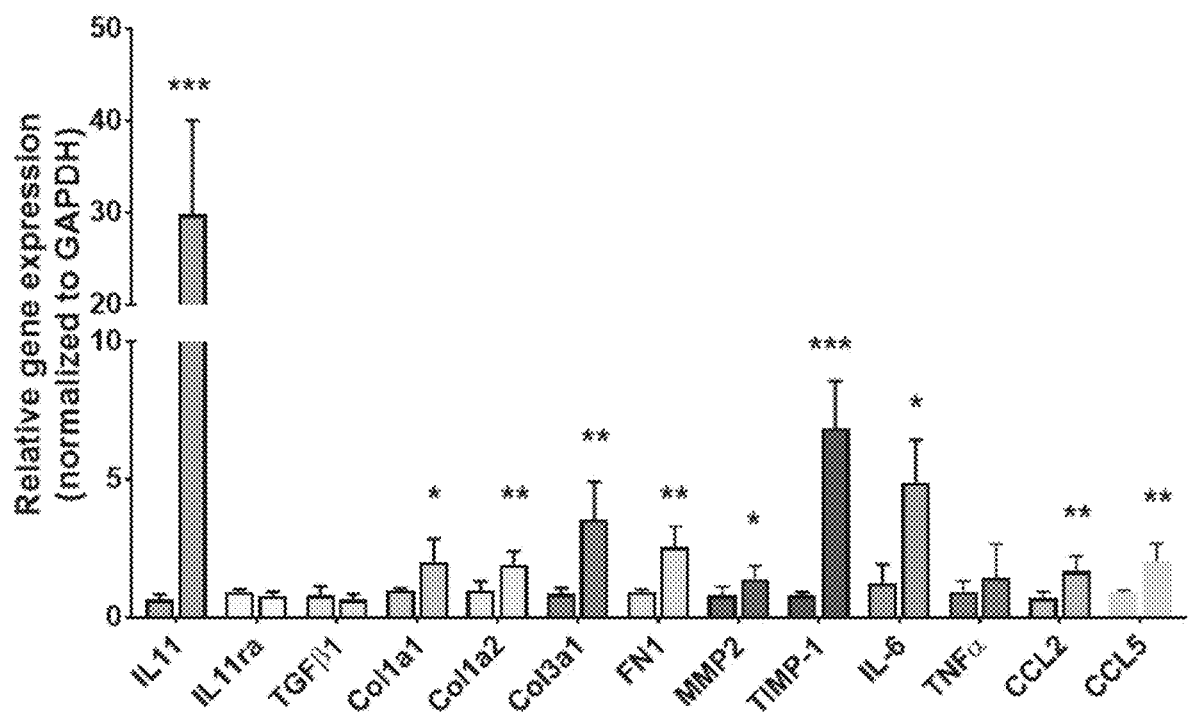

The results are shown in FIG. 18E. IL-11 overexpression causes elevated expression of ECM components and inflammatory genes in heart SMCs. Columns indicate average gene expression (normalized to GAPDH expression) with left bars denoting SMWT control and right bars denoting SMRS overexpression groups (n=5 per group). Extracellular matrix genes includes collagens (Col1a1, Col1a2, Col3a1), fibronectin (FN1), matrix metalloproteinase (MMP2), and tissue inhibitor of matrix metalloproteinase (TIMP-1). Inflammatory genes included interleukin-6 (IL-6), tumour necrosis factor alpha (TNFα), C—C motif chemokine ligand-2 and -5 (CCL2 and CCL5 respectively). Statistical analysis was performed using a two-tailed unpaired T-test. *, , * denotes P<0.05, P<0.01, and P<0.001 respectively.

Heart Size and Function

Tamoxifen-induced Cre-mediated IL-11 overexpressing mice were employed to analyse the effect of IL-11 overexpression on heart size and function.

IL-11 expression was induced as before. Trans-thoracic echocardiography was performed on all mice using Vevo 2100 with a MS400 linear array transducer (VisualSonics), 18-38 MHz by a single, trained echocardiographer blinded to genotype and treatment group. Mice were anaesthetised with 2% isofluorane and maintained at 0.6-1.0% isoflurane, while the body temperature was maintained at 37° C. on a heated platform. Chest and neck hair were removed using depilatory cream and a layer of acoustic coupling gel was applied to the thorax. An average of 10 cardiac cycles of standard 2D and rn-mode short axis at mid papillary muscle level were obtained and stored for offline analysis for LV dimensions and wall thickness according to previously described methods (Gao S, et al. *Curr. Protoc Mouse Biol* 2011, 1, 71-83). LV ejection fraction was calculated using a modified Quinone method (Tortoledo F A, et al. *Circulation* 1983, 67, 579-584). Left atrium (LA) diameter was measured in parasternal long axis view and averaged across 3 measurements. LV mass was estimated according to previous literature (Fard C Y, et al. *J Am Soc Echocardiogr* 2000; 13: 582-7).

Figure 19A:
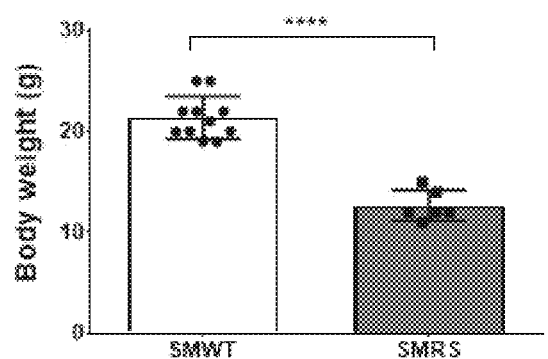
FIGS. 19A to 19D. Graphs showing the effect of increased IL-11 expression on heart size and function. SMRS mice have a lower body weight (FIG. 19A) and left ventricular (LV) mass (FIG. 19B) compared to SMWT controls, but show increased LV mass ratio when corrected for body weights (FIG. 19C). Left atrium (LA) diameter is increased in SMRS mice compared to controls (FIG. 19D). *, , *, **** denote P<0.05, P<0.01, p<0.001 and P<0.0001 respectively.
Figure 19B:
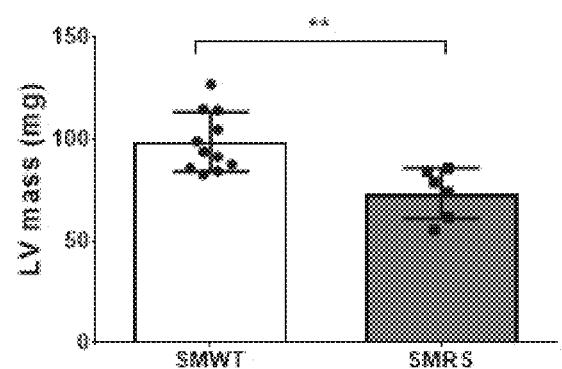
Figure 19C:
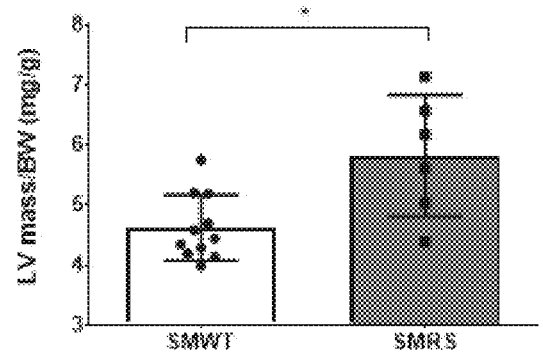
Figure 19D:
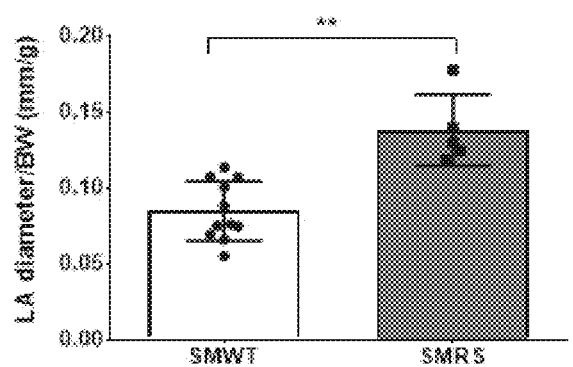

The results are shown in FIGS. 19A to 21D. FIG. 19A shows that SMRS mice have a lower body weight compared to SMWT controls, measured prior to echocardiography. Estimated LV mass based on echocardiography demonstrates lower heart weights in SMRS mice compared to SMWT controls but increased LV mass ratio when corrected for body weights (FIGS. 19B and 19C). FIG. 19D represents left atrium (LA) diameter measured in parasternal long axis view and shows increased LA size in SMRS mice compared to SMWT controls.

Figure 20A:
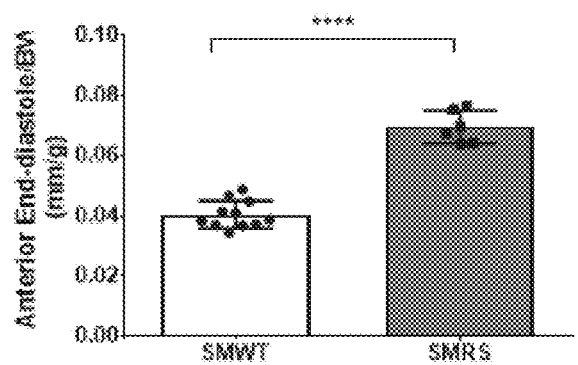
FIGS. 20A to 20C. Graphs showing that anterior wall thickness (FIG. 20A), LV internal diameter (FIG. 20B) and posterior LV wall thickness (FIG. 20C) at end-diastole are increased in SMRS mice compared to SMWT controls. *, , *, **** denote P<0.05, P<0.01, p<0.001 and P<0.0001 respectively.
Figure 20B:
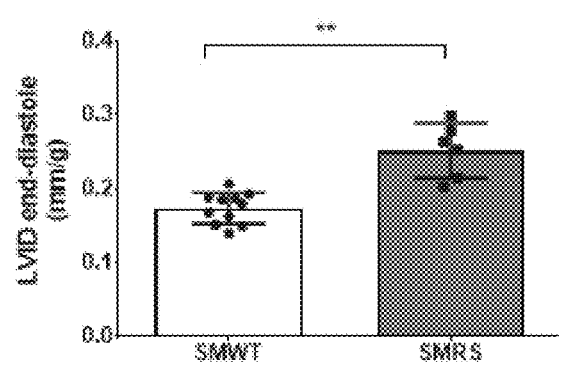
Figure 20C:
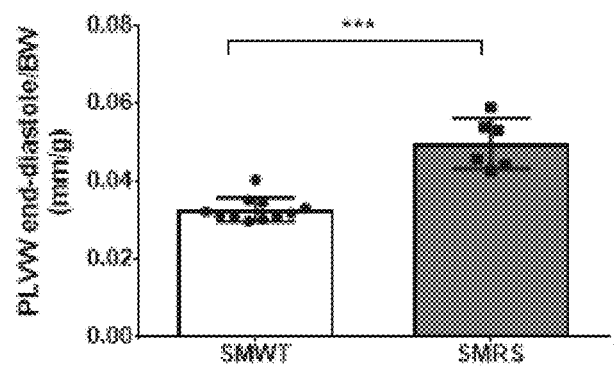

FIGS. 20A to 20C show anterior wall thickness, LV internal diameter, and posterior LV wall thickness, respectively, at end-diastole with correction for body weight. All three measurements were increased in SMRS mice compared to SMWT controls.

Figure 21A:
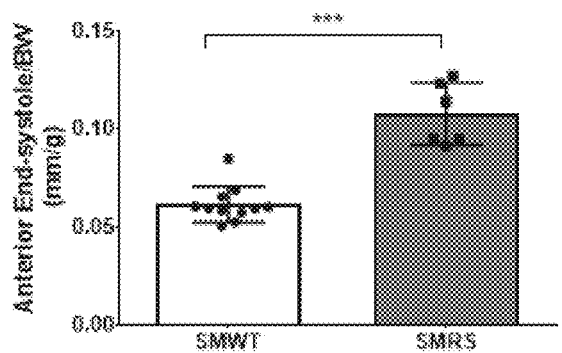
FIGS. 21A to 21D. Graphs showing that anterior wall thickness (FIG. 21A), LV internal diameter (FIG. 21B) and posterior LV wall thickness (FIG. 21C) at end-systole are increased in SMRS mice compared to SMWT controls. The ejection fraction is conserved in SMRS mice (FIG. 21D). *, , *, **** denote P<0.05, P<0.01, p<0.001 and P<0.0001 respectively.
Figure 21B:
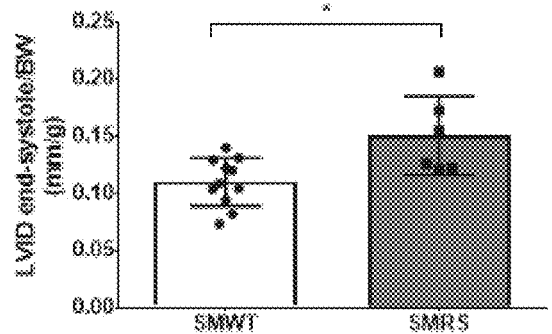
Figure 21C:
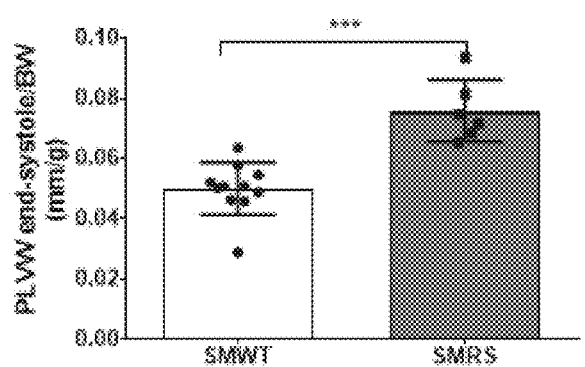

FIGS. 21A to 21C show anterior wall thickness, LV internal diameter, and posterior LV wall thickness, respectively, at end-systole with correction for body weight. All three measurements were increased in SMRS mice compared to SMWT controls.

Figure 21D:
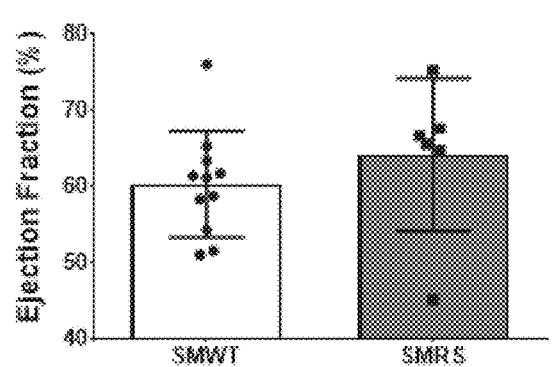

FIG. 21D shows that the ejection fraction was preserved in SMRS mice as compared to SMWT controls.

In FIGS. 19A-21D, each dot represents an individual mouse. Statistical analyses were performed using two-tailed unpaired T-test. *, , *, **** denote P<0.05, P<0.01, p<0.001 and P<0.0001 respectively.

Thus, tamoxifen-induced Cre-mediated IL-11 overexpression in smooth muscle cells results in left ventricular (LV) hypertrophy and chamber stiffness with preserved systolic function as indicated by echocardiography.

Aortic Remodelling

Tamoxifen-induced Cre-mediated IL-11 mice were employed to analyse the effect of IL-11 overexpression on aortic SMCs.

8-week-old SMRS mice, as before, were subjected to two weeks of tamoxifen induction (n=6-7 per group).

Trans-thoracic echocardiography was performed on all mice using Vevo 2100 with a MS400 linear array transducer (VisualSonics), 18-38 MHz by a single, trained echocardiographer blinded to genotype and treatment group. Mice were anaesthetised with 2% isofluorane and maintained at 0.6-1.0% isoflurane, while the body temperature was maintained at 37° C. on a heated platform. Chest and neck hair were removed using depilatory cream and a layer of acoustic coupling gel was applied to the thorax. Aortic root and ascending aortic sizes were assessed from B and m-mode of parasternal long-axis view, using inner edge-to-inner edge in accordance with the widely accepted American and European guidelines (Lang R M, et al. Recommendations for chamber quantification. *Eur J Echocardiogr* 7, 79-108 (2006)). Peak aortic flow velocity was obtained by applying pulse wave Doppler across the aortic valve from the aortic arch at suprasternal view. All measurements were averaged over three cardiac cycles.

The results are shown in FIGS. 22A-E. Each dot represents an individual mouse. Statistical analyses were performed using two-tailed unpaired T-test. , ** denote P<0.05 and P<0.0001 respectively.

Figure 22A:
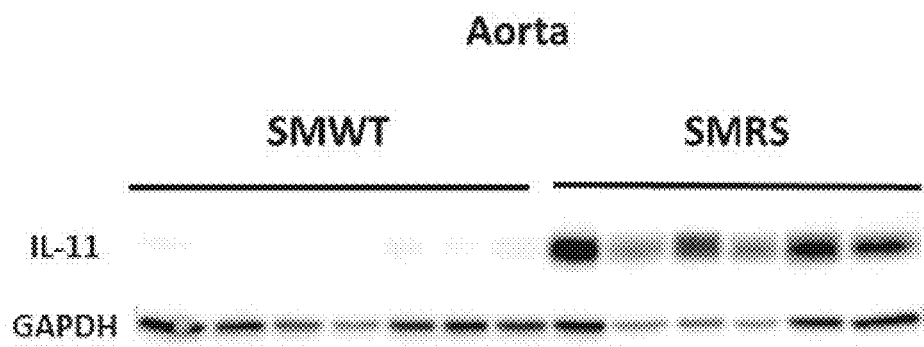
FIGS. 22A to 22E. IL-11 expression in aortic SMC remodelling. IL-11 protein expression is increased in the proximal thoracic aorta of SMRS mice compared to SMWT controls (FIG. 22A). Aortic root internal diameter as measured at end-diastole (FIG. 22B) and end-systole (FIG. 22C) with correction for body weight is greater in SMRS mice compared to SMWT controls. Ascending aorta internal diameter at end-systole with correction for body weight is greater in SMRS mice compared to SMWT controls (FIG. 22D). SMRS mice have preserved aortic peak flow velocity as compared to controls (FIG. 22E). , ** denote P<0.05 and P<0.0001 respectively.
Figure 22B:
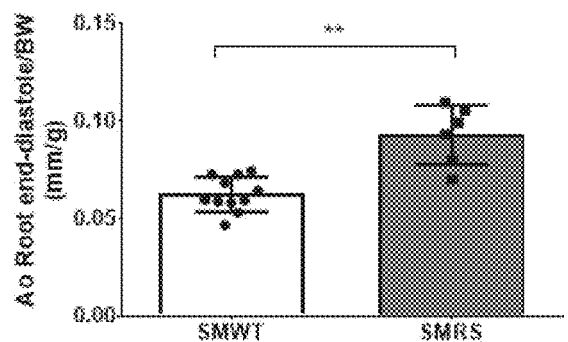
Figure 22C:
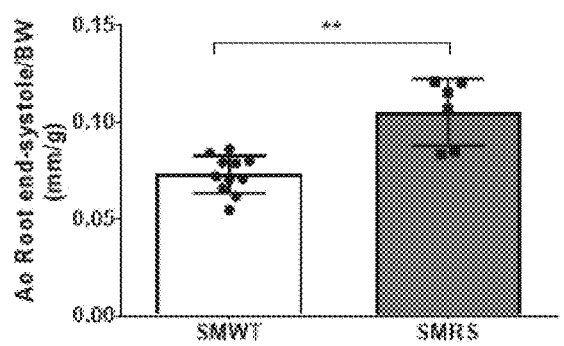
Figure 22D:
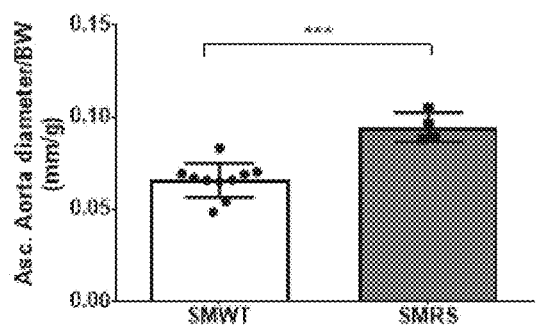
Figure 22E:
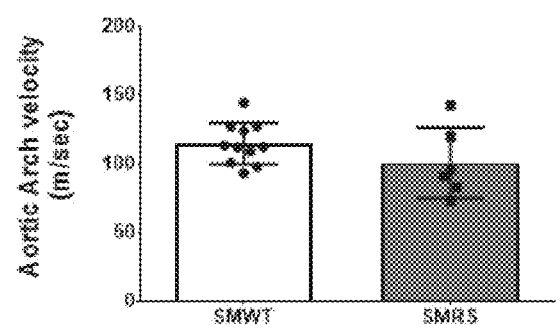

FIG. 22A demonstrates elevated IL-11 protein expression in the proximal thoracic aorta of 8-week-old SMRS mice compared to SMWT controls (detected by immunoblotting). FIGS. 22B and 22C show that aortic root internal diameter as measured at end-diastole and end-systole respectively with correction for body weight is greater in SMRS mice compared to SMWT controls. FIG. 22D shows that ascending aorta internal diameter at end-systole with correction for body weight is greater in SMRS mice compared to SMWT controls. FIG. 22E shows that SMRS mice have preserved aortic peak flow velocity compared to controls.

Thus, tamoxifen-induced Cre-mediated IL-11 overexpression in smooth muscle cells results in aortic remodelling with preserved flow velocity.

Example 15: IL-11 Overexpression Contributes to SMC Pathology in the Lung

The effect of increased IL-11 expression on fibrosis of the lung was investigated using the tamoxifen-induced Cre-mediated SMC IL-11 overexpression mouse model.

8-week old SMRS mice were subjected to two weeks of tamoxifen induction as before (n=3 per group). Collagen expression was measure by hydroxyproline assessment as described in Example 14 (n=6 per group). Representative lung sections were stained with Masson's trichrome stain, as described in Example 14 (n=3 per group).

Figure 23A:
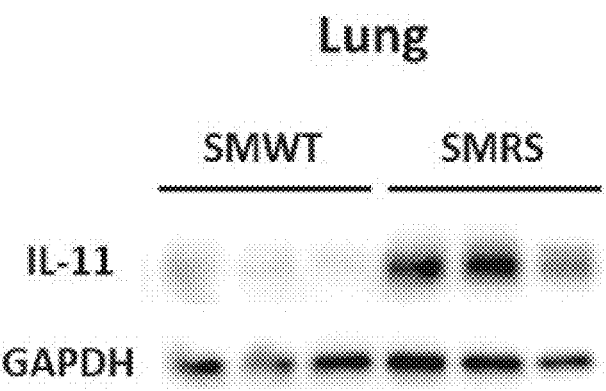
FIGS. 23A to 23D. The effect of increased IL-11 expression on SMC pathology in the lung. SMRS mice show elevated IL-11 protein expression in the lungs (FIG. 23A), increased lung to body weight ratios (FIG. 23B) and elevated collagen expression in the lungs when corrected for lung-to-body-weight (LW/BW) ratio (FIG. 23C) compared to SMWT controls.
Figure 23B:
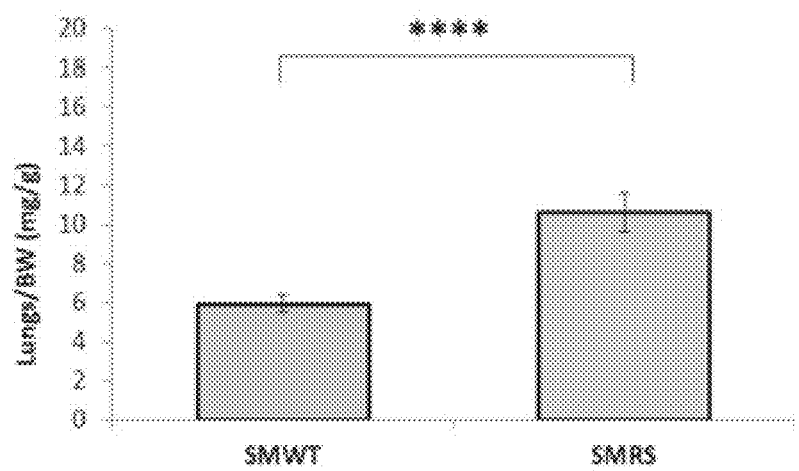
Figure 23C:
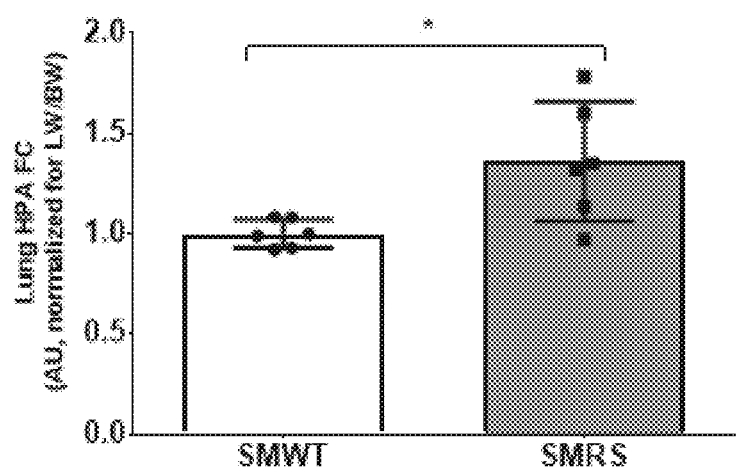
Figure 23D:
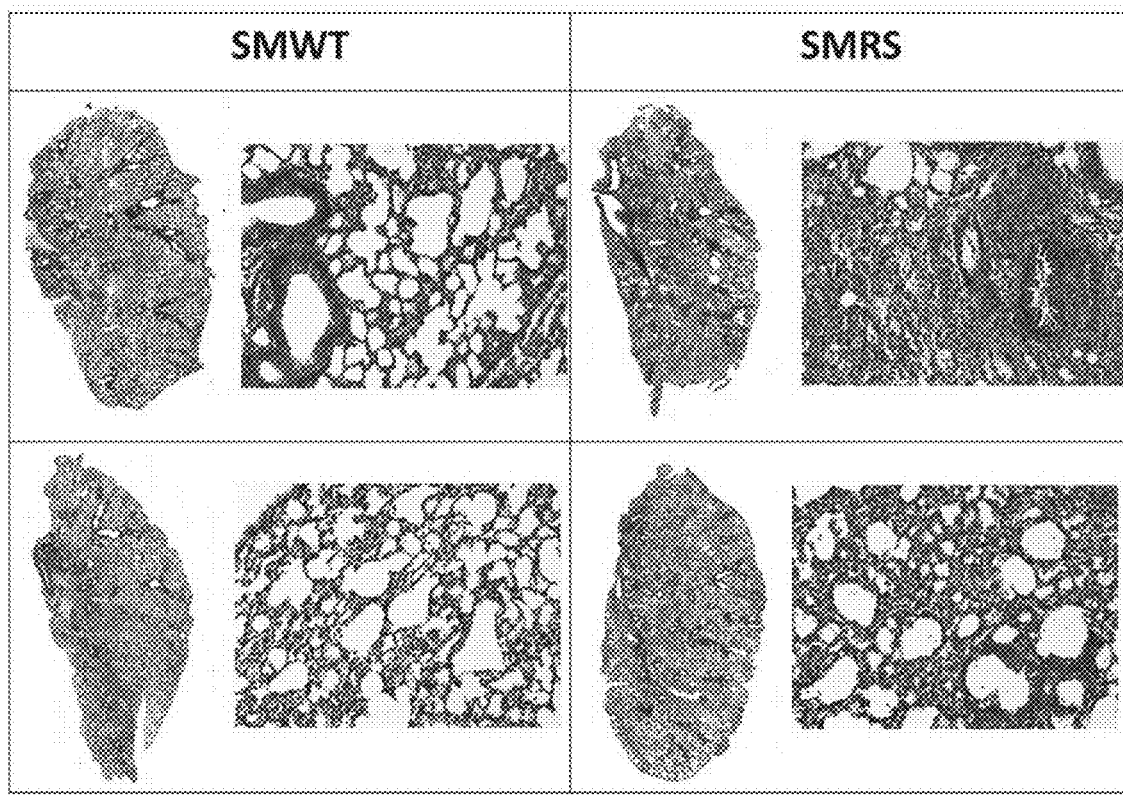

The results are shown in FIGS. 23A-D. FIG. 23A demonstrates elevated IL-11 protein expression in the lungs of 8-week-old SMRS mice compared to SMWT controls (detected by immunoblotting). FIG. 23B shows that SMRS mice demonstrate increased lung to body weight ratios as compared to SMWT controls (n=8 per group). FIG. 23C shows that lungs of SMRS mice demonstrate elevated collagen expression when corrected for lung-to-body weight ratio as compared to controls based on hydroxyproline assessment. FIG. 23D provides representative lung sections stained with Masson's trichrome and demonstrates increased lung fibrosis and infiltrating cell infiltrates in SMRS lungs as compared to SMWT controls.

Thus, tamoxifen-induced Cre-mediated IL-11 overexpression in smooth muscle cells results in increased lung fibrosis.

Expression of ECM and Inflammatory Genes

RT-PCR was performed as described in Example 14.

Figure 24:
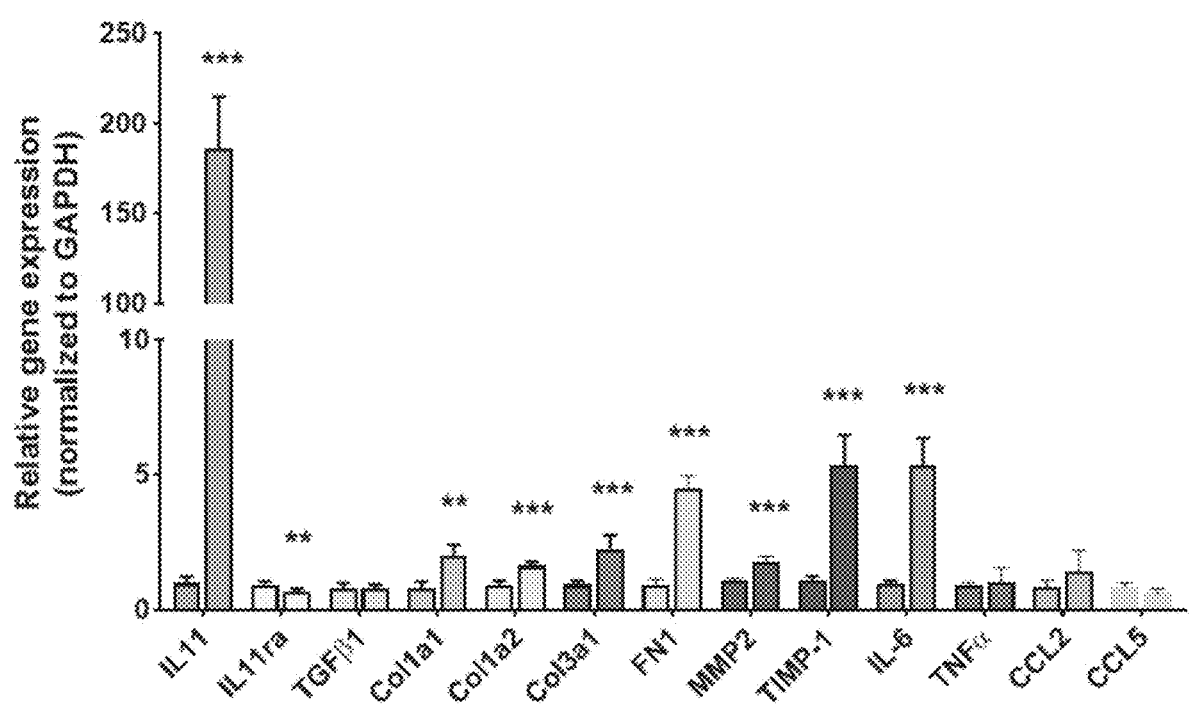
FIG. 24. Graph showing that SMRS mice have elevated expression of extracellular matrix and inflammatory genes in the lungs. Left bars represent SMWT controls, right bars represent SMRS mice overexpressing IL-11. , * denote P<0.01, and P<0.001 respectively.

FIG. 24 shows that tamoxifen-induced Cre-mediated IL-11 overexpression in smooth muscle cells causes elevated expression of extracellular matrix and inflammatory genes in the lungs. Columns indicate average gene expression (normalized to GAPDH expression) with left bars denoting SMWT and right bars denote for SMRS groups (n=5 per group). Extracellular matrix genes includes collagens (Col1a1, Col1a2, Col3a1), fibronectin (FN1), matrix metalloproteinase (MMP2), and tissue inhibitor of matrix metalloproteinase (TIMP-1). Inflammatory genes included interleukin-6 (IL-6), tumour necrosis factor alpha (TNFα), C—C motif chemokine ligand-2 and -5 (CCL2 and CCL5 respectively). Statistical analyses were performed using two-tailed unpaired T-test. , * denote P<0.01, and P<0.001 respectively.

Example 16: IL-11 Overexpression Contributes to SMC Pathology in the Liver

The effect of increased IL-11 expression on fibrosis of the liver was investigated using the tamoxifen-induced Cre-mediated SMC IL-11 overexpression mouse model.

Tamoxifen induction and hydroxyproline assessment were performed as described in Example 14.

Figure 25A:
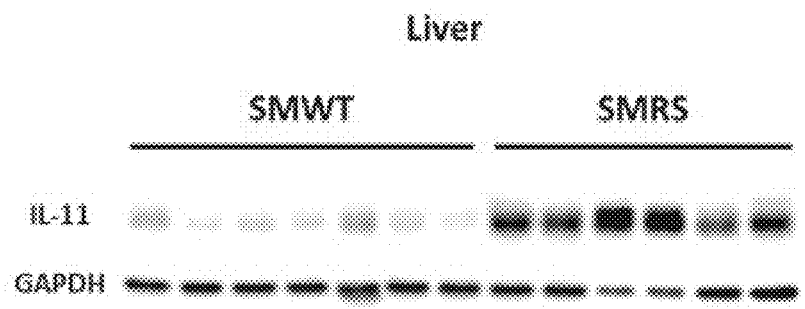
FIGS. 25A to 25C. The effect of increased IL-11 expression on SMC pathology in the liver. SMRS mice show elevated IL-11 protein expression in the liver (FIG. 25A), unchanged liver to body weight ratios (FIG. 25B) and elevated collagen expression in livers (FIG. 25C) compared to SMWT controls. * denotes P<0.05.
Figure 25B:
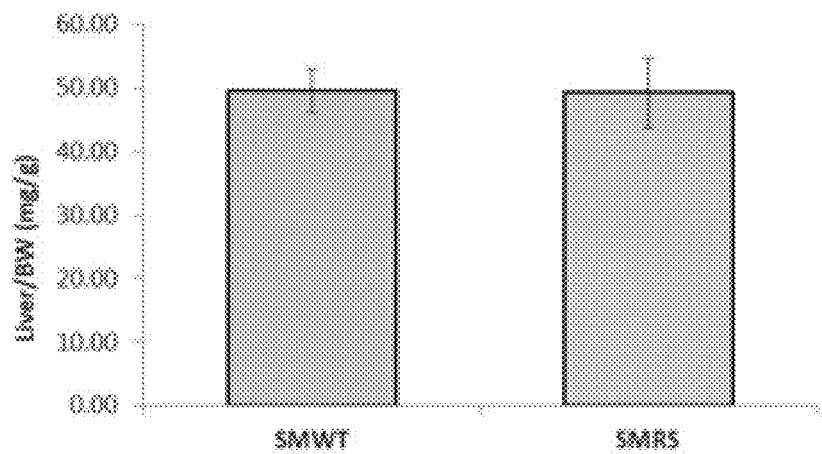
Figure 25C:
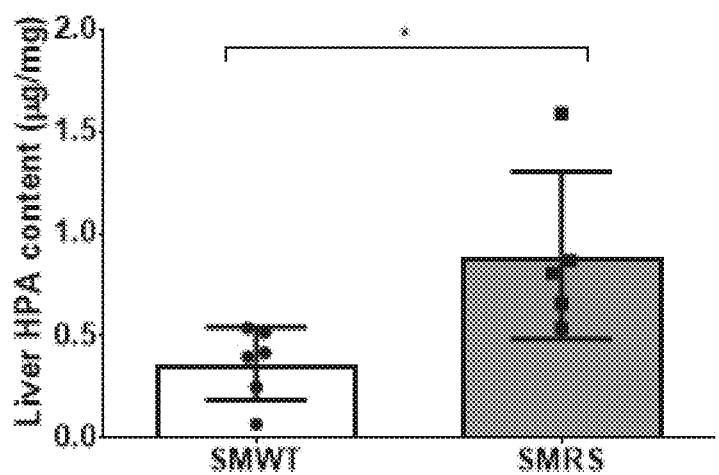

The results are shown in FIGS. 25A to 25C. FIG. 25A demonstrates elevated IL-11 protein expression in the liver of 8-week-old SMRS mice compared to SMWT controls following two weeks of tamoxifen induction (n=6-7 per group; detected by immunoblotting). FIG. 25B shows that SMRS mice demonstrate unchanged liver-to-body weight ratios as compared to controls (n=8 per group). FIG. 25C shows that livers of SMRS mice demonstrated elevated collagen expression as compared to controls based on hydroxyproline assessment (n=5-6 per group). Statistical analyses were performed using two-tailed unpaired T-test. * denotes P<0.05.

Thus, tamoxifen-induced Cre-mediated IL-11 overexpression in smooth muscle cells results in increased liver fibrosis.

Expression of ECM and Inflammatory Genes

RT-PCR was performed as described in Example 14.

Figure 26:
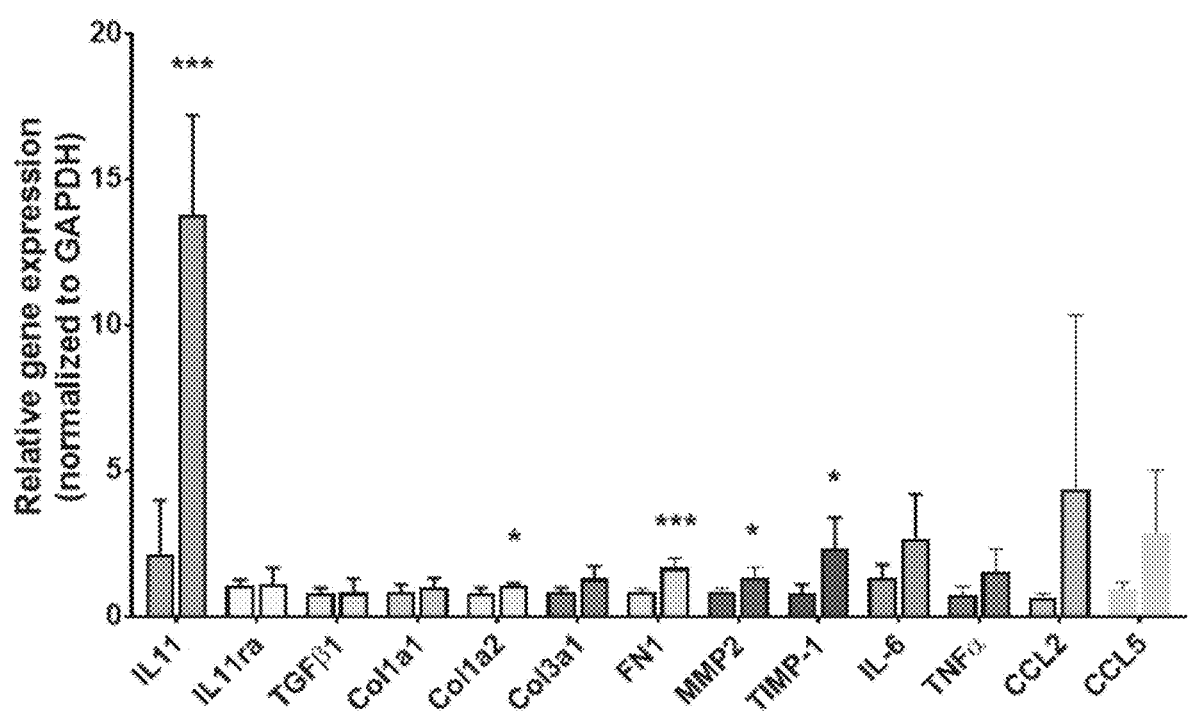
FIG. 26. Graph showing that SMRS mice have elevated expression of extracellular matrix and inflammatory genes in the liver. Left bars represent SMWT controls, right bars represent SMRS mice overexpressing IL-11 in SMCs. *, *** denote P<0.05, and P<0.001 respectively.

FIG. 26 shows that tamoxifen-induced Cre-mediated IL-11 overexpression in smooth muscle cells causes elevated extracellular matrix protein expression in the liver. Columns indicate average gene expression (normalized to GAPDH expression) with left bars denoting SMWT and right bars denote for SMRS groups (n=5 per group). Extracellular matrix genes includes collagens (Col1a1, Col1a2, Col3a1), fibronectin (FN1), matrix metalloproteinase (MMP2), and tissue inhibitor of matrix metalloproteinase (TIMP-1).

Inflammatory genes included interleukin-6 (IL-6), tumour necrosis factor alpha (TNFα). C—C motif chemokine ligand-2 and -5 (CCL2 and CCL5 respectively). Statistical analyses were performed using two-tailed unpaired T-test. *, *** denote P<0.05, and P<0.001 respectively.

Example 17: IL-11 Overexpression Contributes to SMC Pathology in the Kidney

The effect of increased IL-11 expression on fibrosis of the kidney was investigated using the tamoxifen-induced Cre-mediated SMC IL-11 overexpression mouse model.

Tamoxifen induction and hydroxyproline assessment were performed as described in Example 14.

Figure 27A:
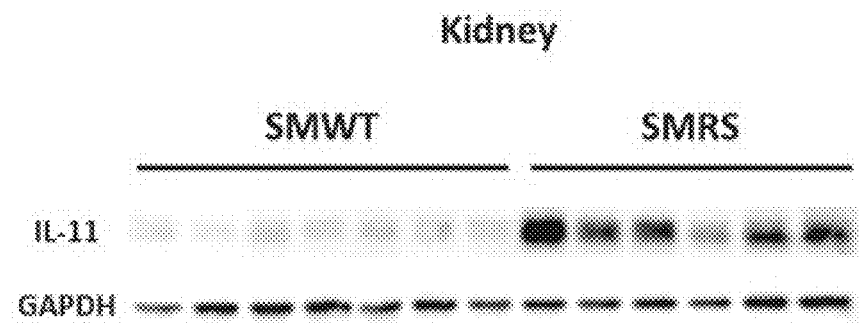
FIGS. 27A to 27C. The effect of increased IL-11 expression on SMC pathology in the kidney. SMRS mice show elevated IL-11 protein expression in the kidney (FIG. 27A), increased kidney-to-body weight ratios (FIG. 27B) and demonstrate a trend towards elevated collagen expression in kidneys (FIG. 27C) compared to controls. * denotes P<0.05.
Figure 27B:
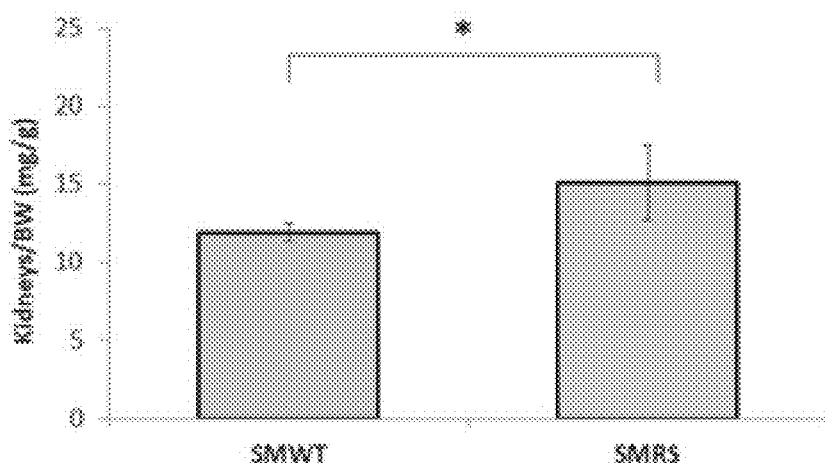
Figure 27C:
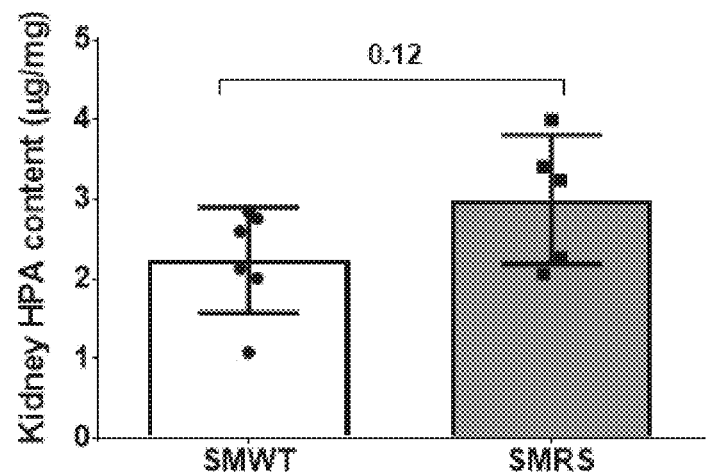

The results are shown in FIGS. 27A to 27C. FIG. 27A demonstrates elevated IL-11 protein expression in the kidney of 8-week-old SMRS mice compared to SMWT controls following two weeks of tamoxifen induction (n=6-7 per group; detected by immunoblotting). FIG. 27B shows that SMRS mice demonstrate increased kidney-to-body weight ratios as compared to SMWT controls (n=8 per group). FIG. 27C shows that kidneys of SMRS mice demonstrate a trend towards elevated collagen expression compared to controls based on hydroxyproline assessment (P=0.12, n=5 per group). Statistical analyses were performed using two-tailed unpaired T-test. * denotes P<0.05.

Thus, tamoxifen-induced Cre-mediated IL-11 overexpression in smooth muscle cells results in increased kidney fibrosis.

Expression of ECM and Inflammatory Genes

RT-PCR was performed as described in Example 14.

Figure 28:
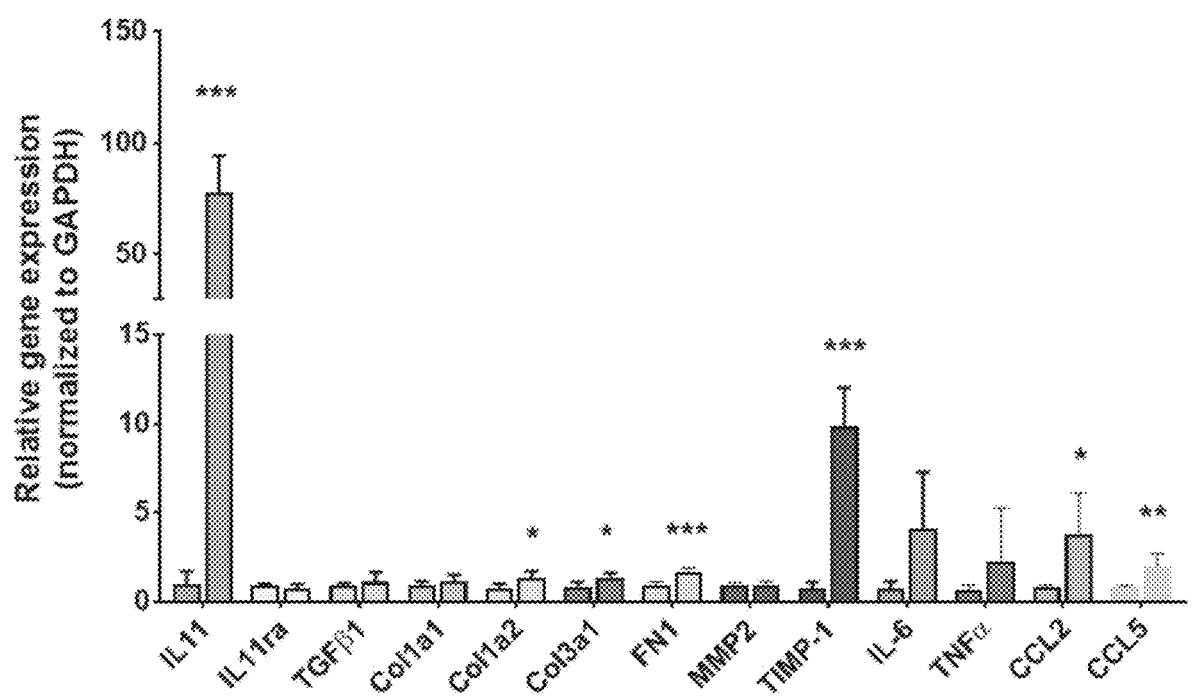
FIG. 28. Graph showing that SMRS mice have elevated expression of extracellular matrix and inflammatory genes in the kidney. Left bars represent SMWT controls, right bars represent SMRS mice overexpressing IL-11 in SMCs. *, , * denote P<0.05, P<0.01 and P<0.001 respectively.

FIG. 28 shows that tamoxifen-induced Cre-mediated IL-11 overexpression in smooth muscle cells demonstrate elevated extracellular matrix protein expression in the kidney. Columns indicate average gene expression (normalized to GAPDH expression) with left bars denoting SMWT and right bars denote for SMRS groups (n=5 per group). Extracellular matrix genes includes collagens (Col1a1, Col1a2, Col3a1), fibronectin (FN1), matrix metalloproteinase (MMP2), and tissue inhibitor of matrix metalloproteinase (TIMP-1). Inflammatory genes included interleukin-6 (IL-6), tumour necrosis factor alpha (TNFα), C—C motif chemokine ligand-2 and -5 (CCL2 and CCL5 respectively). Statistical analyses were performed using two-tailed unpaired T-test. *, , * denote P<0.05, P<0.01 and P<0.001 respectively.

Example 18: IL-11 Overexpression Contributes to SMC Pathology in Inflammatory Bowel Disorders The effect of increased IL-11 expression on inflammatory bowel disorders was investigated using the tamoxifen-induced Cre-mediated SMC IL-11 overexpression mouse model.

Tamoxifen induction was performed as described in Example 14. The levels of fecal calprotectin (S100A8/A9) were quantified using Mouse S100A8/S100A9 Heterodimer Duoset ELISA (DY8596-05) according to manufacturer's instructions. Fecal calprotectin was extracted using fecal extraction buffer (0.1 M Tris, 0.15 M NaCl, 1.0 M urea, 10 mM $CaCl_2$), 0.1 M citric acid monohydrate, 5 g/l BSA).

Figure 29A:
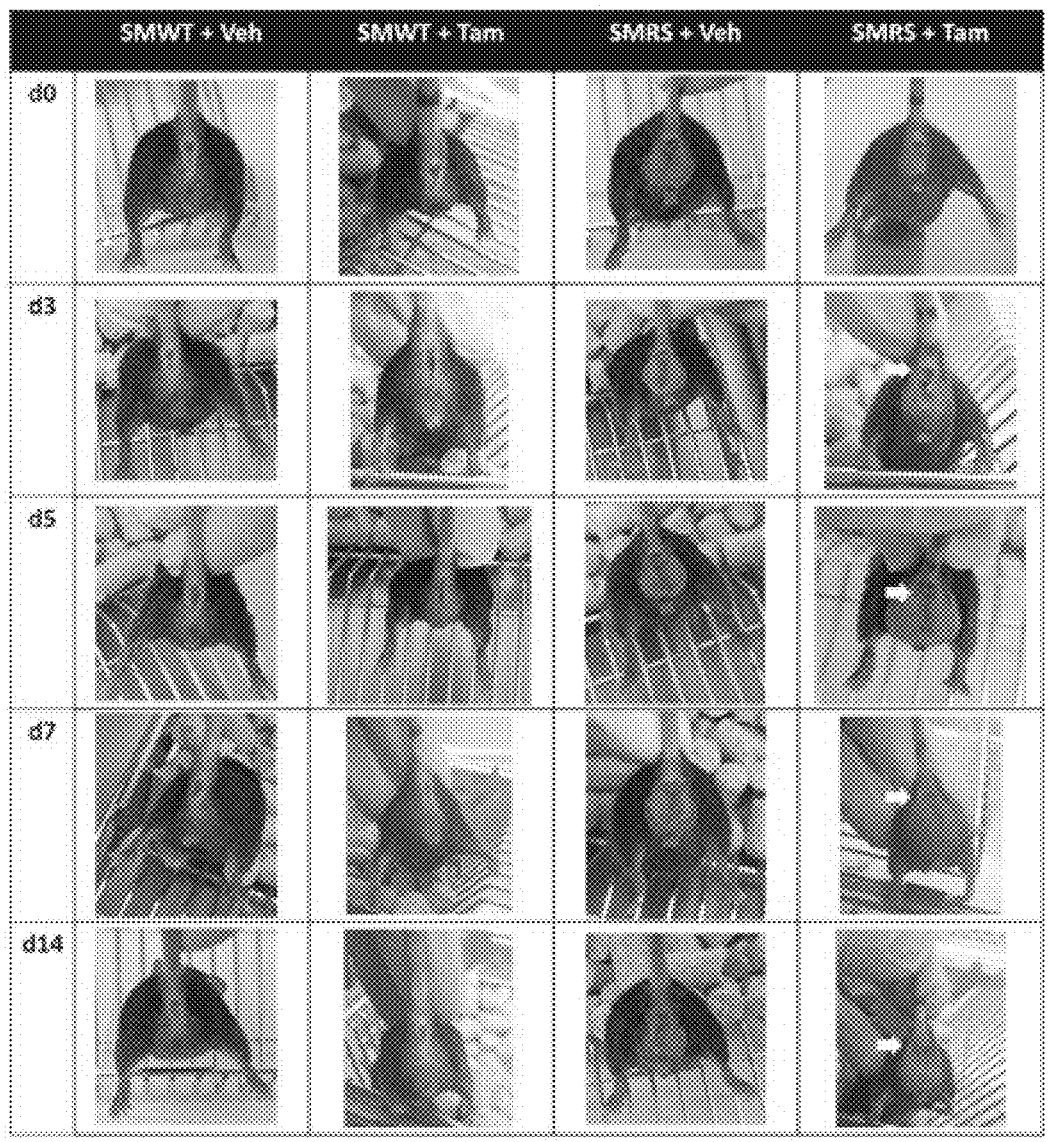
FIGS. 29A to 29C. The effect of increased IL-11 expression on SMC pathology in inflammatory bowel disorders. SMRS mice present red and swollen rectums (arrows) when IL-11 is induced with tamoxifen (Tam) compared to administration with corn oil control vehicle (Veh) or control SMWT mice with either treatment (FIG. 29A). SMRS mice produce softer and paler stools after Tam induction compared to SMWT controls (FIG. 29B). Calprotectin (S100A8/A9) levels are elevated in stool samples of SMRS mice compared to SMWT controls (FIG. 29C).

FIG. 29A shows rectums of SMRS and SMWT control mice after administration of either vehicle (corn oil) or tamoxifen (3 doses of 1 mg/kg/day). SMRS mice receiving tamoxifen present red and swollen rectums (arrows) compared to other mouse groups, indicating inflammatory bowel condition.

Figure 29B:
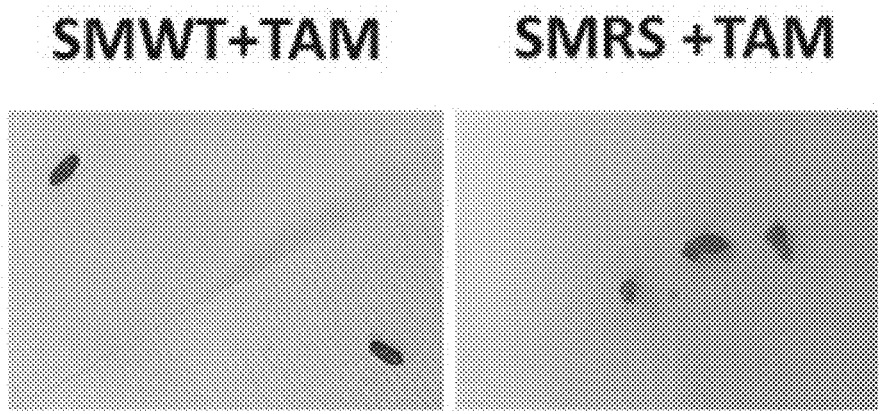

FIG. 29B depicts representative images of stool samples from SMRS and SMWT mice after tamoxifen treatment. SMRS mice produce softer and paler stools compared to SMWT controls.

Figure 29C:
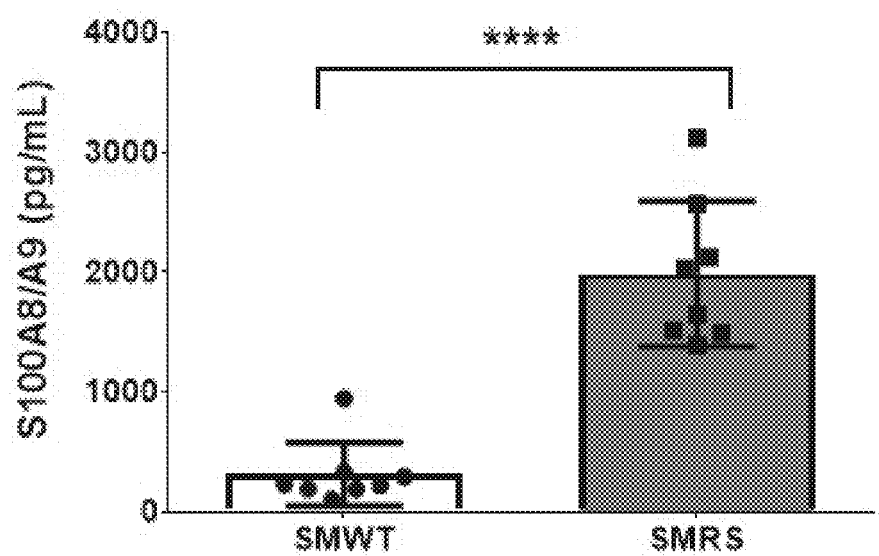

FIG. 29C shows that calprotectin (S100A8/A9) levels, reflecting inflammatory cell activity in the gut, are elevated in stool samples of SMRS mice compared to SMWT controls (n=8 per group).

Thus, tamoxifen-induced Cre-mediated IL-11 overexpression in smooth muscle cells results in inflammatory bowel phenotype in SMRS mice.

Example 19: IL-11 Overexpression Contributes to SMC Pathology in the Gastro-Intestinal Tract The effect of increased IL-11 expression on the gastro-intestinal tract was investigated using the tamoxifen-induced Cre-mediated SMC IL-11 overexpression mouse model.

Figure 30A:
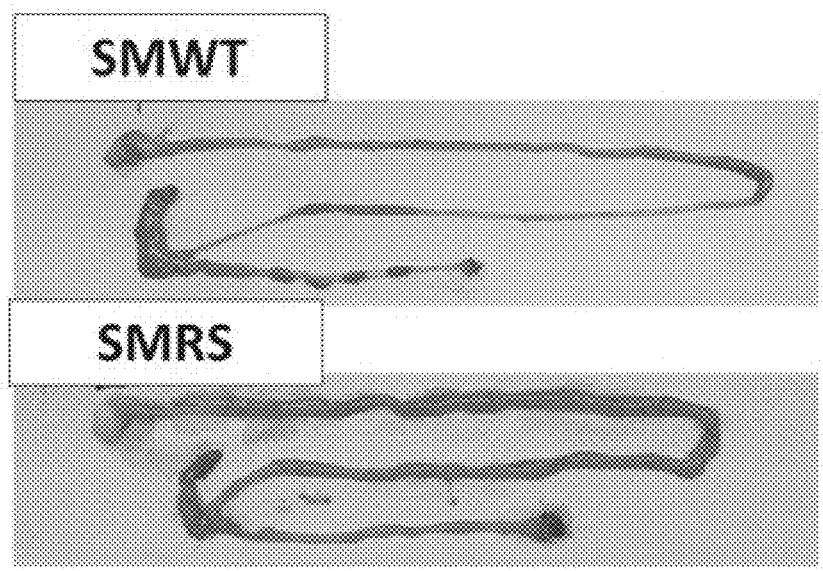
FIGS. 30A to 30C. The effect of increased IL-11 expression on SMC pathology in the gastro-intestinal tract. The gastro-intestinal tract from SMRS mice demonstrates redness and swelling compared to SMWT controls (FIG. 30A). SMRS mice show elevated IL-11 expression in the colon compared to SMWT controls (FIG. 30B). Representative sections of the colon and small intestine from SMRS mice stained with Masson's trichrome demonstrate greater wall thickness and intestinal fibrosis compared to SMWT controls (FIG. 30C).
Figure 30B:
Figure 30C:
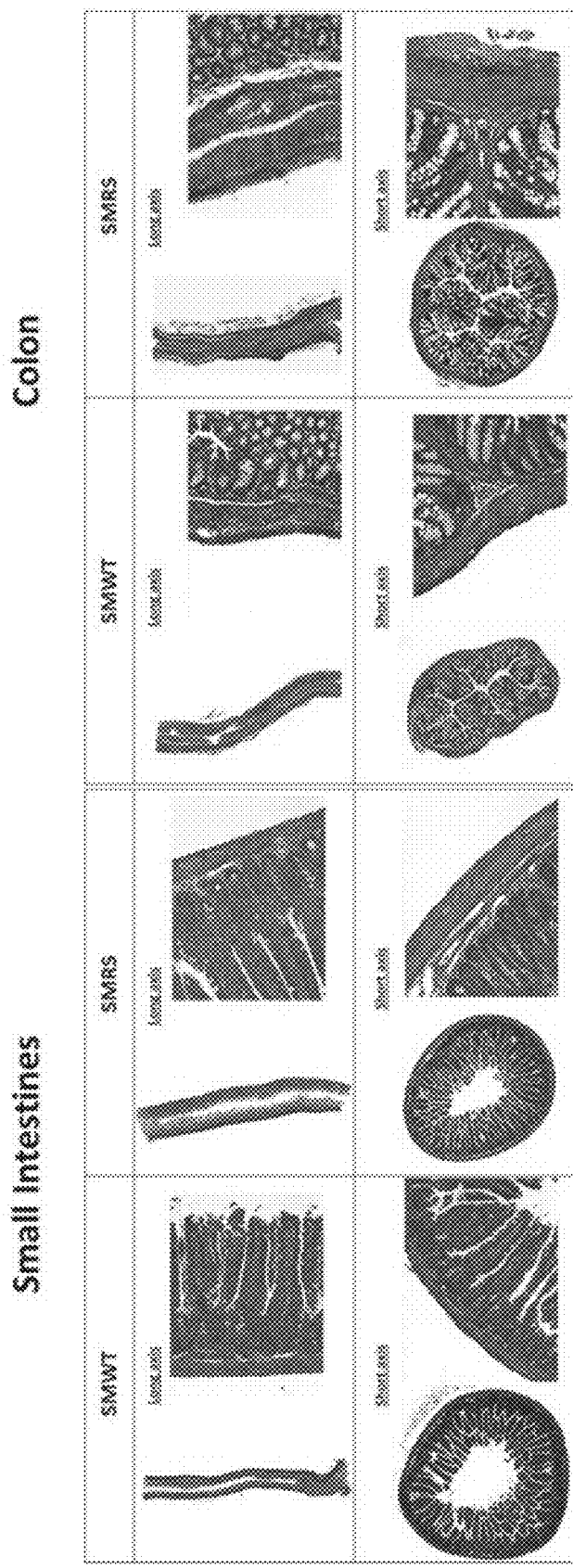

Tamoxifen induction and staining with Masson's trichrome were performed as described in Example 14. FIG. 30A shows that the isolated gastro-intestinal tract in SMRS mice demonstrates redness and swelling compared to SMWT controls. FIG. 30B demonstrates elevated IL-11 expression in the colon of 8-week-old SMRS mice compared to SMWT controls following two weeks of tamoxifen induction (n=3 per group; detected by immunoblotting). FIG. 30C depicts representative sections of the small intestine and colon from SMWT and SMRS mice stained with Masson's trichrome (n=3 per group). SMRS mice intestinal walls demonstrate greater wall thickness and intestinal fibrosis compared to controls.

Thus, tamoxifen-induced Cre-mediated IL-11 overexpression in smooth muscle cells results in inflamed gastro-intestinal tract and intestinal fibrosis.

Expression of ECM and Inflammatory Genes

RT-PCR was performed as described in Example 14.

Figure 31:
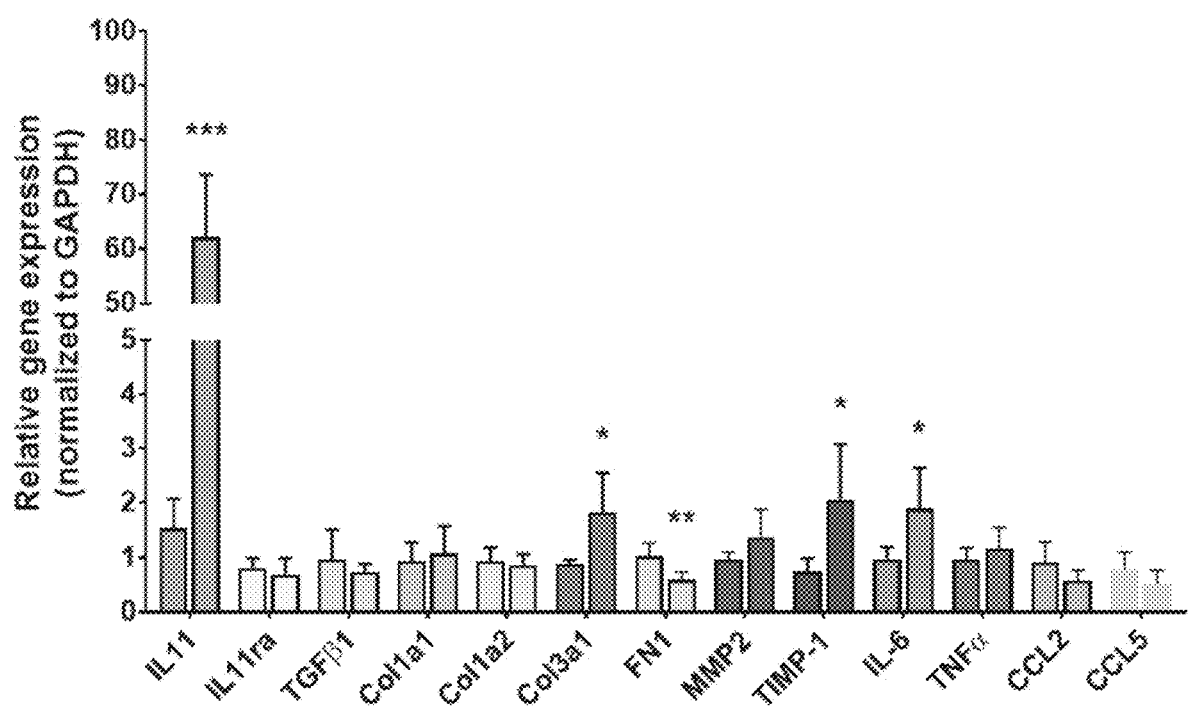
FIG. 31. Graph showing that SMRS mice have elevated expression of extracellular matrix and inflammatory genes in the colon. Left bars represent SMWT controls, right bars represent SMRS mice overexpressing IL-11 in SMCs. *, , * denote P<0.05, P<0.01 and P<0.001 respectively.

FIG. 31 shows that tamoxifen-induced Cre-mediated IL-11 overexpression in smooth muscle cells causes elevated extracellular matrix protein expression in the colon. Columns indicate average gene expression (normalized to GAPDH expression) with left bars denoting SMWT and right bars denote for SMRS groups (n=5 per group). Extracellular matrix genes includes collagens (Col1a1, Col1a2, Col3a1), fibronectin (FN1), matrix metalloproteinase (MMP2), and tissue inhibitor of matrix metalloproteinase (TIMP-1).

Inflammatory genes included interleukin-6 (IL-6), tumour necrosis factor alpha (TNFα), C—C motif chemokine ligand-2 and -5 (CCL2 and CCL5 respectively). Statistical analyses were performed using two-tailed unpaired T-test. *, , * denote P<0.05, P<0.01 and P<0.001 respectively.

Example 20: IL-11 Expression in Marfan's Syndrome

Marfan's Syndrome (MFS) is an autosomal dominant connective tissue condition with elevated TGFβ signalling. MFS mice were used to investigate IL-11 expression.

All mice were from a C57BL/6 genetic background and they were bred and housed in the same room and provided food and water ad libitum. MFS (B6.129-Fbn1$^{tm1Hpd}$/J) mice were purchased from Jackson Laboratory (012885; Bar Harbor, Me.). Heterozygous mice that develop classical manifestations of human disease (including aortic aneurysms and lung defects) were used in experiments.

Western blot analysis was carried out on total protein extracts from mouse heart, lung and thoracic aorta.

Frozen tissues were homogenized by gentle rocking in lysis buffer (RIPA buffer containing protease and phosphatase inhibitors (Roche)) followed by centrifugation to clear the lysate. Equal amounts of protein lysates were separated by SDS-PAGE, transferred to a PVDF membrane, and incubated overnight with anti-IL11 (MAB218, R&D systems) and anti-GAPDH (2118, Cell Signaling) antibodies. Proteins were visualized using the ECL detection system (Pierce) with the appropriate secondary antibodies: anti-rabbit HRP (7074, Cell Signaling) or anti-mouse HRP (7076, Cell Signaling).

Figure 32A:
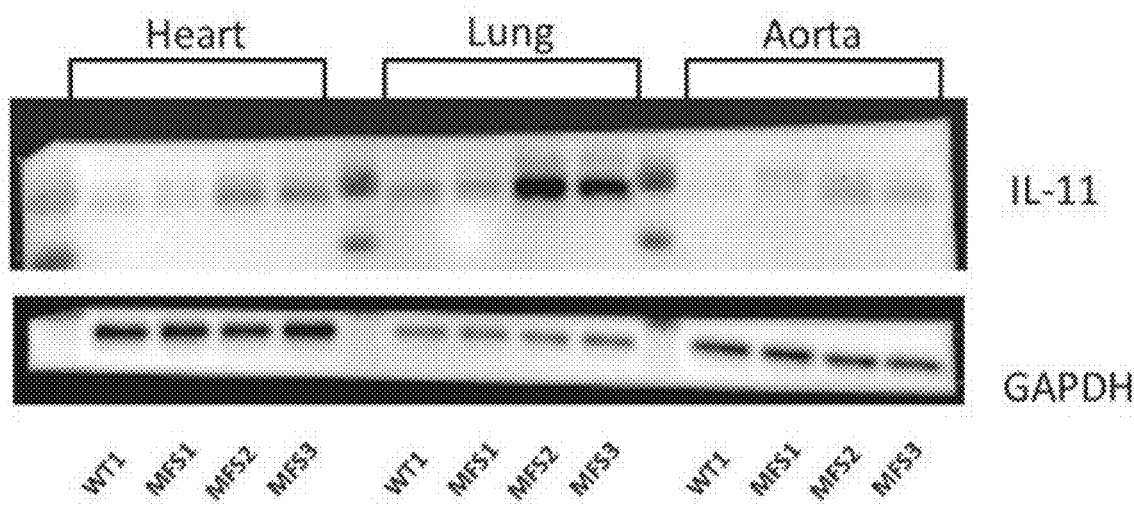
FIGS. 32A to 32D. IL-11 is upregulated in heart, lung and aorta tissues of mice with Marfan's Syndrome (MFS.
Figure 32B:
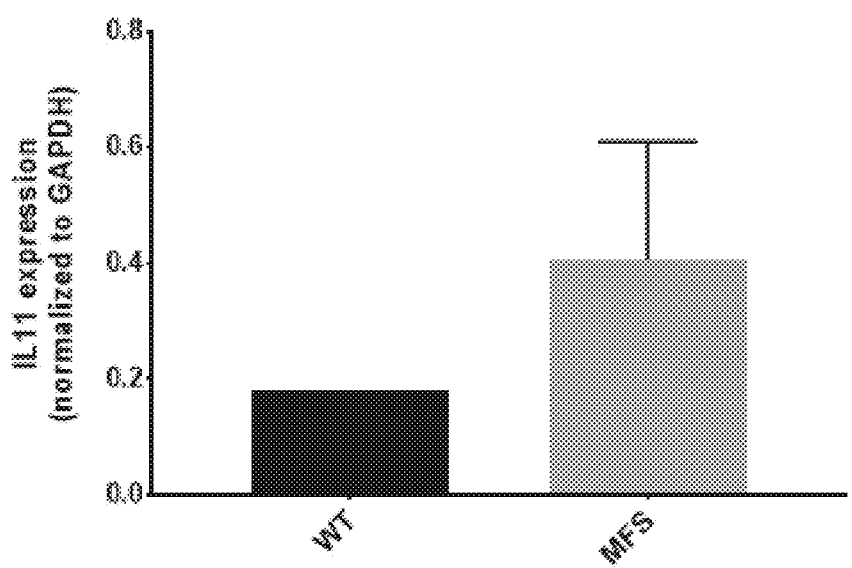
Figure 32C:
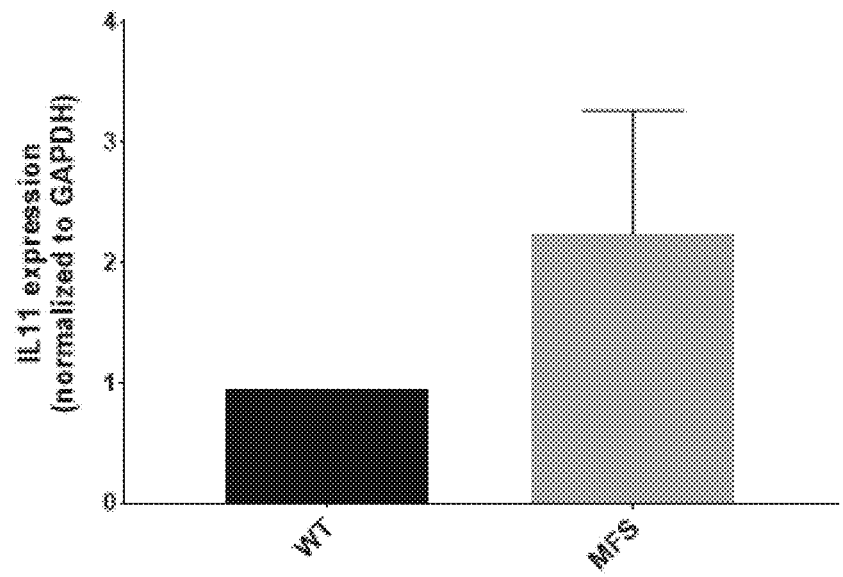
Figure 32D:
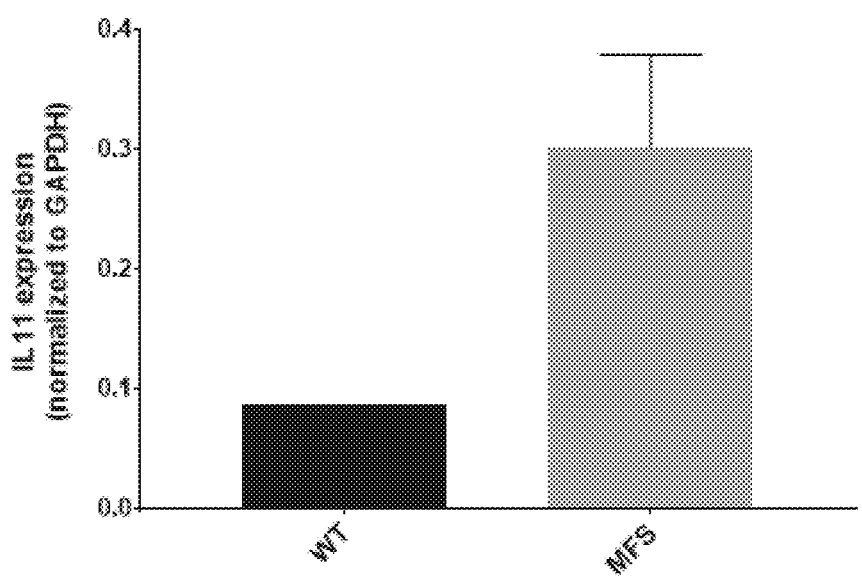

FIGS. 32A-D shows that IL-11 is upregulated in the heart, lung and aorta in Marian's Syndrome (MFS) mice. FIG. 32A shows that heart, lung, and aorta tissue of MFS mice demonstrated increased IL-11 expression as compared to wild-type (WT) controls assessed by western blotting. FIGS. 32B to 32D depict densitometry assessment of IL-11 expression as compared to GAPDH expression in heart, lung, and aorta of MFS mice, respectively.

Example 21: Effect of IL-11 Inhibition on Aortic Remodelling

Transverse aortic constriction (TAC) in mice was employed to analyse the effect of inhibition of IL-11-mediated signalling on TAC-induced aortic remodelling of SMCs.

All mice were from a C57BL/6 genetic background and they were bred and housed in the same room and provided food and water ad libitum. Animals underwent thoracotomy with ascending aortic constriction with survival. Terminal studies were conducted at 2 weeks post TAC surgery. Age-matched sham controls underwent the same operative procedure without TAC. Trans-thoracic two-dimensional Doppler echocardiography was used to confirm increased pressure gradients (>40 mmHg) indicative of successful TAC. Mice were euthanized at 2 weeks post-TAC for histological and molecular assessments. For post-operative drug treatment, anti-IL11, anti-IL11Rα or IgG control antibodies were given intraperitoneally at a dose of 20 mg/kg twice per week for two consecutive weeks.

The results are shown in FIGS. 33A to 33D, which demonstrate that TAC-induced aortic remodelling is reduced by inhibiting IL-11-mediated signalling using anti-IL11RA antibodies, despite maintenance of pressure overload in mice.

Figure 33A:
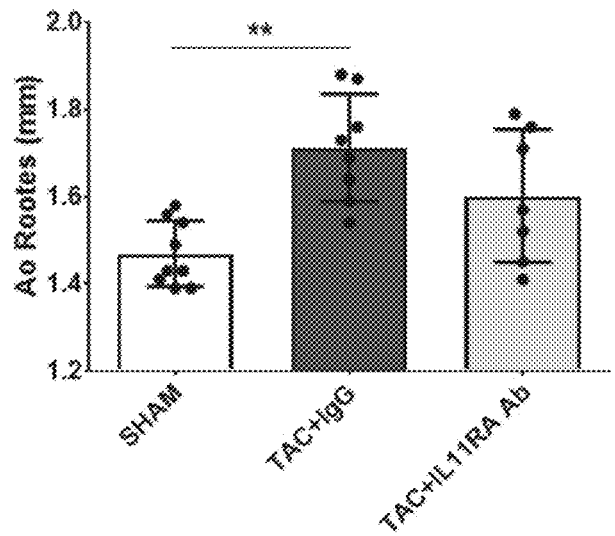
FIGS. 33A to 33D. Thoracic aortic constriction (TAC)-induced aortic remodelling is reduced by inhibiting IL-11-mediated signalling using anti-IL11RA antibodies.
Figure 33B:
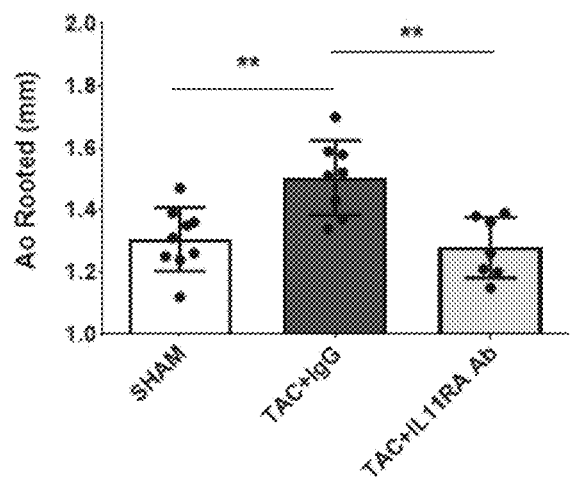
Figure 33C:
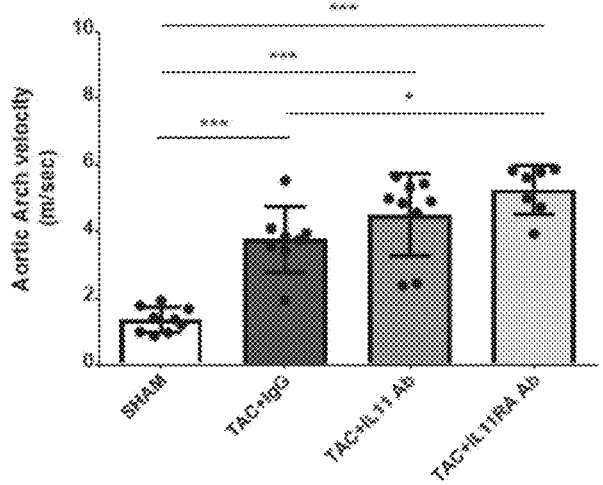
Figure 33D:
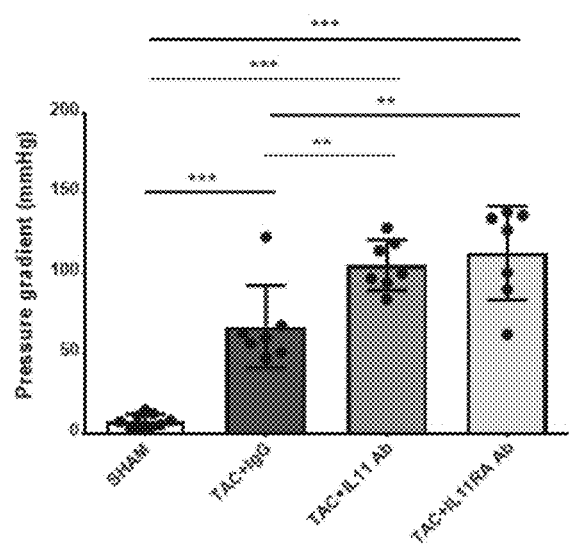

FIGS. 33A and 33B show aortic root internal dimension at end-systole and end-diastole. FIGS. 33C and 33D show aortic arch peak velocity and pressure gradient, respectively. Statistical analyses were conducted with one-way ANOVA with Sidak post-hoc analyses for multiple comparisons. *, , * denote P<0.05, P<0.01 and P<0.001 respectively.

Representative sections of proximal thoracic aorta were fixed in 10% neutral-buffered formalin for 24-48 hours, dehydrated and embedded in formalin. Sections (5 μm) were stained with Masson's trichome staining for collagen assessment, as described in Example 14.

Figure 34:
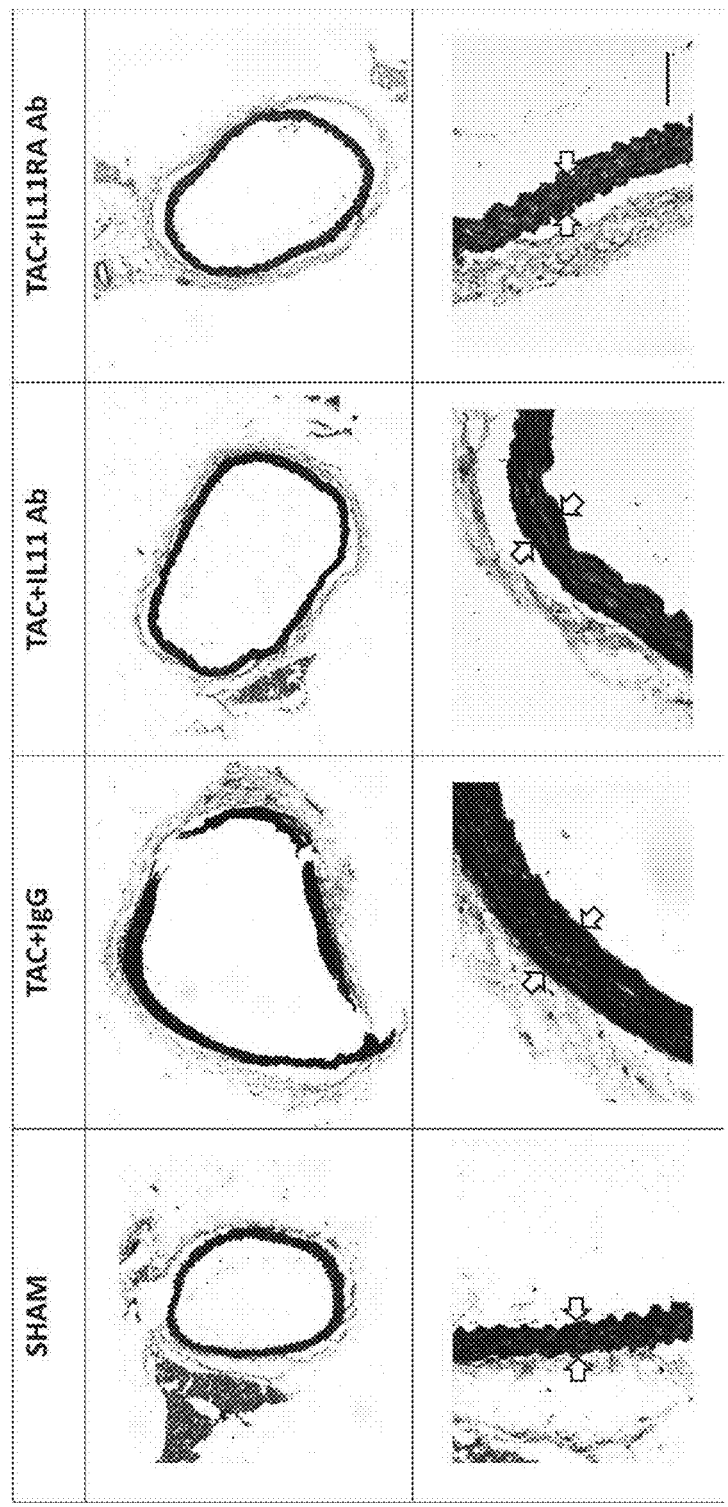
FIG. 34. Representative sections of proximal thoracic aorta were stained with Masson's trichrome (n=5/group), showing that TAC-induced aortic remodelling is ameliorated with neutralizing IL-11 and IL-11Rα antibodies, see arrows. Scale bar represents 100 μm.

FIG. 34 shows that TAC-induced aortic remodelling is ameliorated with neutralizing IL-11 and IL-11Rα antibodies, see arrows. Representative sections of proximal thoracic aorta were stained with Masson's trichrome (n=5/group). Scale bar represents 100 μm.

Example 22: Effect of Inhibiting IL-11-Mediated Signalling on Aortic VSMC Migration Mouse VSMCs were isolated and cultured using a modified protocol adapted from published literature (Metz, Richard P., et al. *Cardiovascular Development*. Humana Press, Totowa, N.J., 2012. 169-176; Weber, Sven C., et al. *Pediatric research* 70.3 (2011): 236). Thoracic aortas were excised from mice treated with recombinant mouse IL-11 (5 ng/ml) and recombinant mouse TGFβ1 (5 ng/ml) with and without anti-IL11 antibody (2 μg/ml) or equivalent concentration of IgG isotype control. The aortic tissue was minced, digested for 45 minutes in M231 medium containing 1% antibiotic-antimycotic and 0.25 mg/mL Liberase™ (Roche) with mild agitation at 37° C. and subsequently explant cultured in complete M231 supplemented with SMGS and 1% antibiotic-antimycotic at 37° C. Mixed cells were outgrown from digested aortic tissue and at 80-90% confluence at passage 1, VSMCs were enriched via negative selection with magnetic beads against CD45 (leukocytes; 130-052-301, Miltenyi Biotec), CD90.2 (fibroblasts; 130-049-101, Miltenyi Biotec), and CD31 (endothelial cells; 130-097-418, Millenyi Biotec) using the MidiMACS separator according to manufacturer's instructions. Mouse aortic VSMCs were used for downstream experiments at low passages between 3 to 5. To assess VSMC migration, in vitro scratch wound assays were performed with confluent monolayers of murine VSMCs for 24 h.

Figure 35A:
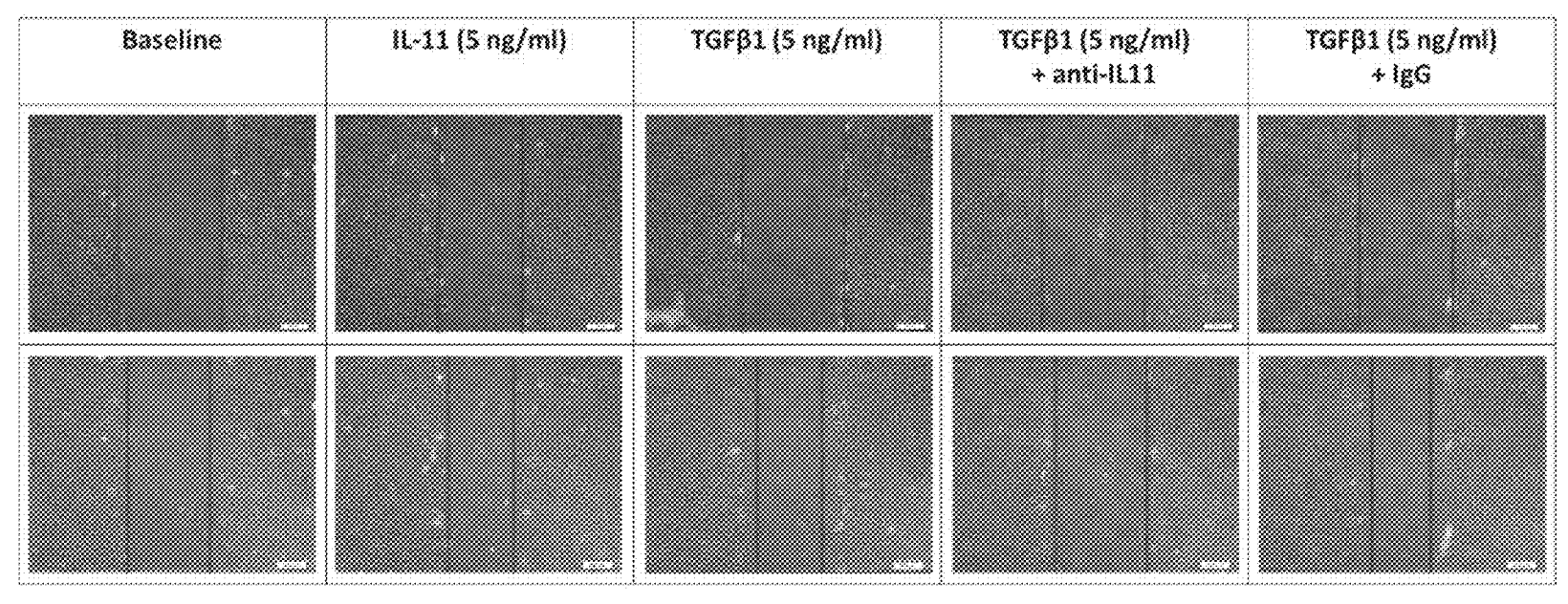
Figure 35B:
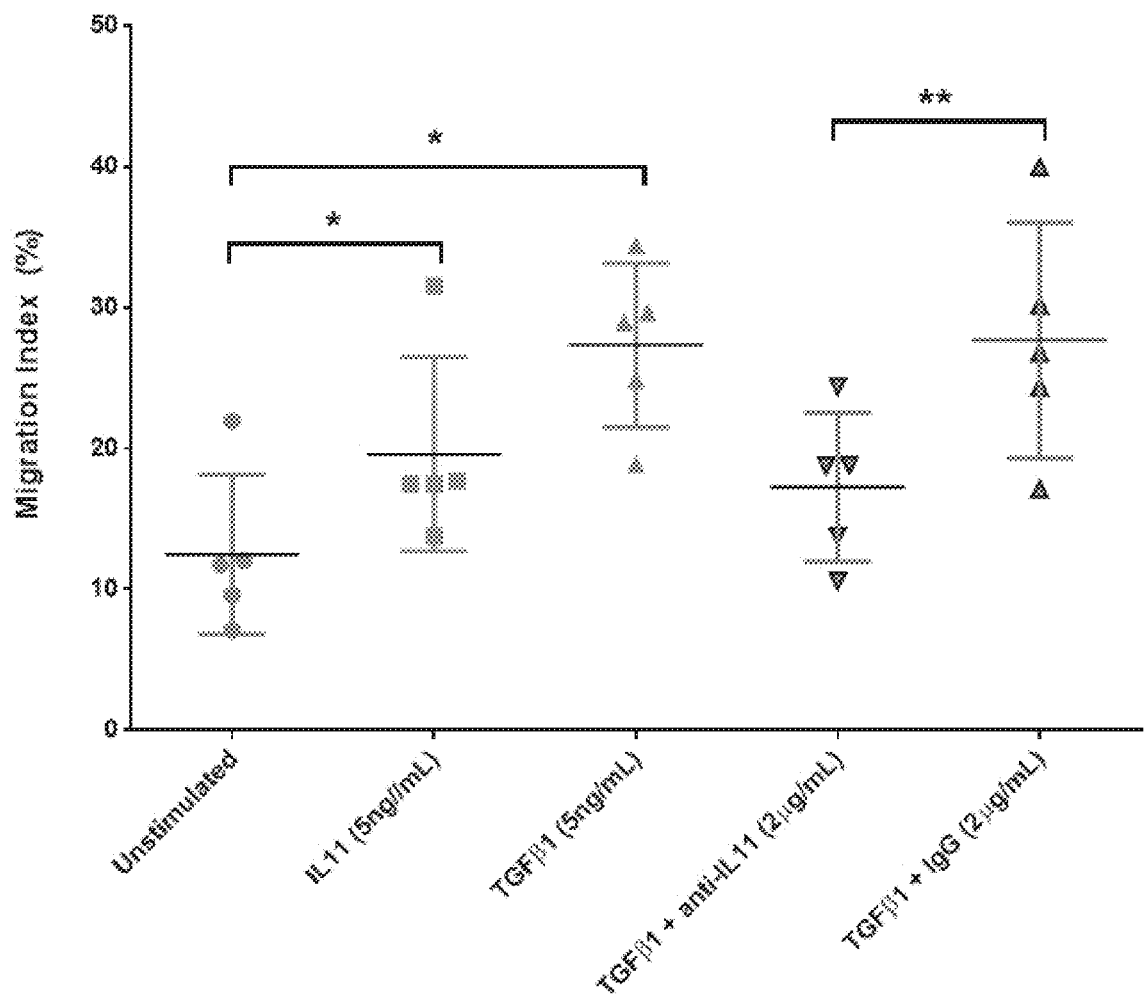

FIGS. 35A and 35B show that antibody inhibition of IL-11-mediated signalling neutralizes TGFβ1-mediated murine aortic VSMC migration. Representative images (35A) and cumulative plots (35B) show migration of VSMCs from mice treated with recombinant mouse IL-11 (5 ng/ml) and recombinant mouse TGFβ1 (5 ng/ml) with and without anti-IL11 antibody (2 µg/ml) or equivalent concentration of IgG isotype control for 24 h. The wound area was imaged at 0 h (upper panels) and 24 h (lower panels), and migration was calculated using ImageJ software with the MRI wound healing tool, as described below. Scale bar indicates 200 µm distance. All data expressed as mean±SD. Statistical significance was established with two-way ANOVA with Sidak's multiple comparisons. *, ** denotes $P<0.05$, $P<0.01$ respectively.

In another study, the effect of multiple known stimulants of VSMC migration was assessed in murine aortic VSMCs with IL-11Rα ablation.

Mouse VSMCs were isolated and cultured using a modified protocol adapted from published literature (Metz, Richard P., et al. *Cardiovascular Development*. Humana Press, Totowa, N.J., 2012. 169-176; Weber, Sven C., et al. *Pediatric research* 70.3 (2011): 236). Briefly, 4 to 6 weeks old mice lacking functional alleles for IL11 ra1 (Il11ra1−/−, KO) and their wild-type littermates (Il11ra1+/+, WT) were euthanised and the thoracic aorta excised for VSMC cultures. The thoracic aorta from WT and KO mice were minced, digested for 45 minutes in M231 medium containing 1% antibiotic-antimycotic and 0.25 mg/mL Liberase™ (Roche) with mild agitation at 37° C. and subsequently explant cultured in complete M231 supplemented with SMGS and 1% antibiotic-antimycotic at 37° C. Mixed cells were outgrown from digested aortic tissue and at 80-90% confluence at passage 1, VSMCs were enriched via negative selection with magnetic beads against CD45 (leukocytes; 130-052-301, Miltenyi Biotec), CD90.2 (fibroblasts; 130-049-101, Miltenyi Biotec), and CD31 (endothelial cells; 130-097-418, Miltenyi Biotec) using the MidiMACS separator according to manufacturer's instructions. Mouse aortic VSMCs were used for downstream experiments at low passages between 3 to 5.

To assess VSMC migration, in vitro scratch wound assays were performed with confluent monolayers of murine VSMCs. After serum starvation with low serum media (M231 containing 0.2% FBS) for 24 h, a linear scratch was created with a sterile pipette tip and cells were treated with: either M231 only (unstimulated), angiotensin II (ANGII, 100 µM) (Sigma-Aldrich), mouse IL-11 (5 ng/ml) (Genscript) or mouse TGFβ1 (5 ng/ml) (R&D systems) for 48 h. The wound area were analysed using ImageJ with the "MRI wound healing tool" plugin (available from http//dev.m-ri.cnrs.fr/projects/imagej-macros/wiki/Wound_Healing_Tool). The wound area was imaged at 0 and 48 h and migration was calculated using the formula "migration= (A0−A1)/A0×100", wherein A0 is the area of the wound at 0 h and A1 is the area unoccupied by VSMCs after 24 h or 48 h. 6 to 10 random regions were analysed per treatment and averaged. Treatment duration of 48 h was presented for murine stimulation studies in WT and KO VSMCs.

Figure 36A:
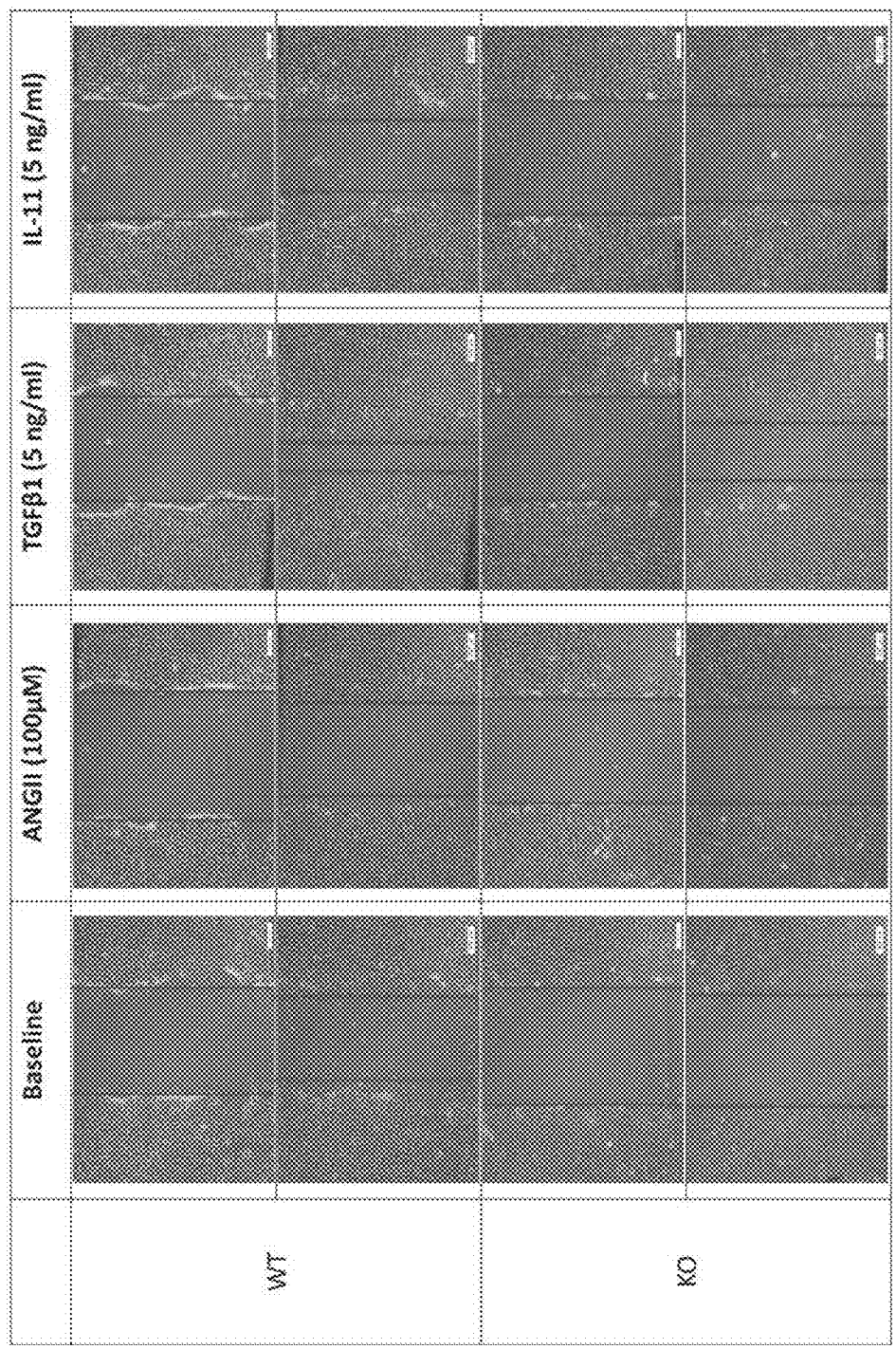
FIGS. 36A and 36B. Representative images (FIG. 36A) and cumulative plots (FIG. 36B) show wild-type (WT) and IL11ra1-ablated (KO) mice treated with no stimulants, angiotensin II (ANGII, 100 μM), recombinant mouse TGFβ1 (5 ng/ml), and recombinant mouse IL-11 (5 ng/ml) for 0 h (upper panels) and 48 h (lower panels). Scale bar represents 200 μm. *, , *, **** denote P<0.05, P<0.01, P<0.001 and P<0.0001 respectively.
Figure 36B:
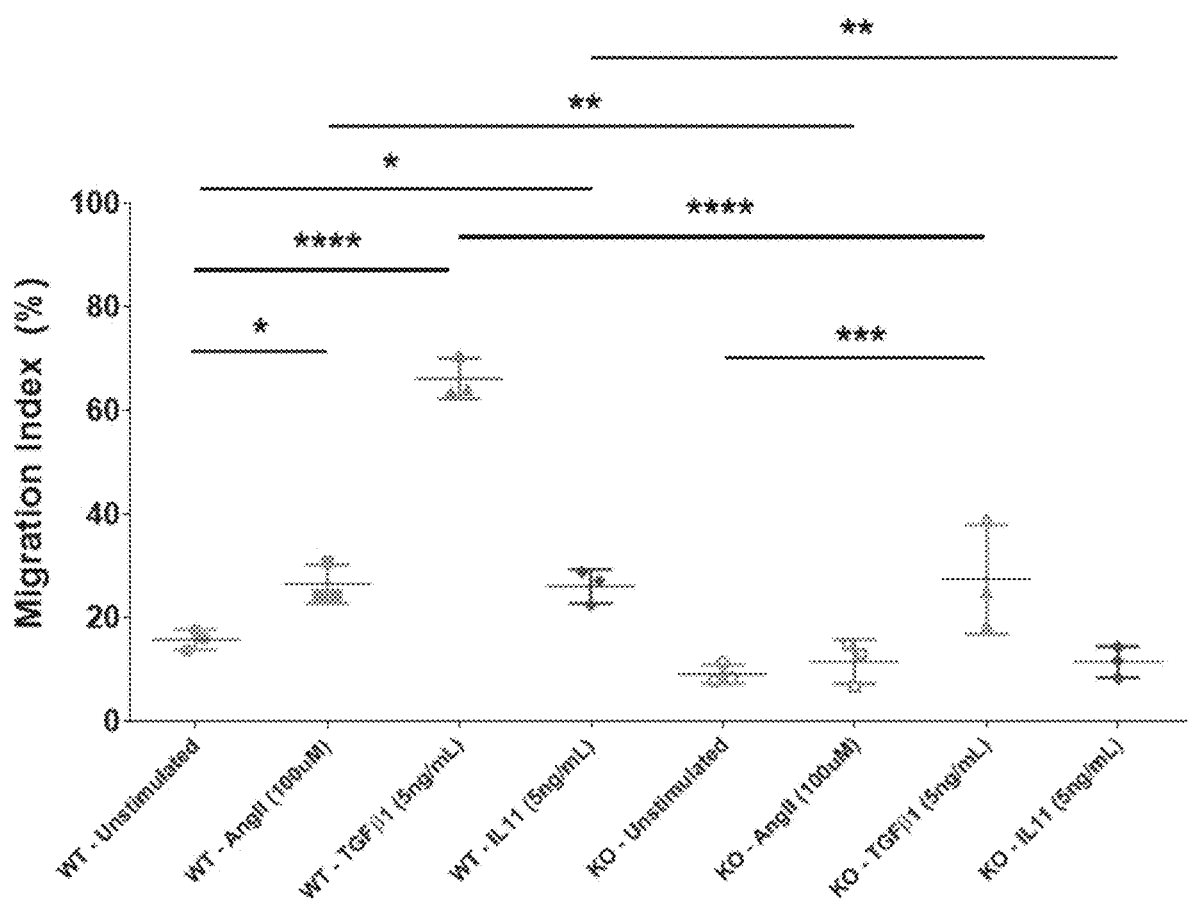

The results are shown in FIGS. 36A and 36B. Representative images (36A) and cumulative plots (36B) show wild-type (WT) and IL11 ra1-ablated (KO) mice treated with no stimulants, angiotensin II (ANGII, 100 µM), recombinant mouse TGFβ1 (5 ng/ml), and recombinant mouse IL-11 (5 ng/ml) for 48 h. The wound area was imaged at 0 h (upper panels) and 48 h (lower panels), and migration was calculated using ImageJ software with the MRI wound healing tool. Scale bar indicates 200 µm distance. All data expressed as mean±SD. Statistical significance was established with two-way ANOVA with Dunnett's multiple comparisons. *, , *, **** denote $P<0.05$, $P<0.01$, $P<0.001$ and $P<0.0001$ respectively.

Thus, IL-11Rα ablation in murine aortic VSMCs is protective against multiple known stimulants of VSMC migration, including IL-11.

REFERENCES

1. Du, X. & Williams, D. A. Interleukin-11: review of molecular, cell biology, and clinical use. *Blood* 89, 3897-3908 (1997).
2. Hegner, B. et al. Intrinsic Deregulation of Vascular Smooth Muscle and Myofibroblast Differentiation in Mesenchymal Stromal Cells from Patients with Systemic Sclerosis. *PLoS One* 11, e0153101 (2016).
3. Guo, X. & Chen, S.-Y. Transforming growth factor-β and smooth muscle differentiation. *World J. Biol. Chem.* 3, 41-52 (2012).
4. Hautmann, M. B., Madsen, C. S. & Owens, G. K. A Transforming Growth Factor β (TGFβ) Control Element Drives TGFβ-induced Stimulation of Smooth Muscle α-Actin Gene Expression in Concert with Two CArG Elements. *J. Biol. Chem.* 272, 10948-10956 (1997).
5. Ding, R., Darland, D. C., Parmacek, M. S. & D'Amore, P. A. Endothelial-mesenchymal interactions in vitro reveal molecular mechanisms of smooth muscle/pericyte differentiation. *Stem Cells Dev.* 13, 509-520 (2004).
6. Taki, H. et al. Monokine stimulation of interleukin-11 production by human vascular smooth muscle cells in vitro. *Atherosclerosis* 144, 375-380 (1999).
7. Zimmerman, M. A. et al. Interleukin-11 attenuates human vascular smooth muscle cell proliferation. *Am. J. Physiol. Heart Circ. Physiol.* 283, H175-80 (2002).
8. Postlethwaite, Postlethwaite, Pattanaik, D. & Brown, M. Vascular involvement in systemic sclerosis (scleroderma). *J. Inflamm. Res.* 105 (2011).
9. Matucci-Cerinic, M., Kahaleh, B. & Wigley, F. M. Review: Evidence That Systemic Sclerosis Is a Vascular Disease. *Arthritis & Rheumatism* 65, 1953-1962 (2013).
10. Tuder, R. M., Marecki, J. C., Richter, A., Fijalkowska, I. & Flores, S. Pathology of pulmonary hypertension. *Clin. Chest Med.* 28, 23-42, vii (2007).
11. Boin, F. et al. Oxidative stress-dependent activation of collagen synthesis is induced in human pulmonary smooth muscle cells by sera from patients with scleroderma-associated pulmonary hypertension. *Orphanet J. Rare Dis.* 9, 123 (2014).
12. Rabinovitch, M. Molecular pathogenesis of pulmonary arterial hypertension. *J. Clin. Invest.* 122, 4306-4313 (2012).
13. Gordon, K. J. & Blobe, G. C. Role of transforming growth factor-beta superfamily signalling pathways in human disease. *Biochim. Biophys. Acta* 1782, 197-228 (2008).

14. Crosas-Molist, E. et al. Vascular smooth muscle cell phenotypic changes in patients with Marfan syndrome. *Arterioscler. Thromb. Vasc. Biol.* 35, 960-972 (2015).
15. Matt, P. et al. Circulating transforming growth factor-beta in Marian syndrome. *Circulation* 120, 526-532 (2009).
16. Holm, T. M. et al. Noncanonical TGFbeta signalling contributes to aortic aneurysm progression in Marian syndrome mice. *Science* 332, 358-361 (2011).
17. Lindsay, M. E. & Dietz, H. C. Lessons on the pathogenesis of aneurysm from heritable conditions. *Nature* 473, 308-316 (2011).
18. Dietz, H. C. 2006 Curt Stern Award Address. Marfan syndrome: from molecules to medicines. *Am. J. Hum. Genet.* 81, 662-667 (2007).
19. Goumans, M.-J., Liu, Z. & ten Dijke, P. TGF-beta signalling in vascular biology and dysfunction. *Cell Res.* 19, 116-127 (2009).
20. Starke, R. M. et al. Vascular smooth muscle cells in cerebral aneurysm pathogenesis. *Trans. Stroke Res.* 5, 338-346 (2014).
21. Nakajima, N., Nagahiro, S., Sano, T., Satomi, J. & Satoh, K. Phenotypic modulation of smooth muscle cells in human cerebral aneurysmal walls. *Acta Neuropathol.* 100, 475-480 (2000).
22. Nikol, S. et al. Expression of transforming growth factor-beta 1 is increased in human vascular restenosis lesions. *J. Clin. Invest.* 90, 1582-1592 (1992).
23. Nabel, E. G. et al. Direct transfer of transforming growth factor beta 1 gene into arteries stimulates fibrocellular hyperplasia. *Proc. Natd. Acad. Sci. U.S.A* 90, 10759-10763 (1993).
24. Wolf, Y. G., Rasmussen, L. M. & Ruoslahti, E. Antibodies against transforming growth factor-beta 1 suppress intimal hyperplasia in a rat model. *J. Clin. Invest.* 93, 1172-1178 (1994).
25. Edlin, R. S. et al. Characterization of primary and restenotic atherosclerotic plaque from the superficial femoral artery: Potential role of Smad3 in regulation of SMC proliferation. *J. Vasc. Surg.* 49, 1289-1295 (2009).
26. Tsai, S. et al. TGF-beta through Smad3 signaling stimulates vascular smooth muscle cell proliferation and neointimal formation. *Am. J. Physiol. Heart Circ. Physiol.* 297, H540-9 (2009).
27. Mallawaarachchi, C. M., Weissberg, P. L. & Siow, R. C. M. Smad7 gene transfer attenuates adventitial cell migration and vascular remodeling after balloon injury. *Arterioscler. Thromb. Vasc. Biol.* 25, 1383-1387 (2005).
28. Louis, S. F. & Zahradka, P. Vascular smooth muscle cell motility: From migration to invasion. *Exp. Clin. Cardiol.* 15, e75-85 (2010).
29. Suwanabol, P. A., Kent, K. C. & Liu, B. TGF-β and restenosis revisited: a Smad link. *J. Surg. Res.* 167, 287-297 (2011).
30. McCaffrey, T. A. et al. Genomic instability in the type II TGF-beta1 receptor gene in atherosclerotic and restenotic vascular cells. *J. Chin. Invest.* 100, 2182-2188 (1997).
31. Mallat, Z. et al. Inhibition of transforming growth factor-beta signalling accelerates atherosclerosis and induces an unstable plaque phenotype in mice. *Circ. Res.* 89, 930-934 (2001).
32. Robertson, A.-K. L. et al. Disruption of TGF-β signalling in T cells accelerates atherosclerosis. *J. Clin. Invest.* 112, 1342-1350 (2003).
33. Grainger, D. J., Mosedale, D. E., Metcalfe, J. C. & Böttinger, E. P. Dietary fat and reduced levels of TGF-beta1 act synergistically to promote activation of the vascular endothelium and formation of lipid lesions. *J. Cell Sci.* 113 (Pt 13), 2355-2361 (2000).
34. Grainger, D. J., Witchell, C. M. & Metcalfe, J. C. Tamoxifen elevates transforming growth factor-beta and suppresses diet-induced formation of lipid lesions in mouse aorta. *Nat. Med.* 1, 1067-1073 (1995).
35. O'Connor, S. C. & Gornik, H. L. Recent developments in the understanding and management of fibromuscular dysplasia. *J. Am. Heart Assoc.* 3, e001259 (2014).
36. Begelman. S. M. & Olin, J. W. Fibromuscular dysplasia. *Curr. Opin. Rheumatol.* 12, 41-47 (2000).
37. Ganesh, S. K. et al. Clinical and biochemical profiles suggest fibromuscular dysplasia is a systemic disease with altered TGF-β expression and connective tissue features. *FASEB J.* 26, 3313-3324 (2014).
38. Weber, B. R. & Dieter, R. S. Renal artery stenosis: epidemiology and treatment. *Int. J. Nephrol. Renovasc. Dis.* 7, 169-181 (2014).
39. El Mabrouk, M., Diep, 0. N., Benkirane, K., Touyz, R. M. & Schiffrin, E. L. SAM68: a downstream target of angiotensin II signalling in vascular smooth muscle cells in genetic hypertension. *Am. J. Physiol. Heart Circ. Physiol.* 286, H1954-62 (2004).
40. Zhang, L. et al. Impaired peroxisome proliferator-activated receptor-gamma contributes to phenotypic modulation of vascular smooth muscle cells during hypertension. *J. Biol. Chem.* 285, 13668-13677 (2010).
41. Warren, H. R. et al. Genome-wide association analysis identifies novel blood pressure loci and offers biological insights into cardiovascular risk. *Nat. Genet.* 49, 403-415 (2017).
42. Cove-Smith, A. & Hendry, B. M. The regulation of mesangial cell proliferation. *Nephron Exp. Nephrol.* 108, e74-9 (2008).
43. Diamond, J. R. & Karnovsky, M. J. Focal and segmental glomerulosclerosis: analogies to atherosclerosis. *Kidney Int.* 33, 917-924 (1988).
44. Herrera, G. A. Plasticity of mesangial cells: a basis for understanding pathological alterations. *Ultrastruct. Pathol.* 30, 471-479 (2006).
45. Loeffler, I. & Wolf, G. Transforming growth factor-β and the progression of renal disease. *Nephrol. Dial. Transplant* 29 Suppl 1, 37-45 (2014).
46. Santibanez, J. F., Krstic, J., Quintanilla, M. & Bernabeu, C. TGF-β Signalling and Its Role in Cancer Progression and Metastasis, in *eLS* 1-9 (2016).
47. Freyer, A. M., Johnson, S. R. & Hall, I. P. Effects of growth factors and extracellular matrix on survival of human airway smooth muscle cells. *Am. J. Respir. Cell Mol. Biol.* 25, 569-576 (2001).
48. Chung, K. F. The role of airway smooth muscle in the pathogenesis of airway wall remodeling in chronic obstructive pulmonary disease. *Proc. Am. Thorac. Soc.* 2, 347-54; discussion 371-2 (2005).
49. Chen, G. & Khalil, N. TGF-beta1 increases proliferation of airway smooth muscle cells by phosphorylation of map kinases. *Respir. Res.* 7, 2 (2006).
50. Ojiaku, C. A., Yoo, E. J. & Panettieri, R. A., Jr. Transforming Growth Factor β1 Function in Airway Remodeling and Hyperresponsiveness. The Missing Link? *Am. J. Respir. Cell Mol. Biol.* 56, 432-442 (2017).
51. McMillan, S. J., Xanthou, G. & Lloyd, C. M. Manipulation of allergen-induced airway remodeling by treatment with anti-TGF-beta antibody: effect on the Smad signalling pathway. *J. Immunol.* 174, 5774-5780 (2005).

52. Johnson, P. R. et al. Airway smooth muscle cell proliferation is increased in asthma. *Am. J. Respir. Crit. Care Med.* 164, 474-477 (2001).
53. Doeing, D. C. & Solway, J. Airway smooth muscle in the pathophysiology and treatment of asthma. *J. Appl. Physiol.* 114, 834-843 (2013).
54. Takizawa, H. et al. Increased Expression of Transforming Growth Factor-β1 in Small Airway Epithelium from Tobacco Smokers and Patients with Chronic Obstructive Pulmonary Disease (COPD). *Am. J. Respir. Crit. Care Med.* 163, 1476-1483 (2001).
55. Stanzel, R. D. P., Lourenssen, S., Nair, D. G. & Blennerhassett, M. G. Mitogenic factors promoting intestinal smooth muscle cell proliferation. *Am. J. Physiol. Cell Physiol.* 299, C805-17 (2010).
56. Graham, M. F., Bryson. G. R. & Diegelmann, R. F. Transforming growth factor beta 1 selectively augments collagen synthesis by human intestinal smooth muscle cells. *Gastroenterology* 99, 447-453(1990).
57. Zhang, H., Xiong, Z.-M. & Cao, K. Mechanisms controlling the smooth muscle cell death in progeria via down-regulation of poly(ADP-ribose) polymerase 1. *Proc. Natl. Acad. Sci. U.S.A* 111, E2261-70 (2014).
58. Aliper, A. M. et al. Signalling pathway activation drift during aging: Hutchinson-Gilford Progeria Syndrome fibroblasts are comparable to normal middle-age and old-age cells. *Aging* 7, 26-37 (2015).
59. Bierie, B. et al. Abrogation of TGF-beta signalling enhances chemokine production and correlates with prognosis in human breast cancer. *J. Clin. Invest.* 119, 1571-1582 (2009).
60. Shull, M. M. et al. Targeted disruption of the mouse transforming growth factor-beta 1 gene results in multifocal inflammatory disease. *Nature* 359, 693-699 (1992).
61. GTEx Consortium. The Genotype-Tissue Expression (GTEx) project. *Nat. Genet.* 45, 580-585 (2013).
62. Andersson, R. et al. An atlas of active enhancers across human cell types and tissues. *Nature* 507, 455-461 (2014).
63. Love, M. I., Huber, W. & Anders, S. Moderated estimation of fold change and dispersion for RNA-seq data with DESeq2. (2014). doi:10. 1101/002832
64. Dams-Kozlowska, H. et al. A designer hyper interleukin 11 (H11) is a biologically active cytokine. *BMC Biotechnol.* 12, 8 (2012).
65. Sarah J. Holdsworth-Carson, Marina Zaitseva, Beverley J. Vollenhoven, Peter A. W. Rogers; Clonality of smooth muscle and fibroblast cell populations isolated from human fibroid and myometrial tissues, MHR: Basic science of reproductive medicine, Volume 20, Issue 3, 1 Mar. 2014, Pages 250-259.
66. Nierth-Simpson E N, Martin M M, Chiang T-C, et al. Human Uterine Smooth Muscle and Leiomyoma Cells Differ in Their Rapid 170-Estradiol Signaling: Implications for Proliferation. *Endocrinology.* 2009; 150(5): 2436-2445.
67. Leibsohn S, d'Ablaing G, Mishell D R Jr, Schlaerth J B. Leiomyosarcoma in a series of hysterectomies performed for presumed uterine leiomyomas. Am J Obstet Gynecol 1990; 162:968-74; discussion 974-6.
68. Hussain N, Quezado M, Huizing M, Geho D, White J G, Gahl W, Mannon P. Intestinal disease in Hermansky-Pudlak syndrome: occurrence of colitis and relation to genotype. *Clin Gastroenterol Hepatol.* 2006 January; 4(1):73-80.
69. Wang, L. & Lyerla, T. Histochem Cell Biol (2010) 134: 205.

The invention claimed is:

1. A method comprising administering an agent capable of inhibiting interleukin 11 (IL-11)-mediated signalling to a subject in need thereof, wherein the subject has a disease selected from the group consisting of: vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, fibromuscular dysplasia (FMD), supravalvular stenosis, renal artery stenosis, plexiform lesions, telangiectasia, achalasia, dysphagia, diarrhoea, constipation, inflammatory bowel disease (IBD), bowel stricture, pyloric stenosis, coeliac disease, irritable bowel syndrome, diverticulitis, ulcerative colitis, focal and segmental glomerulosclerosis (FSGS), IgA nephropathy, Hutchinson-Gilford Progeria Syndrome (HGPS), leiomyoma, leiomyosarcoma and non-airway/non-lung-related pathology of Hermansky-Pudlak Syndrome (HPS), wherein the disease comprises cells having a TGFβ1-mediated pathological secretory smooth muscle cell (SMC) phenotype, and wherein the agent is an anti-IL-11 antibody or an antigen-binding fragment thereof, or an anti-IL-11Rα antibody or an antigen-binding fragment thereof.

2. The method according to claim 1, wherein SMCs are secretory SMCs.

3. The method according to claim 1, wherein SMCs are vascular SMCs (VSMCs).

4. A method for inhibiting the activity of smooth muscle cells (SMCs) in a subject in need thereof comprising:
   (a) selecting a subject who has a disease comprising cells having a TGFβ1-mediated pathological secretory smooth muscle cell (SMC) phenotype, wherein the disease is selected from the group consisting of: vascular aneurysm, Marfan's syndrome, aortic aneurysm, Furlong's syndrome, Sphrintzen-Goldberg syndrome, Loeys-Dietz syndrome, familial thoracic aortic aneurysm syndrome, arterial tortuosity syndrome, cerebral aneurysm, vascular stenosis and restenosis, fibromuscular dysplasia (FMD), supravalvular stenosis, renal artery stenosis, plexiform lesions, telangiectasia, achalasia, dysphagia, diarrhoea, constipation, inflammatory bowel disease (IBD), bowel stricture, pyloric stenosis, coeliac disease, irritable bowel syndrome, diverticulitis, ulcerative colitis, focal and segmental glomerulosclerosis (FSGS), IgA nephropathy, Hutchinson-Gilford Progeria Syndrome (HGPS), leiomyoma, leiomyosarcoma and non-airway/non-lung-related pathology of Hermansky-Pudlak Syndrome (HPS); and
   (b) administering an agent capable of inhibiting interleukin 11 (IL-11)-mediated signalling to the subject, wherein the agent is an anti-IL-II antibody or an antigen-binding fragment thereof, or an anti-IL-11Rα antibody or an antigen-binding fragment thereof.

5. The method according to claim 4, wherein SMCs are secretory SMCs.

6. The method according to claim 4, wherein SMCs are vascular SMCs (VSMCs).

7. The method of claim 1, wherein the SMCs express collagen I.

8. The method of claim 4, wherein the SMCs express collagen I.

* * * * *